United States Patent
Sato et al.

(10) Patent No.: US 6,593,045 B2
(45) Date of Patent: Jul. 15, 2003

(54) SUBSTRATE PROCESSING APPARATUS AND METHOD

(75) Inventors: Norikatsu Sato, Kikuchi-Gun (JP);
Kunie Ogata, Kikuchi-Gun (JP);
Yoshio Kimura, Kikuchi-Gun (JP);
Hiroshi Tomita, Kikuchi-Gun (JP);
Seiji Nakashima, Kikuchi-Gun (JP);
Hidehiko Kamiya, Kikuchi-Gun (JP)

(73) Assignee: Tokyo Electron Limited, Tokyo-To (JP)

( * ) Notice: Subject to any disclaimer, the term of this patent is extended or adjusted under 35 U.S.C. 154(b) by 69 days.

(21) Appl. No.: 09/902,159

(22) Filed: Jul. 11, 2001

(65) Prior Publication Data

US 2002/0009658 A1 Jan. 24, 2002

(30) Foreign Application Priority Data

Jul. 12, 2000 (JP) ........................................ 2000-211532
Jul. 18, 2000 (JP) ........................................ 2000-217722
Aug. 7, 2000 (JP) ........................................ 2000-238468

(51) Int. Cl.[7] ............................ G03F 9/00; B05C 11/00; B65G 49/07
(52) U.S. Cl. ............................. 430/30; 118/56; 118/58; 118/69; 382/145; 382/149; 414/763; 414/773; 414/811; 414/936; 414/937; 414/941
(58) Field of Search ............................ 430/30; 118/56, 118/58, 69; 382/145, 149; 414/763, 773, 811, 936, 937, 941

(56) References Cited

U.S. PATENT DOCUMENTS

| | | | |
|---|---|---|---|
| 5,899,690 A | 5/1999 | Nam et al. | 432/241 |
| 5,915,910 A | 6/1999 | Howells et al. | 414/331 |
| 6,051,349 A | 4/2000 | Yoshioka et al. | 430/30 |

FOREIGN PATENT DOCUMENTS

JP 1-239914 9/1989

Primary Examiner—Christopher G. Young
(74) Attorney, Agent, or Firm—Oblon, Spivak, McClelland, Maier & Neustadt, P.C.

(57) ABSTRACT

A cassette station, a processing station having a coating unit and a developing unit, and an inspecting station having a film thickness inspecting apparatus and a defect inspecting apparatus are disposed in the direction approximately perpendicular to the direction of the disposition of cassettes of the cassette station in such a manner that the inspecting station is disposed midway between the cassette station and the processing station. In the structure, the inspecting station and the processing station are connected and wafers are automatically transferred among the stations, operations from the substrate process to the inspection can be simplified and the time period necessary therefore can be shortened.

53 Claims, 40 Drawing Sheets

SUBSTRATE PROCESSING APPARATUS AND METHOD

BACKGROUND OF THE INVENTION

1. Field of the Invention

The present invention relates to a substrate processing apparatus and a substrate processing method for performing for example a resist solution coating process and a developing process for substrates such as semiconductor wafers and glass substrates for liquid crystal displays.

2. Description of the Related Art

In a semiconductor apparatus fabrication process, photolithography technology is used. In the photolithography technology, a resist solution is coated on a substrate such as a semiconductor wafer. With a photo mask, the resist film is exposed and developed. As a result, a desired resist pattern is formed on the substrate.

The photolithography technology is accomplished by a pattern forming system of which an aligner is connected to a coating and developing apparatus. When semiconductor wafers (hereinafter referred to as wafers) are processed, the coating and developing apparatus is composed of a carrier stage, a transfer mechanism, a process block, and an interface station. The carrier stage loads and unloads a wafer carrier. The transfer mechanism takes a wafer from a carrier placed on the carrier stage. The coating and developing apparatus is connected to the aligner. A wafer is transferred to a processing station through the transfer mechanism. The processing station coats a resist film on the wafer. The aligner exposes the wafer. Thereafter, the wafer is returned to the processing station. The processing station develops the wafer. The resultant wafer is returned to the carrier through the transfer mechanism.

After the processed wafer is placed in the carrier, the carrier is transferred from a carrier stage 11 to an inspecting unit disposed in another area this is different from the coating and developing apparatus 1 by an operator or an automatic transferring robot. The inspecting unit inspects the line widths of the resist pattern formed on the wafer, the matching of the resist pattern and the base pattern, the coated irregularities of the resist, the developing defects, and so forth. When the inspected result of the wafer is successful, it is transferred to the next process. When the inspected result of the wafer is NG, it is transferred to a cleaning unit. The cleaning unit dissolves the resist from the wafer so as to restore the wafer to the original state. The resultant wafer is transferred to the pattern forming system again. The pattern forming system performs the similar process for the wafer.

However, since the wafer that has been processed by the pattern forming system is transferred to the external inspecting unit that inspects the pattern of the wafer and then transferred to the next process, the throughput of the system deteriorates. In addition, the wafer should be queued while the inspecting unit is inspecting a wafer whose pattern has been formed by another pattern forming system. Thus, the throughput of the coating and developing apparatus does not advantageously affect the overall process. In addition, when the operator wants to know the inspected result of the pattern, he or she should walk to the place of the inspecting unit. Thus, it is inconvenient to evaluate the recipe of the process corresponding to the inspected result.

SUMMARY OF THE INVENTION

An object of the present invention is to provide a substrate processing apparatus and a substrate processing method that allows a substrate to be inspected without a deterioration of the throughput of a coating and developing apparatus and so forth.

Another object of the present invention is to provide a substrate processing apparatus and a substrate processing method that allows a substrate to be easily sample-inspected.

To accomplish the above-described objects, a first aspect of the present invention is a substrate processing apparatus, comprising a cassette station having a holding portion for holding a substrate cassette that contains a plurality of substrates, and a transferring portion for transferring the substrate to and from the substrate cassette placed on the holding portion, a processing station having a substrate processing portion for coating process solution on the substrate transferred from the cassette station, an inspecting station connected to the processing station, the inspecting station having an inspecting portion for inspecting a processed state of the substrate processing portion for the substrate, and a main transfer mechanism for transferring a substrate between the processing station and the inspecting station.

In such a structure, the inspecting station and the processing station are adjacently disposed. In addition, a substrate is automatically transferred between the inspecting station and the processing station. Thus, it is not necessary for the operator to perform the transferring operation. In addition, the transferring time for the wafer is short. Thus, the total operation from the substrate process to the inspection can be simplified. Moreover, since the processed state can be inspected on real time basis, the inspection accuracy is improved. As a result, the total operation time from the process to the inspection can be shortened.

A second aspect of the present invention is an apparatus for coating a resist on a substrate and developing the substrate that has been exposed, the apparatus being connected to an aligner, the apparatus comprising a carrier station having a carrier loading/unloading portion for loading and unloading a carrier that contains a plurality of substrates, and a transferring portion for transferring a substrate to and from the carrier on the carrier loading/unloading portion, a processing station disposed adjacent to the carrier station, the processing station having a coating portion for coating resist on the substrate, a developing portion for developing the substrate that has been exposed, and a main transferring portion for transferring the substrate to the coating portion and the developing portion and transferring the substrate to and from the transferring portion, an inspecting station disposed adjacent to the carrier station, the inspecting station having an inspecting portion for inspecting the substrate, an external carrier holding portion for holding a carrier that contains the substrate that has been processed outside the substrate processing apparatus, and a mode selecting portion for selecting a regular operation mode in which the inspecting portion inspects the substrate processed in the processing station or an inspecting portion dedicated operation mode in which the inspecting portion inspects the substrate processed outside the substrate processing apparatus.

The external carrier holding portion is disposed in the carrier station. The external carrier holding portion is a part of the carrier loading/unloading portion of the carrier station. The inspecting station has an auxiliary transferring portion for transferring the substrate to and from the inspecting portion. An intermediate holding portion is disposed in the carrier station, in the inspecting station, or midway between the carrier station and the inspecting station, the intermediate holding station temporarily holding a substrate. The transferring portion of the carrier station transfers the substrate developed in the processing station and the substrate contained in a carrier on the external carrier holding portion to and from the auxiliary transferring portion through the intermediate holding portion.

According to the present invention, since inspections such as a pattern inspection can be performed in the coating and developing apparatus, the throughput is improved. In addition, when a maintenance operation for the processing station that performs a coating process and a developing process is performed or when the developing process is stopped, the inspecting unit can be independently operated. Thus, a substrate brought from the outside of the system can be inspected.

A third aspect of the present invention is an apparatus that has a similar structure to the above-described aspects. In the third aspect, a second transferring portion is disposed in addition to the transferring portion (first transferring portion) of the carrier station. The second transferring portion transfers the substrate between a carrier on said external carrier holding portion and said inspecting station.

A fourth aspect of the present invention is an apparatus that has a similar structure to the above-described aspects. In the fourth aspect, an external carrier holding portion and an auxiliary transferring portion are disposed in the inspecting station.

A fifth aspect of the present invention is a substrate processing apparatus, comprising a cassette station having a holding portion for holding a substrate cassette that contains a plurality of substrates, and a transferring portion for transferring the substrate to and from the substrate cassette on the holding portion, a processing station disposed adjacent to the cassette station, the processing station having a substrate processing portion for coating process solution on the substrate, and a main transfer mechanism for transferring substrates to the substrate processing portion in the order of those contained in a substrate cassette and transferring the substrates to and from the transferring portion in the order of those contained in the substrate cassette, an inspecting portion for inspecting the processed state of the substrate processing portion for the substrate, an inspecting substrate holding portion for holding an inspecting substrate that has been processed outside the substrate processing apparatus and that is inspected in the inspecting portion, a substrate holding portion for holding substrates that have been processed in the substrate processing portion and that are later than the inspecting substrate in the substrate cassette in the order of those contained therein, and a main transfer mechanism for transferring the substrate that has been processed in the substrate processing portion to the inspecting substrate holding portion and the substrate holding portion.

In such a structure, since the substrate processing apparatus is provided with the inspecting portion, it is not necessary to convey a substrate for a longer distance than the case that the inspecting portion is disposed as an external apparatus. Thus, the transferring time is short. As a result, the throughput of the system is improved.

The above-described apparatus performs a substrate processing method, comprising the steps of transferring a plurality of substrates contained in a substrate cassette to a substrate processing portion in the order of the substrates contained in the substrate cassette and coating process solution on the substrates, unloading a substrate processed in the substrate processing portion from the substrate processing portion, transferring an n-th (n is any integer equal to or larger than 1) inspecting substrate that is contained in the substrate cassette and that is unloaded from the substrate processing portion to an inspecting portion and causing the inspecting portion to inspect the processed state of the substrate processing portion, transferring substrates later than an inspecting substrate to a substrate holding portion and causing the substrate holding portion to hold the substrates in the order of the substrates contained in the substrate cassette until the inspecting portion completes the inspection of the inspecting substrate when the process time period of the inspecting portion is longer than the transferring intervals of substrates transferred from the substrate processing portion, unloading the inspecting substrate that has been inspected in the inspecting portion from the inspecting portion, and unloading the inspecting substrate from the inspecting portion and then unloading the substrates held in the substrate holding portion therefrom in the order of the substrates contained in the substrate cassette.

According to the present invention, when a substrate that has been processed in the substrate processing portion is sample-inspected and the process time of the inspecting portion is longer than the transferring interval of substrates to the substrate processing portion, while an inspecting substrate is being inspected, substrates that are not inspected are queued in the substrate holding portion. Thus, without need to provide a complicated sample-inspecting transferring program, substrates can be returned to the original cassette in the order of those contained therein.

These and other objects, features and advantages of the present invention will become more apparent in light of the following detailed description of a best mode embodiment thereof, as illustrated in the accompanying drawings.

DESCRIPTION OF PREFERRED EMBODIMENTS

Next, embodiments of the present invention will be described.

Figure 1:
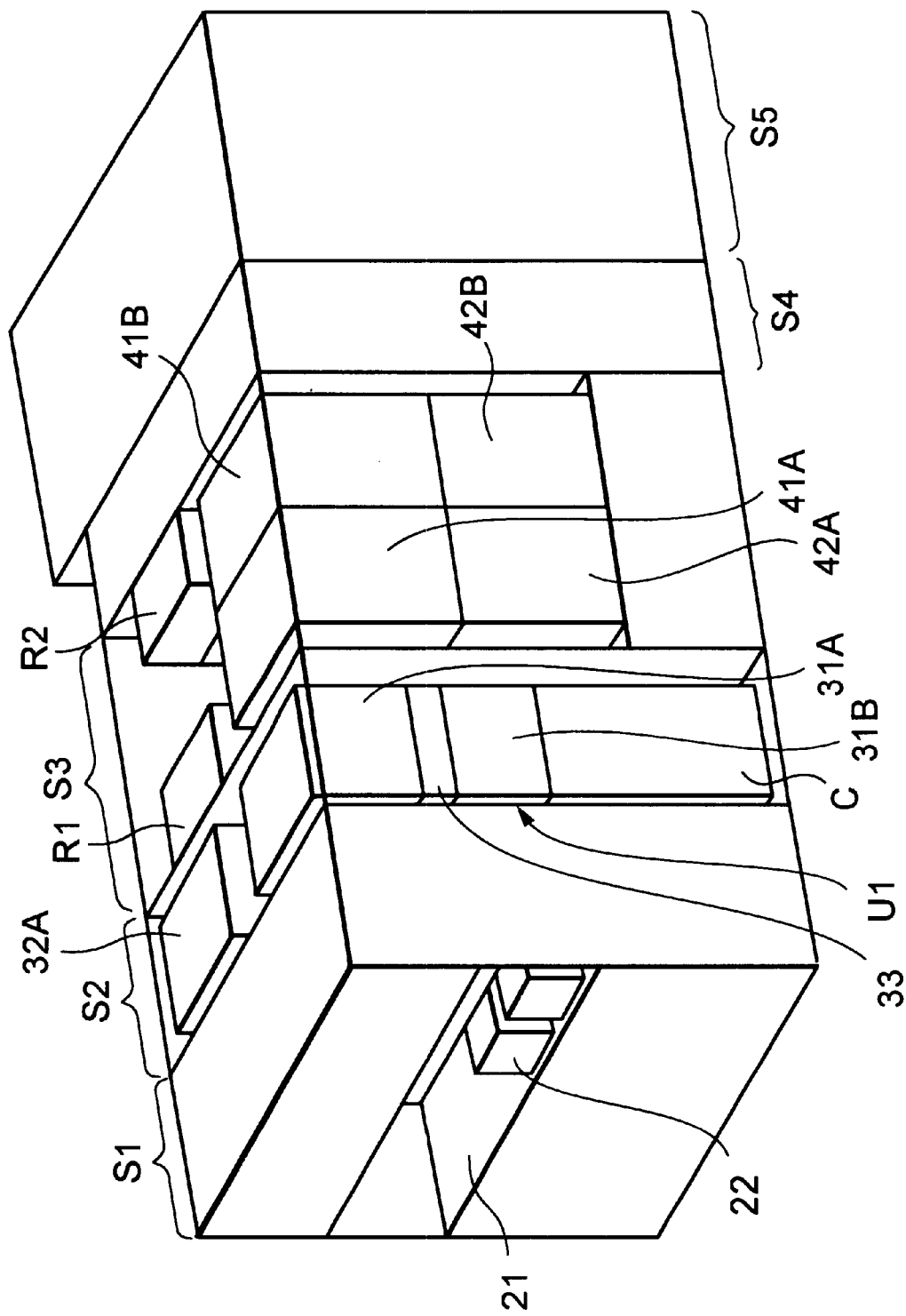
FIG. 1 is a schematic perspective view showing a coating and developing apparatus according to an embodiment of the present invention.
Figure 2:
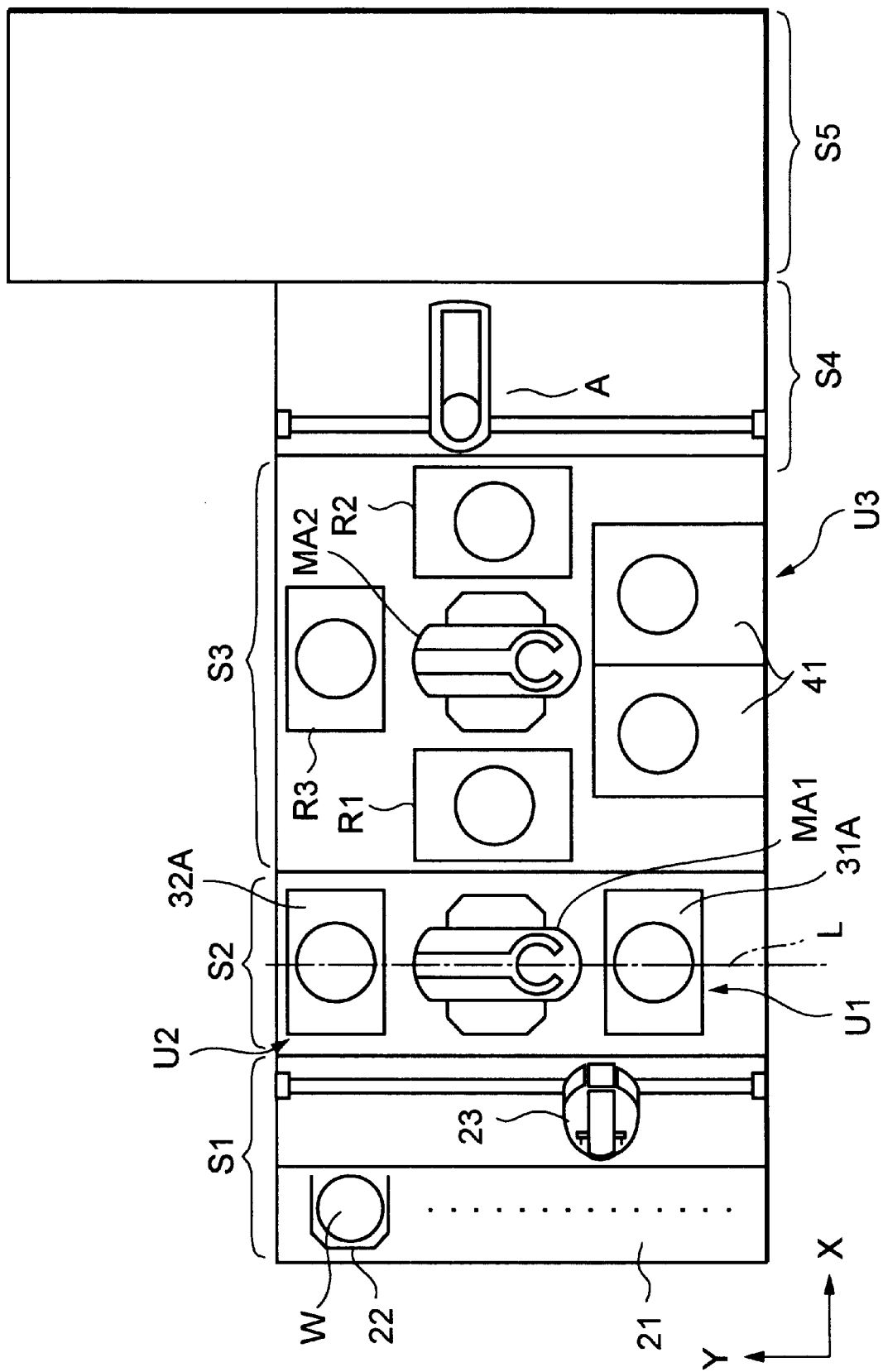
FIG. 2 is a schematic plan view showing the coating and developing apparatus.

FIG. 1 is a schematic, exploded perspective view showing the interior of an embodiment of the present invention. FIG. 2 is a schematic plan view of the embodiment. In FIGS. 1 and 2, S1 represents a cassette station. S2 represents an inspecting station that performs a particular inspection for a wafer W. S3 represents a processing station that performs substrate processes such as a resist coating process, a developing process, and so forth for a wafer W. S4 represents an interface station. S5 represents an aligner.

The cassette station S1 has a cassette stage 21, a cassette 22, and a transfer mechanism 23. The cassette stage 21 is a holding portion that holds wafer cassettes (hereinafter referred to as cassettes) that are for example four substrate cassettes. Each cassette contains a plurality of substrates (for example, 25 wafers). Each cassette 22 is placed on the cassette stage 21. The transfer mechanism 23 is a transferring portion that transfers a wafer W to and from a transferring portion 33 (that will be described later) of the inspecting station S2. The transfer mechanism 23 is structured so that it can be elevated, moved in the X and Y directions, and rotated around the vertical axis.

Figure 3:
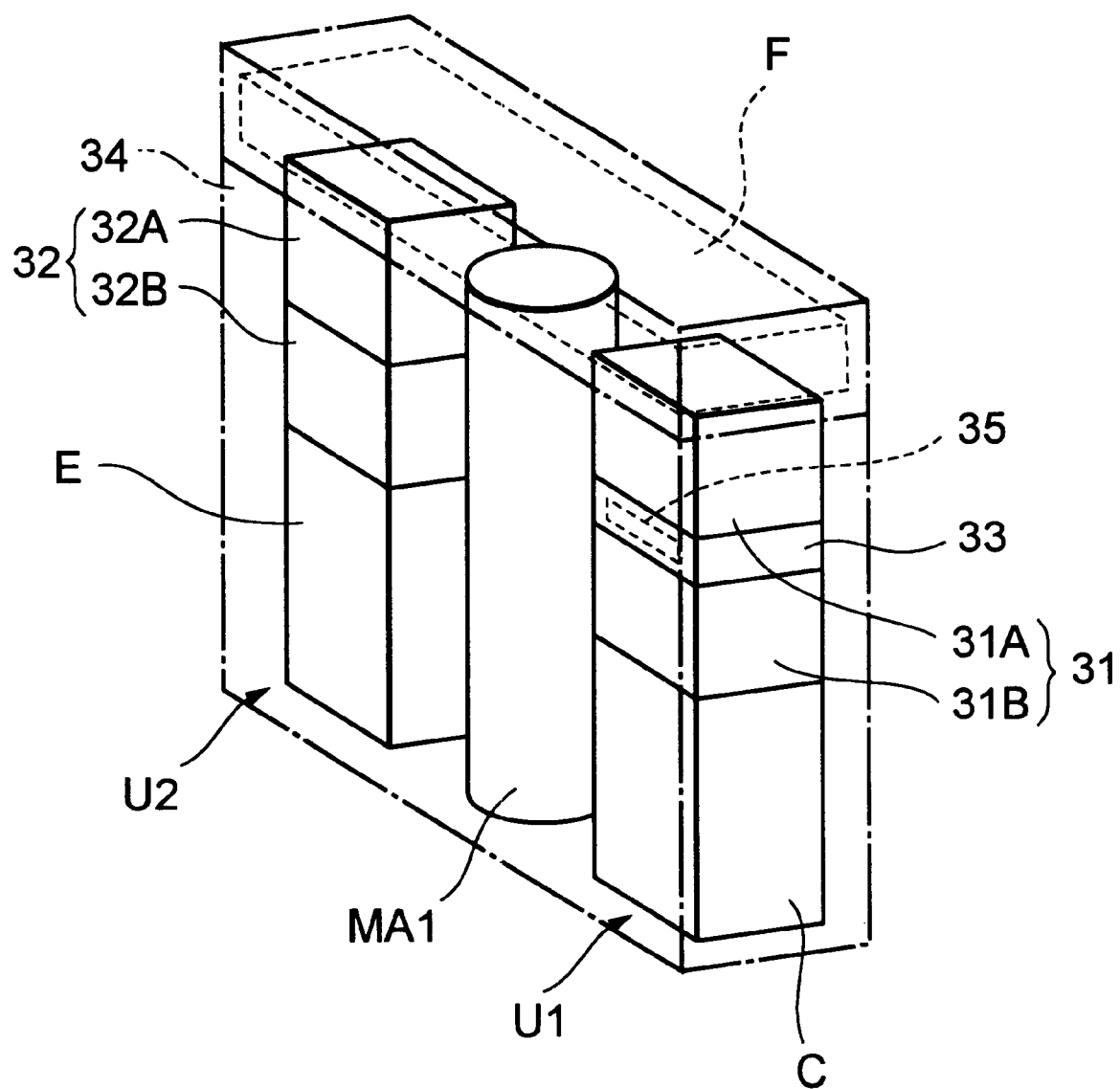
FIG. 3 is a perspective exploded view showing an inspecting station of the coating and developing apparatus.

The inspecting station S2 is connected to the cassette station S1 in the direction approximately perpendicular to the direction of the disposition of the cassettes placed on the cassette station S1. As shown in FIGS. 2, 3 (perspective view of the inspecting station S2), and 4 (sectional view of the inspecting station S2 viewed from the processing station S3), the inspecting station S2 has inspecting apparatuses that are inspecting portions that inspect processed states of a plurality of substrates for example two film thickness inspecting apparatuses 31 (31A, 31B), two defect inspecting apparatuses 32 (32A, 32B), one transferring portion 33, a chemical unit C that is one holding portion, an electric unit E that is for example one holding portion, and one main transfer mechanism MA1. The inspecting station S2 inspects predetermined substrate process states such as the film thickness of resist film, developed line widths, presence/absence of scratches of resist film, coated irregularities of resist solution, developing defects, and so forth for a wafer that has been coated with the resist solution and developed.

Next, an example of the layout of the inspecting station S2 will be described. For example, on the far side of the cassette station S1, for example, on the right side viewed from the cassette station S1, a first inspecting unit U1 is disposed. The first inspecting unit U1 has a plurality of inspecting units that are two film thickness inspecting apparatuses 31A and 31B. As mentioned above, the first inspecting unit U1 has transferring portion 33 disposed midway between the film thickness inspecting apparatuses 31A and 31B. On the lower side of the first inspecting unit U1, the chemical unit C is disposed.

The film thickness inspecting apparatuses 31 are apparatuses that optically inspect the thickness of a base film formed on a substrate (for example, the thickness of a coated resist film such as an oxide film or poly-silicon film) by optical interference method. The transferring portion 33 has a transferring table on which a wafer W is transferred between the transfer mechanism 23 of the cassette station S1 and the main transfer mechanism MA1. An elevating pin (not shown), the transfer mechanism 23, and the main transfer mechanism MA1 cooperatively transfer a wafer W to and from the transferring table. The elevating pin can be elevated by an elevating mechanism.

The chemical unit C has a supplying system that supplies a material for example a chemical solution that is used in a coating unit and so forth (that will be described later).

The chemical unit C has for example reservoir tanks for solvents and resist solutions, various types of valves such as open/close valves of the reservoir tanks, filters, valve driving portions, and discharge nozzle driving systems.

When viewed from the cassette station S1, on the left side, the second inspecting unit U2 is disposed. The second inspecting unit U2 has a plurality of inspecting apparatuses that are the defect inspecting apparatuses 32A and 32B. On the lower side of the second inspecting unit U2, the above-mentioned electric unit E is disposed.

The defect inspecting apparatuses 32 inspect scratches on the front surface of a resist film, the matching of the resist patterns of the upper layer and the lower layer, presence/absence of foreign matters in resist solution, coated irregularities of resist solution, and developing defects using pictures photographed by a CCD camera (that will be described later). The electric unit E has electric apparatuses such as a power supply portion, a controller, and a power panel that are used for the film thickness inspecting apparatuses 31, the defect inspecting apparatuses 32, the main transfer mechanism MA1, the coating unit, and the developing unit (that will be described later).

Next, with reference to FIG. 4, an example of the film thickness inspecting apparatus 31 will be described. The film thickness inspecting apparatus 31 comprises a housing 100, a rotating holding table 110, a CCD camera 120, and a lighting portion 130. The housing 100 has an opening from which a wafer W is transferred. The rotating holding table 110 is disposed in the housing 100. The rotating holding table 110 horizontally holds a wafer W and adjusts the orientation thereof. The CCD camera 120 photographs the front surface of a wafer W placed on the rotating holding table 110. The CCD camera 120 can be moved in the X, Y, and Z directions. A picture of a wafer W photographed by the CCD camera 120 is analyzed by a personal computer (not shown) that is a data processing portion so as to inspect the wafer W. Alternatively, the CCD camera 120 may be fixed, whereas the rotating holding table 110 for the wafer W may be moved in the X, Y, and Z directions.

The film thickness inspecting apparatus 31 further comprises a film thickness probe 140 disposed at one side of the CCD camera 120. In FIG. 4, the film thickness probe 140 is denoted as a dotted line block. The film thickness probe 140 has a light emitting portion and a light receiving portion. The film thickness probe 140 radiates light to a wafer W and obtains the reflection ratio thereof. The obtained reflection ratio is analyzed by the computer. As a result, the film thickness can be obtained.

The main transfer mechanism MA1 is disposed between the first inspecting unit U1 and the second inspecting unit U2. The main transfer mechanism MA1 transfers a wafer W between each of the first inspecting unit U1 and the second inspecting unit U2 and a transferring portion 46 of the processing station S3 (that will be described later). The main transfer mechanism MA1 can be elevated, moved leftward and rightward, moved forward and backward, and rotated around the vertical axis. For simplicity, in FIG. 1, the main transfer mechanism MA1 is omitted.

In the example, the structure of which the inspecting station S2 having the chemical unit C and the electric unit E was described. Alternatively, the inspecting station S2 may not have both the chemical unit C and the electric unit E. In other words, the inspecting station S2 may have either the chemical unit C or the electric unit E. In addition, the inspecting station S2 may have only inspecting portions such as the film thickness inspecting apparatus 31 or the defect inspecting apparatus 32. Furthermore, the number of inspecting portions disposed in the inspecting station S2 may be one rather than two as necessary. Alternatively, a plurality of inspecting portions of the inspecting station S2 may be disposed on three stages or four stages. In addition, as inspecting portions, only the film thickness inspecting apparatuses 31 or the defect detecting apparatuses 32 may be disposed. Alternatively, in addition to those apparatuses, other inspecting apparatuses may be disposed.

In addition, the inspecting station S2 is independently disposed. In other words, as shown in FIGS. 3 and 4, the inspecting station S2 is partitioned off with a wall portion 34 from the other space. Corresponding to the transferring portion 33 of the inspecting station S2 adjacent to the cassette station S1 and the processing station S3, transferring openings 35 through which the transfer mechanism 23 transfers a wafer W to the transferring portion 33 are formed in the wall portion 34. In addition, corresponding to the transferring portion 46 of the processing station S3, transferring opening (not shown) through which the main transfer mechanism MA1 transfers a wafer W to the transferring portion 46 are formed in the wall portion 34.

Figure 5:
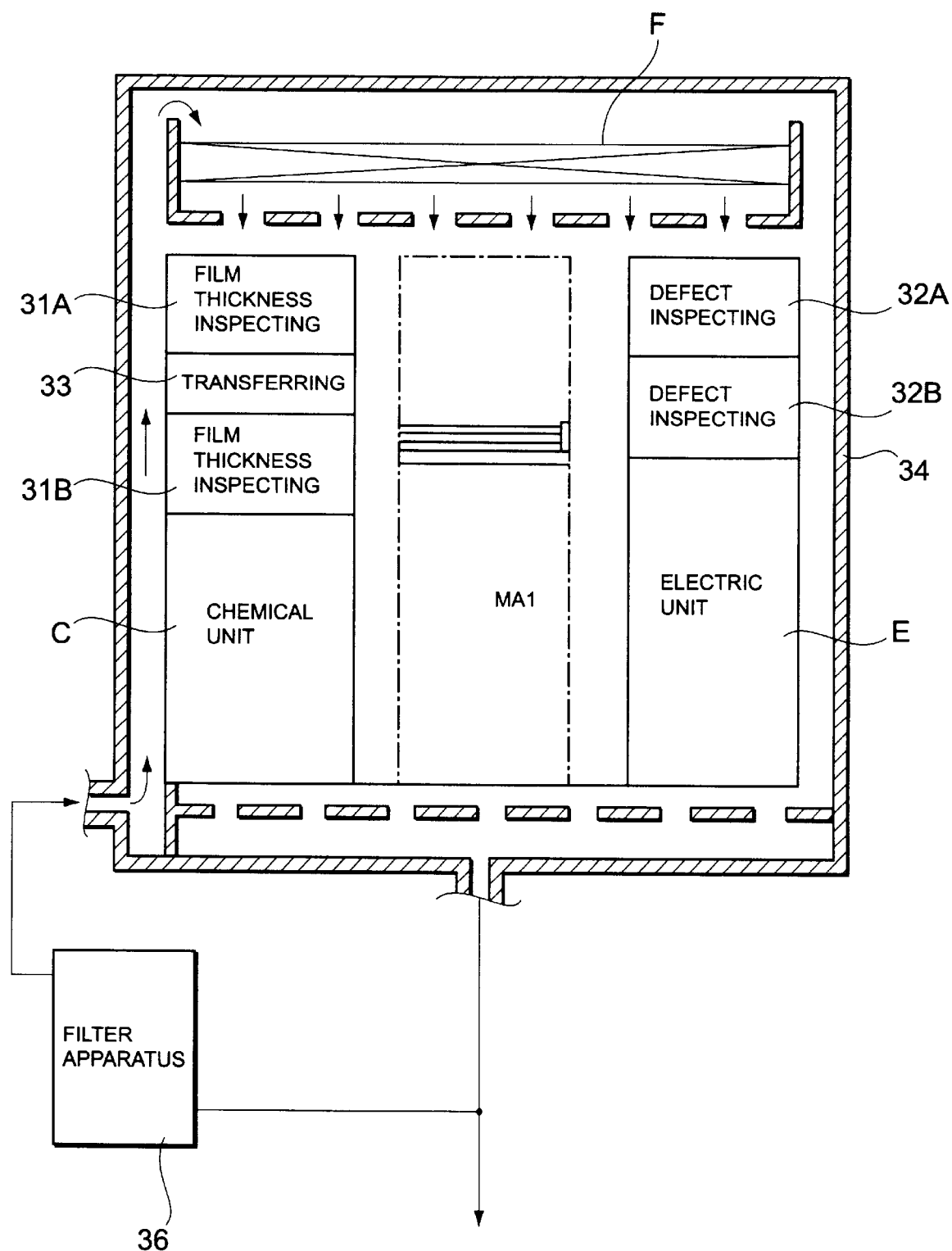
FIG. 5 is a sectional view showing the inspecting station.

As shown in FIG. 5, a filter unit F is disposed in the inspecting station S2 partitioned off with the wall portion 34 in such a manner that the filter unit F covers the top of the inspecting station S2. Atmospheric gas collected from the lower portions of the chemical unit C and the electric unit E is exhausted to a plant exhausting system. In addition, part of the atmospheric gas is supplied to a filter apparatus 36 that is an adjusting portion. The filter apparatus 36 purifies the atmospheric gas and adjusts its temperature and humidity to predetermined values. The adjusted air is supplied as a down flow to each portion through the filter unit F. The filter unit F has an air purifying filter, a sucking fan, and so forth. The filter apparatus has an impurity removing portion, a heating mechanism, a humidifying mechanism, an air supplying portion, and so forth. Alternatively, without an air circulating portion, air whose temperature and humidity have been adjusted may be supplied to each inspecting portion. Air of a clean room may be supplied to the cassette station S1.

In the inspecting station S2, the first inspecting unit U1, the second inspecting unit U2, and the main transfer mechanism MA1 are symmetrically disposed with respect to a dashed line L that divides the X direction of the inspecting station S2 into nearly two portions. In other words, when the inspecting station S2 is rotated by a half turn and thereby the second inspecting unit U2 is positioned on the right of the cassette station S1, the transfer mechanism 23 of the cassette station S1 can access the transferring portion 33 through the transferring opening 35. In addition, the main transfer mechanism MA1 of the inspecting station S2 can access a shelf unit R1 of the processing station S3 through a transferring opening (not shown).

In addition, the processing station S3 is connected to the inspecting station S2 in the direction approximately perpendicular to the direction of the disposition of the cassettes placed on the cassette station S1. The processing station S3 has two developing units 41 (41A and 41B) as substrate processing portions, two coating units 42 (42A and 42B) as substrate processing portions, three shelf units R (R1, R2, and R3), and one main transfer mechanism MA2. The processing station S3 transfers a wafer W between the inspecting station S2 and the interface station S4. The processing station S3 performs a resist solution coating process, a developing process, a heating process heating wafer W to a predetermined temperature before and after these processes, and a cooling process for a wafer W.

Next, an example of the layout of the processing station S3 will be described. For example, when viewed from the cassette station S1, on the right, a processing unit U3 is disposed. The processing unit U3 is composed of two stages. Each stage of the processing unit U3 has a developing unit 41 and a coating unit 42. In the following description, the cassette station S1 side is referred to as near side, whereas the aligner S5 side is referred to as far side.

When viewed from the cassette station S1 of the processing unit U3, on the left, a main transfer mechanism MA2 is disposed. The main transfer mechanism MA2 transfers a wafer W among the coating units 42, the developing units 41, and the shelf units R. The main transfer mechanism MA2 can be elevated, moved leftward and rightward, moved forward and backward, and rotated around the vertical axis. When viewed from the cassette station S1, on the near side of the main transfer mechanism MA2, on the far side of the main transfer mechanism MA2, and the left side of the main transfer mechanism MA2, the shelf unit R1, the shelf unit R2, and the shelf unit R3 are disposed, respectively. However, for simplicity, in FIG. 1, the shelf unit R3 and the main transfer mechanism MA2 are omitted.

In the processing station S3, sufficient space is made for each of the processing unit U3 and of the shelf unit R3 so that they are disposed to face the first inspecting unit U1 and the second inspecting unit U2 of the inspecting station S2, respectively.

Figure 6:
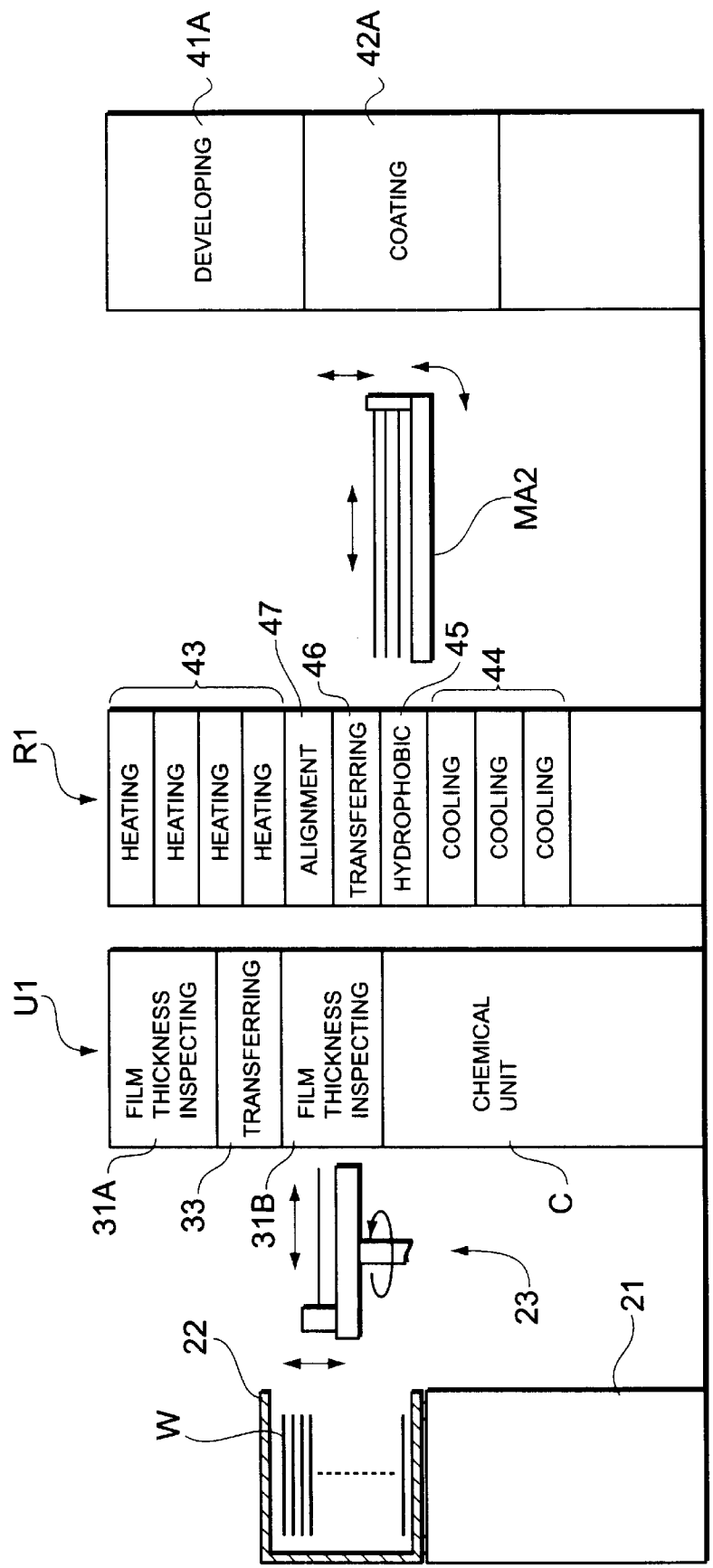
FIG. 6 is a side view showing an example of a first inspecting unit, a shelf unit, and a processing unit.

As an example of the shelves R, referring to FIG. 6, the shelf unit R1 has a heating portion 43, a cooling portion 44, a hydrophobic portion 45, a transferring portion 46, and an alignment portion 47 that are successively disposed in the vertical direction. The heating portion 43 heats a wafer W. The cooling portion 44 cools a wafer W. The hydrophobic portion 45 performs a hydrophobic process for the front surface of a wafer W. In the shelf unit R1, the transferring portion 46 has a transferring table on which a wafer W is transferred between the main transfer mechanism MA1 of the inspecting station S2 and the main transfer mechanism MA2 of the processing station S3. In the shelf unit R2, the transferring portion 46 has a transferring table on which a wafer W is transferred between the main transfer mechanism MA2 of the processing station S3 and a transfer mechanism A of the interface station S4 (that will be described later). The alignment portion 47 aligns a wafer W.

Figure 7:
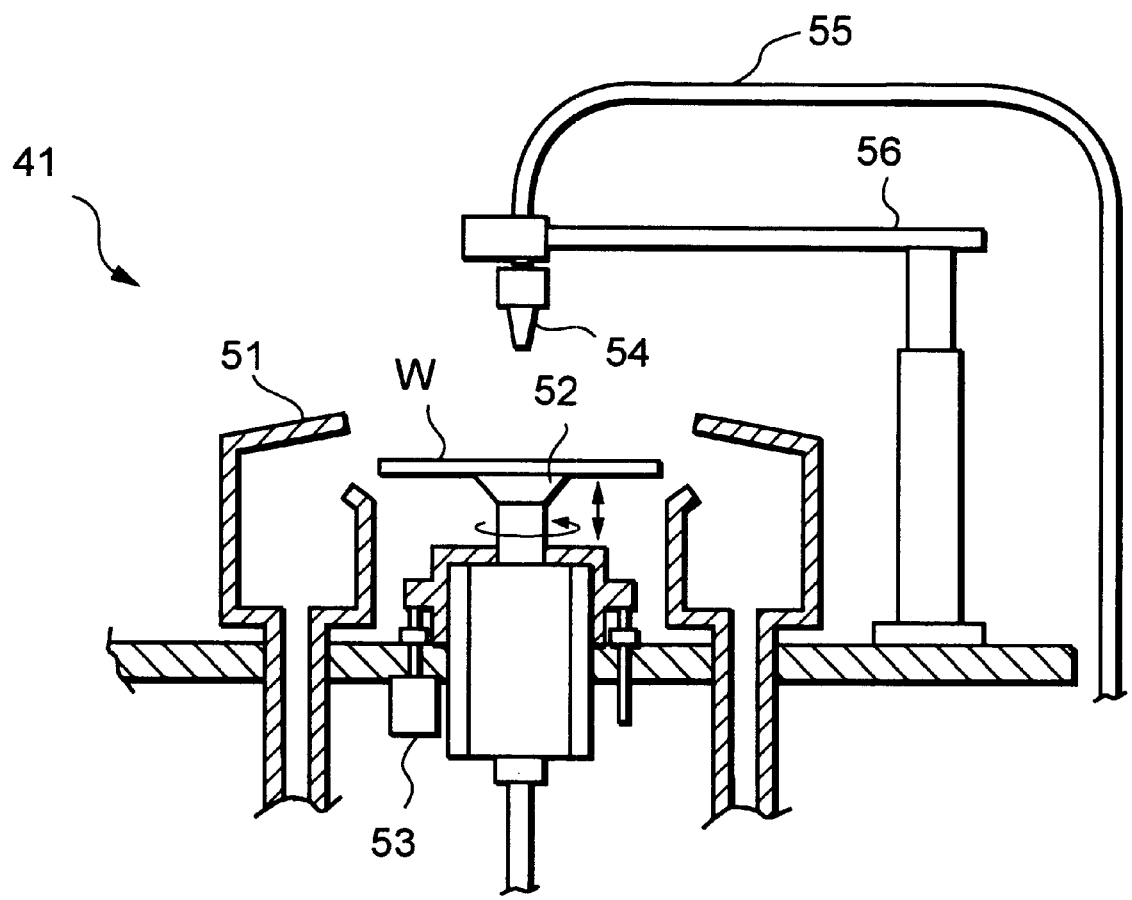
FIG. 7 is a sectional view showing a coating unit.

Next, with reference to FIG. 7, the developing unit 41 will be described. In FIG. 7, reference numeral 51 represents a cup. A spin chuck 52 that has a vacuum absorption function and that is rotatable is disposed in the cup 51. The spin chuck 52 can be elevated by an elevating mechanism 53. When the spin chuck 52 is positioned on the upper side of the cup 51, a wafer W is transferred with an arm 61, (that will be described later), of the main transfer mechanism MA1.

When a wafer W is transferred from the arm 61 to the spin chuck 52, the spin chuck 52 rises from relatively lower position and receives the wafer W from the arm 61 on the upper side of the cup 51. When a wafer W is transferred from the spin chuck 52 to the arm 61, the reverse operation is performed. In FIG. 7, reference numeral 54 represents process solution discharging nozzle. Reference numeral 55 represents process solution supplying pipe. Reference numeral 56 represents a supporting arm that horizontally moves the nozzle.

The discharging nozzle 54 has many discharging holes arranged in for example the diameter direction of a wafer W. The discharging nozzle 54 discharges developing solution on the front surface of the wafer W placed on the spin chuck 52. The spin chuck 52 is rotated by a half turn so as to deposit the developing solution on the wafer W and thereby form the film thereon.

Although the structure of the coating unit 42 is almost the same as the structure of the developing unit 41, the discharging nozzle 54 of the coating unit 42 discharges the process solution to almost the center of the wafer W. The discharging nozzle 54 drops the resist solution as process solution on the front surface of the wafer W placed on the spin chuck 52. The spin chuck 52 is rotated so as to spread the resist solution on the wafer W.

Figure 8:
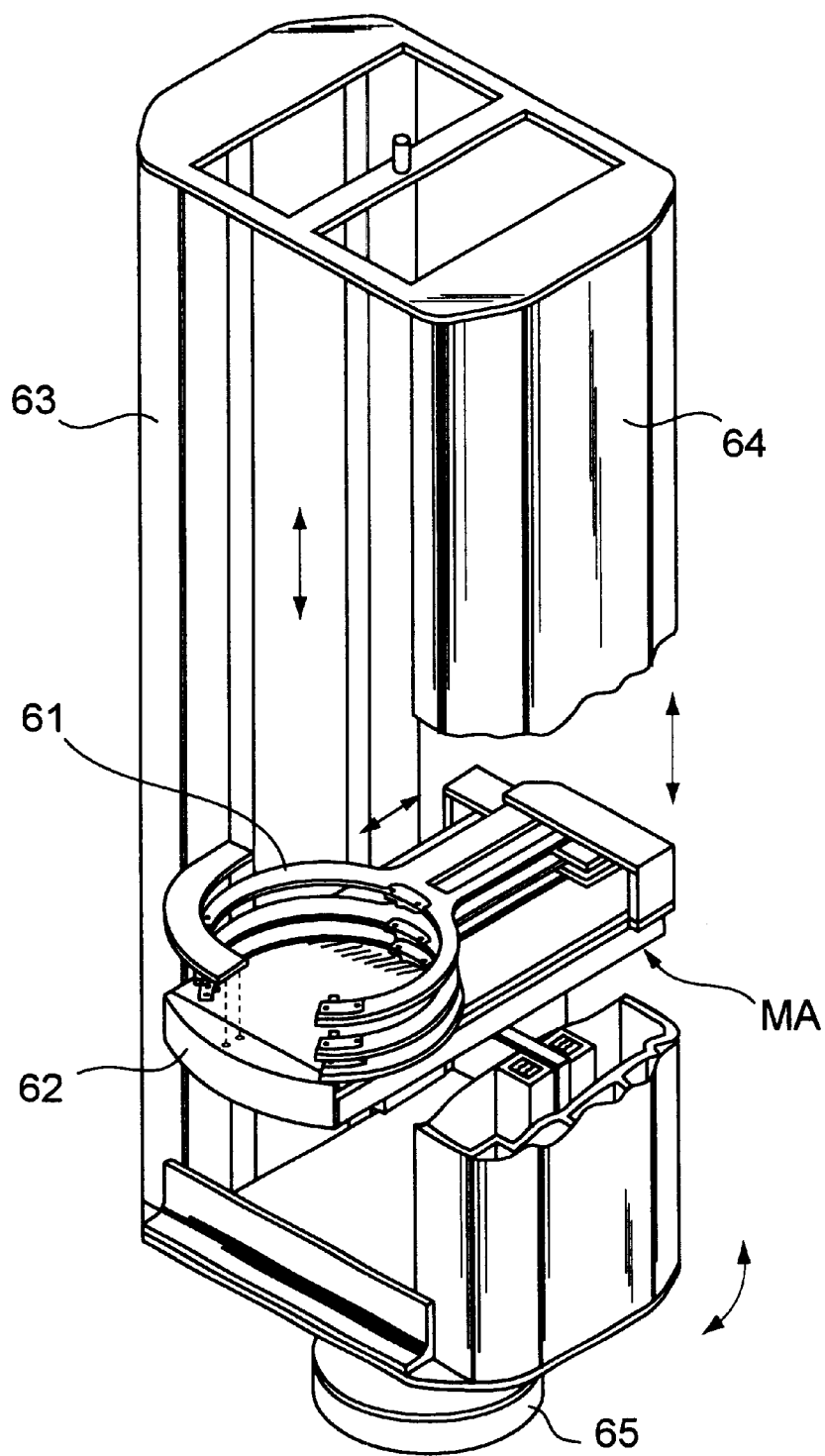
FIG. 8 is a perspective view showing a main transfer mechanism.

As shown in FIG. 8, the main transfer mechanism MA (MA1 and MA2), each have three arms 61, a pedestal 62, and a pair of guide rails 63 and 64. The three arms hold wafers W. The pedestal 62 holds the arms 61 so that they can be moved forward and backward. The guide rails 63 and 64 hold the pedestal 62 so that it can be elevated. By rotating the guide rails 63 and 64 with a rotation driving portion 65, the wafer W can be moved forward and backward, elevated, and rotated around the vertical axis.

The processing station S3 is adjacently connected to the interface station S4. On the far side of the interface station S4, the aligner S5 is connected. The aligner S5 exposes a wafer W on which a resist film has been formed. The interface station S4 has a transfer mechanism A that transfers a wafer W between the processing station S3 and the aligner S5. The transfer mechanism A can be elevated, moved leftward and rightward, moved forward and backward, and rotated around the vertical axis so as to transfer a wafer W between the transferring portion 46 of the shelf unit R2 of the processing station S3 and the aligner S5.

The width of the inspecting station S2 is not larger than the width in the direction of the disposition of each of the cassette station S1 and the processing station 53 (namely, the length of the disposition of the cassettes 22 of the cassette station S1 in the Y direction shown in FIG. 2). In addition, the cassette station S1, the inspecting station S2, the processing station S3, and the interface station S4 can be connected and disconnected with each other. In other words, as exemplified by the inspecting station S2 shown in FIG. 3, each structural station is partitioned by a wall portion. Each structural portion is connected by, for example, connecting members such as joint fasteners, screws, and magnets. Thus, as was described above, the inspecting station S2 can be disposed midway between the cassette station S1 and the processing station S3. Alternatively, the inspecting station S2 can be disposed midway between the processing station S3 and the interface station S4. In addition, for example caster rollers are mounted at a lower portion of the inspecting station S2 so that it can be moved forward and backward (in the Y direction of FIG. 2) so that the main transfer mechanism MA1 can easily be maintained.

Next, the operation of the above-described embodiment will be described. First of all, an automatic transferring robot (or an operator) transfers a cassette 22 that contains for example 25 wafers W to the cassette stage 21. The transfer mechanism 23 takes a wafer W from the cassette 22 and places the wafer W on the transferring portion 33 of the inspecting station S2 through the transferring opening 35 of the wall portion 34.

Thereafter, the main transfer mechanism MA1 transfers the wafer W to a film thickness inspecting apparatus 31 of the inspecting station S2. The film thickness inspecting apparatus 31 measures the film thickness of bare silicon of the wafer W. Thereafter, the main transfer mechanism MA1 of the inspecting station S2 places the wafer W on the transferring portion 46 of the shelf unit R1 of the processing station S3. Thereafter, the main transfer mechanism MA2 of the processing station S3 transfers the wafer W in the path of the hydrophobic portion 45 of the shelf unit R, the cooling portion 44 of the shelf unit R, and the coating unit 42. After the hydrophobic portion 45 performs the hydrophobic process for the wafer W, the cooling portion 44 cools the wafer W to the predetermined temperature. Thereafter, the coating unit 42 coats a resist solution on the wafer W at the predetermined temperature.

The wafer W that has been coated with the resist solution is transferred to the main transfer mechanism MA1 of the inspecting station S2 through the transferring portion 46 of the shelf unit R1. The film thickness inspecting apparatus 31 measures the film thickness of the resist film. Thereafter, the wafer W is transferred to the processing station S3. The main transfer mechanism MA2 transfers the wafer W to the aligner S5 through the transferring portion 46 of the shelf unit R2 and the transfer mechanism A of the interface station S4. The aligner S5 exposes the wafer W.

The exposed wafer W is transferred to the processing station S3 through the aligner S5, the transfer mechanism A of the interface station S4, and the transferring portion 46 of the shelf unit R2 of the processing station S3. The main transfer mechanism MA2 transfers the wafer W in the path of the heating portion 43 of the shelf unit R, the cooling portion 44 of the shelf unit R, and the developing unit 41. The developing unit 41 develops the wafer W at a predetermined temperature as a coating temperature of the developing solution (for example, 23° C.).

Thereafter, the main transfer mechanism MA2 of the processing station S3 transfers the wafer W in the path of the heating portion 43 of the shelf unit R, the cooling portion 44 of the shelf unit R, and the transferring portion 46 of the shelf unit R. The main transfer mechanism MA1 of the inspecting station S2 takes the wafer W from the transferring portion 46. The main transfer mechanism MA1 of the inspecting station S2 transfers the wafer W to a defect inspecting apparatus 32. The defect inspecting apparatus 32 inspects the processed state of the developing process for the wafer W such as measurement of the developed line widths, presence/absence of scratches of front surface of the resist film, matching of resist patterns of the upper layer and lower layer, presence/absence of foreign matter of coated resist, and coated irregularities of resist solution.

Thereafter, the main transfer mechanism MA1 transfers the inspected wafer W to the transferring portion 33. The transfer mechanism 23 returns the wafer W to the original cassette 22.

In the above-described system, the wafer W is transferred from the film thickness inspecting apparatus 31 to the transferring portion 46 of the shelf unit R1 of the processing station S3 through the transferring portion 33 of the inspecting station S2. Thereafter, the wafer W is transferred in the path of a free hydrophobic portion 45, a free cooling portion 44, a free coating unit 42, the transferring portion 46 of the shelf unit R1, a free film thickness inspecting apparatus 31 of the inspecting station S2, the transferring portion 46 of the shelf unit R of the processing station S3, and the interface station S4. The exposed wafer W is transferred in the path of the interface station S4, a free heating portion 43 of the processing station S3, a free cooling portion 44, the developing unit 41, a free heating portion 43, a free cooling portion 44, and the transferring portion 46 of the shelf unit R1. Thereafter, the wafer W is transferred in the path of a free defect inspecting apparatuses 32 of the inspecting station S2 and the transferring portion 33.

According to the above-described embodiment, a station having inspecting apparatuses is disposed midway between the cassette station S1 and the processing station S3. Thus, one operator can supervise resist coating process, exposing process, developing process, and inspection. Thus, the number of operators can be reduced. In addition, when any defect is detected in an inspection, the cause thereof can be quickly sought and countermeasures thereof can be quickly taken.

Since a wafer W is automatically transferred between the processing station S3 and the inspecting station S2, the total operation can be simplified without operator's intervention. In addition, since the transferring time of a wafer W between the stations S2 and S3 is short, the total operation time for the operation from the substrate process to the inspection can be shortened. In addition, since the processed state of the developing process can be supervised on real time basis, a wafer W can be more accurately inspected than before. In addition, any defect can be quickly detected. Moreover, since an inspecting apparatus is disposed in a coating and developing apparatus, a facility that suppresses particles from occurring can be shared.

As was described above, when the inspecting station S2 is structured in combination of a plurality of inspecting apparatuses, a plurality of inspections can be performed for a wafer W in the same station. In addition, since the transferring time between each inspecting apparatus is very short, the total inspecting time can be shortened.

In addition, since the width in the direction perpendicular to the direction of the disposition of the inspecting station S2 is not larger than the width of each of the cassette station S1 and the processing station S3, no portion of the cassette station S1 to the interface station S4 protrudes in the Y direction of FIG. 2. Thus, the stations can be advantageously laid out.

When the width of the inspecting station S2 is the same as the width of the cassette station S1 and the inspecting station S2 has a plurality of inspecting apparatuses, the width in the direction of the disposition of the inspecting station S2 (namely, the length in the X direction of FIG. 2) can be increased corresponding to the types and sizes of the inspecting apparatuses. Thus, even if a plurality of inspecting apparatuses are disposed, the inspecting station S2 has a predetermined space. In other words, on the lower side of the first inspecting unit U1 and the second inspecting unit U2, the chemical unit C and the electric unit E can be disposed, respectively. In recent years, since the number of types of resist solutions tends to increase, the spaces for the chemical system and the electric system can be effectively used.

In addition, when the atmospheric temperature of an inspecting apparatus exceeds 30° C., it adversely affects the measuring accuracy of the inspecting apparatus. Thus, it is preferred not to dispose an inspecting apparatus adjacent to the heating portions 43 of the shelf units R. However, according to the above-described embodiment, predetermined spaces are kept adjacent to the first inspecting unit U1 and the second inspecting unit U2 of the processing station S3. Thus, each inspecting apparatus disposed in the first inspecting unit U1 and the second inspecting unit U2 can be prevented from being affected by the temperature of the processing station S3.

At that point, even if the first inspecting unit U1 and the second inspecting unit U2 are disposed adjacent to the heating portions of the shelf units R, since the inspecting station S2 is partitioned off from the processing station S3 by the wall portion 34, each inspecting apparatus is suppressed from being affected by the temperature of the processing station S3. When the filter apparatus 36 that also operates as a temperature adjusting apparatus can adjust the temperature and humidity of the interior of the inspecting station S2 to predetermined values, each inspecting apparatus can accurately perform a designated inspection without an influence of the atmospheric temperature and humidity. When the first inspecting unit U1 and the second inspecting unit U2 are disposed adjacent to the heating portions of the shelf units R, a heat insulating portion that is for example a heat insulating material or a pipe for circulating temperature controlled water may be disposed between each of the first inspecting unit U1 and the second inspecting unit U2 and the heating portions. In addition, the atmospheric temperature and humidity of the inspecting station S2 may be adjusted corresponding to the measurement purpose. Furthermore, the atmosphere corresponding to one of for example coating process, developing process, and exposing process may be adjusted. It is preferred to satisfy the relation of inner pressure of processing station S3>inner pressure of cassette station S1>pressure of inspecting station S2>inner pressure of clean room. In other words, it is preferred that the processing station S3 has the highest positive pressure and the inspecting station S2 and the clean room have negative pressures. Thus, in a process of the system, foreign matter can be effectively suppressed from entering a wafer W. Such pressure adjustments can be performed by FFUs (Fan Filter Units) and exhausting mechanisms of the individual stations. In that case, by interposing a punched metal between the FFU or the exhausting mechanism and each station, adjusting the number of holes of the punched metal and the size of each hole thereof, interposing a plurality of (for example, two) punched metals between the FFU or the exhausting mechanism and each station, or adjusting the positions of the punched metals (namely, their overlapping state), the pressures can be adjusted.

In the above-described embodiment, for example, the inspecting station S2 has the film thickness inspecting apparatuses 31 and the defect inspecting apparatuses 32 as inspecting portions. Alternatively, the inspecting station S2 may have only the defect inspecting apparatuses 32. In this case, the inspecting portions can be disposed in the coating and developing apparatus without need to change the process flow. In other words, in the conventional coating and developing apparatus, a transferring flow for a wafer W has been designated. With reference to FIG. 2, a wafer W that has not been exposed is transferred from the cassette station S1 to the aligner S5 (namely, from the left to the right in the X direction shown in FIG. 2). A wafer W that has been exposed is transferred from the aligner S5 to the cassette station S1 (namely, from the right to the left in the X direction shown in FIG. 2). Thus, in the case that an inspecting portion that performs a predetermined inspection after the developing process as with the defect inspecting apparatuses 32, when the inspecting station S2 is disposed midway between the cassette station S1 and the processing station S3, after the wafer W has been developed, a predetermined inspection can be performed without an inconsistency of the above-described transferring flow of the wafer W.

In the above-described example, the cassette station S1, the inspecting station S2, the processing station S3, and the interface station S4 can be connected and disconnected with each other. In addition, even if the inspecting station S2 is rotated by 180°, since the inspecting station S2 can access the cassette station S1 and the processing station S3, the flexibility of the layout is improved. In other words, in addition to the layout of which the inspecting station S2 is disposed midway between the cassette station S1 and the processing station S3, the layout of which the inspecting station S2 is disposed midway between the processing station S3 and the interface station S4 can be performed.

In such a structure, a predetermined inspection is performed for a wafer W that has been coated with resist. The structure is almost the same as that shown in FIG. 1 except that the position of the inspecting station S2 is different from that. In such a structure, between the processing station S3 and the inspecting station S2, the main transfer mechanism MA1 of the inspecting station S2 transfers a wafer W through the transferring portion 46 of the shelf unit R2 of the processing station S3. Between the inspecting station S2 and the interface station S4, the transfer mechanism A of the interface station S4 transfers a wafer W through the transferring portion 33 of the inspecting station S2 and the transferring opening 35 of the wall portion 34.

In addition, a wafer W is transferred in the following transferring flow. In other words, after the film thickness of bare silicon of a wafer W has been measured, the transfer mechanism 23 places the wafer W on the transferring portion 46 of the shelf unit R1 of the processing station S3. Thereafter, the wafer W is transferred in the path of the hydrophobic portion 45 of the shelf unit R, the cooling portion 44 of the shelf unit R, and the coating unit 42. The main transfer mechanism MA2 transfers the wafer W that has been coated with resist solution in the path of the heating portion 43 of the shelf unit R, the cooling portion 44 of the shelf unit R, and the transferring portion 46 of the shelf unit R2. Thereafter, the main transfer mechanism MA1 of the inspecting station S2 transfers the wafer W to predetermined inspecting apparatuses such as a film thickness inspecting apparatus 31 and a defect inspecting apparatuses 32. The inspecting apparatuses inspect the film thickness of the resist film, the coated irregularities of resist solution, the EBR cut width, and so forth of the wafer W.

The main transfer mechanism MA1 transfers the inspected wafer W to the transferring portion 33. The transfer mechanism A of the interface station S4 takes the wafer W from the transferring portion 33 and transfers the wafer W to the aligner S5. Thereafter, the exposed wafer is transferred in the path of the transfer mechanism A of the interface station S4, the transferring portion 33 of the inspecting station S2, the main transfer mechanism MA1, the transferring portion 46 of the shelf unit R2 of the processing station S3, the main transfer mechanism MA2, the heating portion 43 of the shelf unit R, the cooling portion 44 of the shelf unit R, the developing unit 41, the heating portion 43 of the shelf unit R, the cooling portion 44 of the shelf unit R, and the transferring portion 46 of the shelf unit R1.

In the example, the exposed wafer W may be transferred from the interface station S4 to the inspecting station S2. The inspecting station S2 inspects the exposed state of the wafer W. Thereafter, the wafer W may be transferred to the processing station S3.

Thus, in the example, since the inspecting station S2 can be connected and disconnected and can be disposed midway between the processing station S3 and the interface station S4, when the film thickness of bare silicon of a wafer W has been measured, after the resist solution is coated on the wafer W, a predetermined inspection can be performed for the wafer W without an inconsistency of the transferring flow of the wafer W. On the other hand, when the inspecting station S2 is disposed midway between the cassette station S1 and the processing station S3, if a predetermined inspection is performed after the resist solution is coated on a wafer W, it should be returned from the processing station S3 to the inspecting station S2. Thus, the wafer W cannot be transferred without an inconsistency of the transferring flow.

Figure 10:
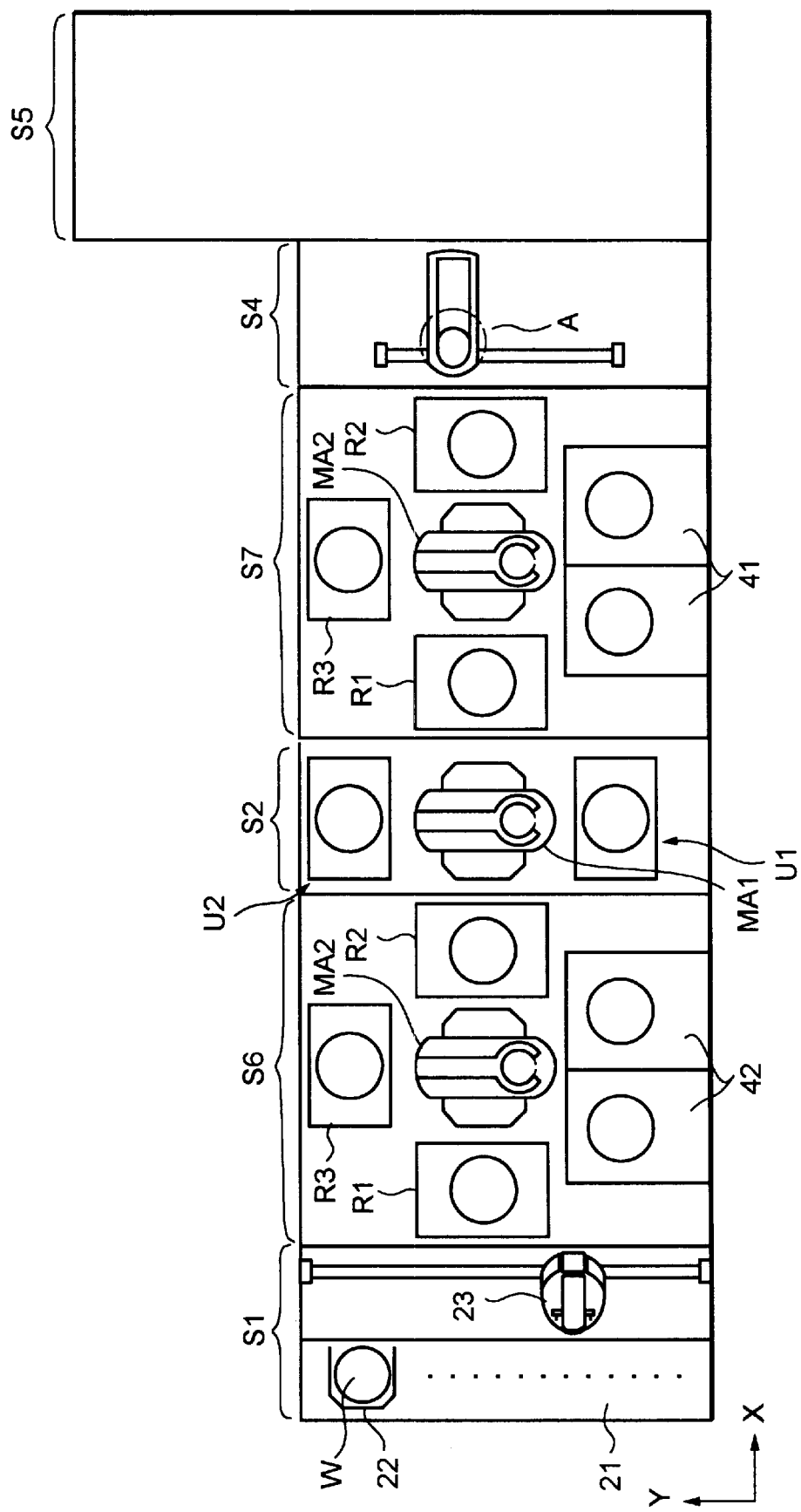
FIG. 10 is a schematic plan view showing a coating and developing apparatus according to still another embodiment of the present invention.

Next, with reference to FIG. 10, an example of the layout of which predetermined inspections are performed after a resist solution is coated and after a developing process is performed will be described. In the layout, a first processing station S6 that coats resist solution and a second processing station S7 that performs a developing process are disposed. The inspecting station S2 is disposed midway between the first processing station S6 and the second processing station S7. In other words, the cassette station S1, the first processing station S6, the inspecting station S2, the second processing station S7, the interface station S4, and the aligner S5 are laid out in succession.

Each of the first processing station S6 and the second processing station S7 is almost the same as the above-described processing station S3 except that processing units are composed of two coating units 42 as a first substrate processing portion and two developing units 41 as a second substrate processing portion. In addition, the structure of the inspecting station S2 shown in FIG. 10 is almost the same as the structure of the inspecting station S2 shown in FIG. 1. However, between the first processing station S6 and the inspecting station S2, the main transfer mechanism MA1 of the inspecting station S2 transfers a wafer W through a transferring portion 46 of a shelf unit R2 of the first processing station S6. Between the inspecting station S2 and the second processing station S7, the main transfer mechanism MA1 of the inspecting station S2 transfers a wafer W through a transferring portion 46 of the second processing station S7.

In such a structure, a wafer W is transferred in the following transferring flow. In other words, after the film thickness of bare silicon of the wafer W has been measured, the transfer mechanism 23 places the wafer W to a transferring portion 46 of a shelf unit R1 of the first processing station S6. Thereafter, the main transfer mechanism MA2 transfers the wafer W in the path of a hydrophobic portion 45 of the shelf unit R, a cooling portion 44 of the shelf unit R, and a coating unit 42. The main transfer mechanism MA2 transfers the wafer W that has been coated with resist solution in the path of a heating portion 43 of the shelf unit R, a heating portion 43 of the shelf unit R, and a transferring portion 46 of the shelf unit R2. Thereafter, the main transfer mechanism MA1 of the inspecting station S2 transfers the wafer W to predetermined inspecting apparatuses such as a film thickness inspecting apparatus 31 and a defect inspecting apparatuses 32 of the inspecting station S2.

The main transfer mechanism MA1 transfers the inspected wafer W to the transferring portion 46 of the shelf unit R1 of the second processing station S7. The main transfer mechanism MA2 of the second processing station S7 transfers the wafer W to the transfer mechanism A of the interface station S4 through the transferring portion 46. The transfer mechanism A transfers the wafer W to the aligner S5. The exposed wafer W is transferred in the path of the transfer mechanism A of the interface station S4, the transferring portion 46 of the shelf unit R2 of the second processing station S7, the main transfer mechanism MA2, the heating portion 43 of the shelf unit R, the cooling portion 44 of the shelf unit R, the developing unit 41, the heating portion 43 of the shelf unit R, the cooling portion 44 of the shelf unit R, and the transferring portion 46 of the shelf unit R1.

Thereafter, the main transfer mechanism MA1 of the inspecting station S2 transfers the wafer W to predetermined inspecting apparatuses such as a film thickness inspecting apparatus 31 and a defect inspecting apparatuses 32 of the inspecting station S2. The inspecting apparatuses perform the predetermined inspections for the wafer W.

The main transfer mechanism MA1 of the inspecting station S2 transfers the inspected wafer W to the transferring portion 46 of the shelf unit R2 of the first processing station S6. Thereafter, the main transfer mechanism MA2 transfers the wafer W to the original cassette 22 through the transferring portion 46 of the shelf unit R1.

In the example, since the inspecting station S2 can be connected and disconnected and can be disposed midway between the first processing station S6 and the second processing station S7, when the film thickness of bare silicon of a wafer W has been measured, after the resist solution is coated and the developing process is performed, a predetermined inspection can be performed without an inconsistency of the transferring flow.

Figure 11:
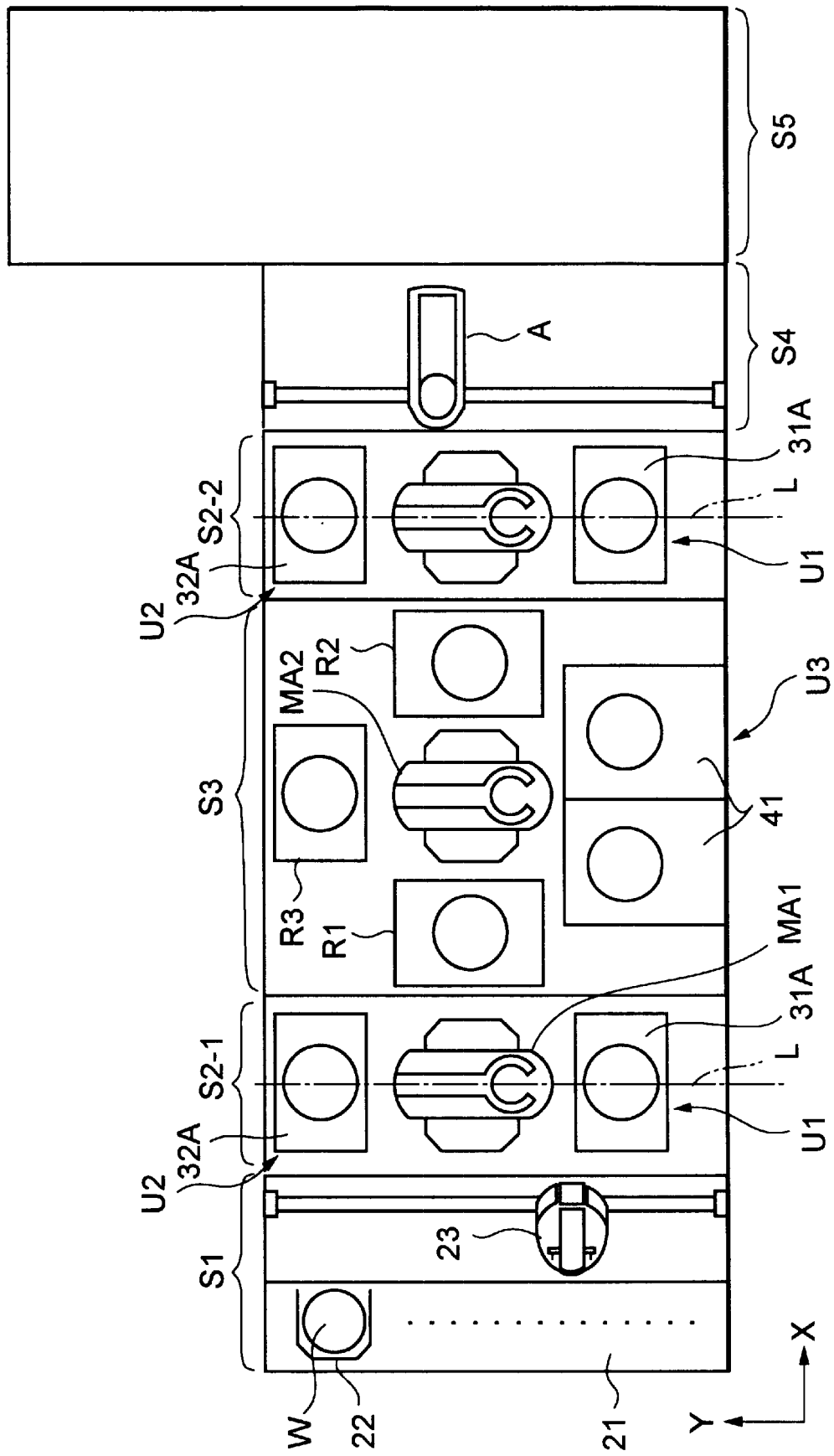
FIG. 11 is a schematic plan view showing a coating and developing apparatus according to yet another embodiment of the present invention.

Alternatively, according to the present invention, as shown in FIG. 11, two inspecting stations may be disposed. In this case, in the X direction, the cassette station S1, a first inspecting station S2-1, the processing station S3, a second inspecting station S2-2, the interface station S4, and the aligner S5 may be disposed in succession. In this case, after a film thickness inspecting apparatus 31 of the first inspecting station S2-1 measures the film thickness of bare silicon of a wafer W, the processing station S3 performs a hydrophobic process and a resist solution coating process for the wafer W. The second inspecting station S2-2 performs a predetermined inspection for the wafer W that has been coated with the resist solution.

Thereafter, the wafer W is transferred to the aligner S5 through the interface station S4. The aligner S5 exposes the wafer W. The exposed wafer W is transferred to the second inspecting station S2-2 through the interface station S4. The second inspecting station S2-2 inspects the exposed state of the wafer W. Thereafter, the wafer W is transferred to the processing station S3. Thereafter, the processing station S3 performs the developing process for the inspected wafer W. Thereafter, the first inspecting station S2-1 inspects the developed wafer W. In such a structure, since the wafer W is transferred in the path of the cassette station S1, the first inspecting station S2-1, the processing station S3, the second inspecting station S2-2, the aligner S5, the second inspecting station S2-2, the processing station S3, the first inspecting station S2-1, and the cassette station S1, the predetermined inspection can be performed without an inconsistency of the transferring flow of the wafer W of the cassette station S1, the aligner S5, and the cassette station S1.

Figure 12:
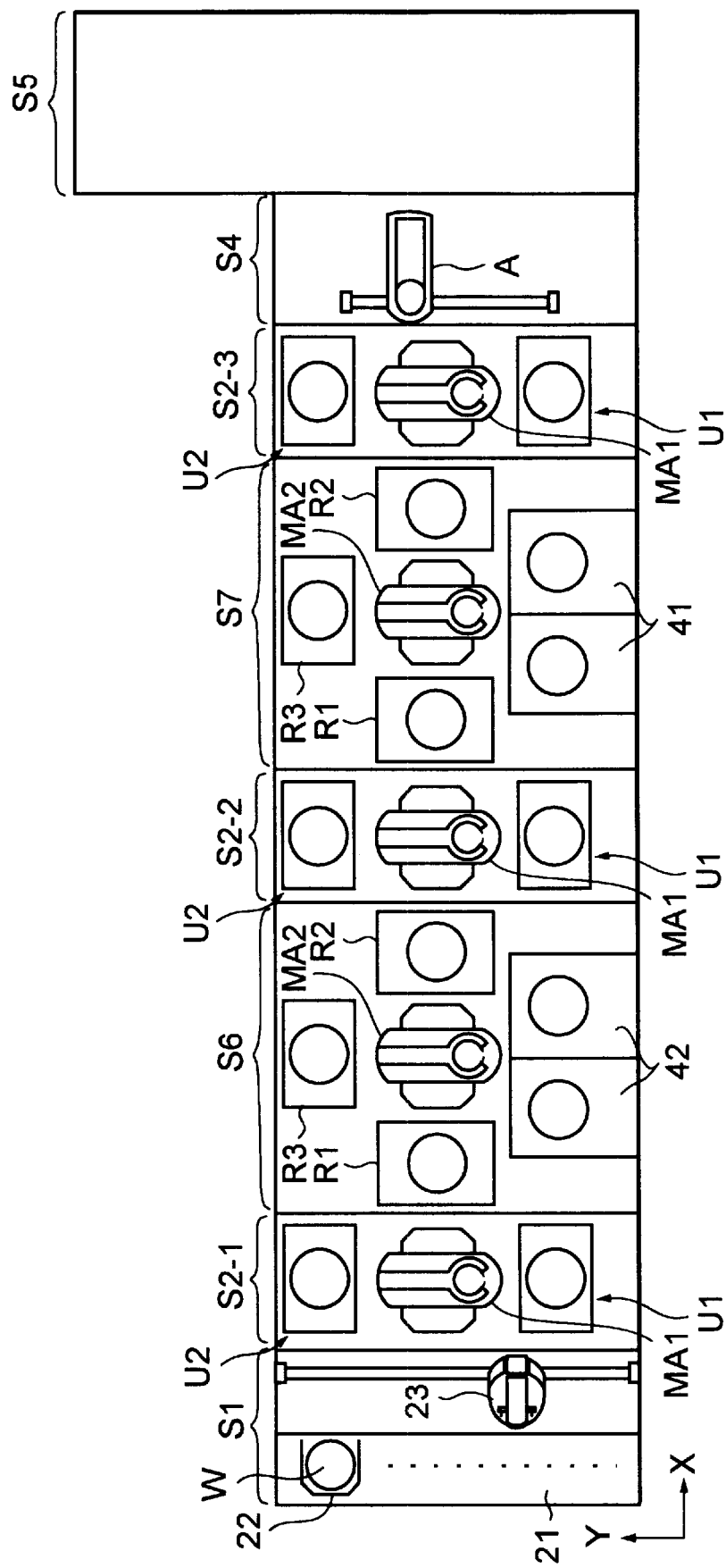
FIG. 12 is a schematic plan view showing a coating and developing apparatus according to another embodiment of the present invention.

In addition, according to the present invention, as shown in FIG. 12, three inspecting stations may be disposed. In the X direction, the cassette station S1, the first inspecting station S2-1, the first processing station S6 that performs a resist coating process, the second inspecting station S2-2, the second processing station S7 that performs a developing process, a third inspecting station S2-3, the interface station S4, and the aligner S5 may be disposed in succession.

In this case, after a film thickness inspecting apparatus 31 of the first inspecting station S2-1 measures the film thickness of bare silicon of a wafer W, the first processing station S6 performs a hydrophobic process and a resist solution coating process for the wafer W. The second inspecting station S2-2 (or the third inspecting station S2-3) performs a predetermined inspection for the wafer W that has been coated with resist solution.

Thereafter, the wafer W is transferred to the aligner S5 through the second processing station S7 and the interface station S4. The aligner S5 exposes the wafer W. The exposed wafer W is transferred to the third inspecting station S2-3 through the interface station S4. The third inspecting station S2-3 inspects the exposed state of the wafer W. Thereafter, the wafer W is transferred to the second processing station S7. The second processing station S7 develops the wafer W. Thereafter, the second inspecting station S22 (or the first inspecting station S2-1) performs a predetermined inspection for the wafer W. In such a structure, a predetermined inspection can be performed for the wafer W without an inconsistency of the transferring flow of the wafer W.

Figure 13:
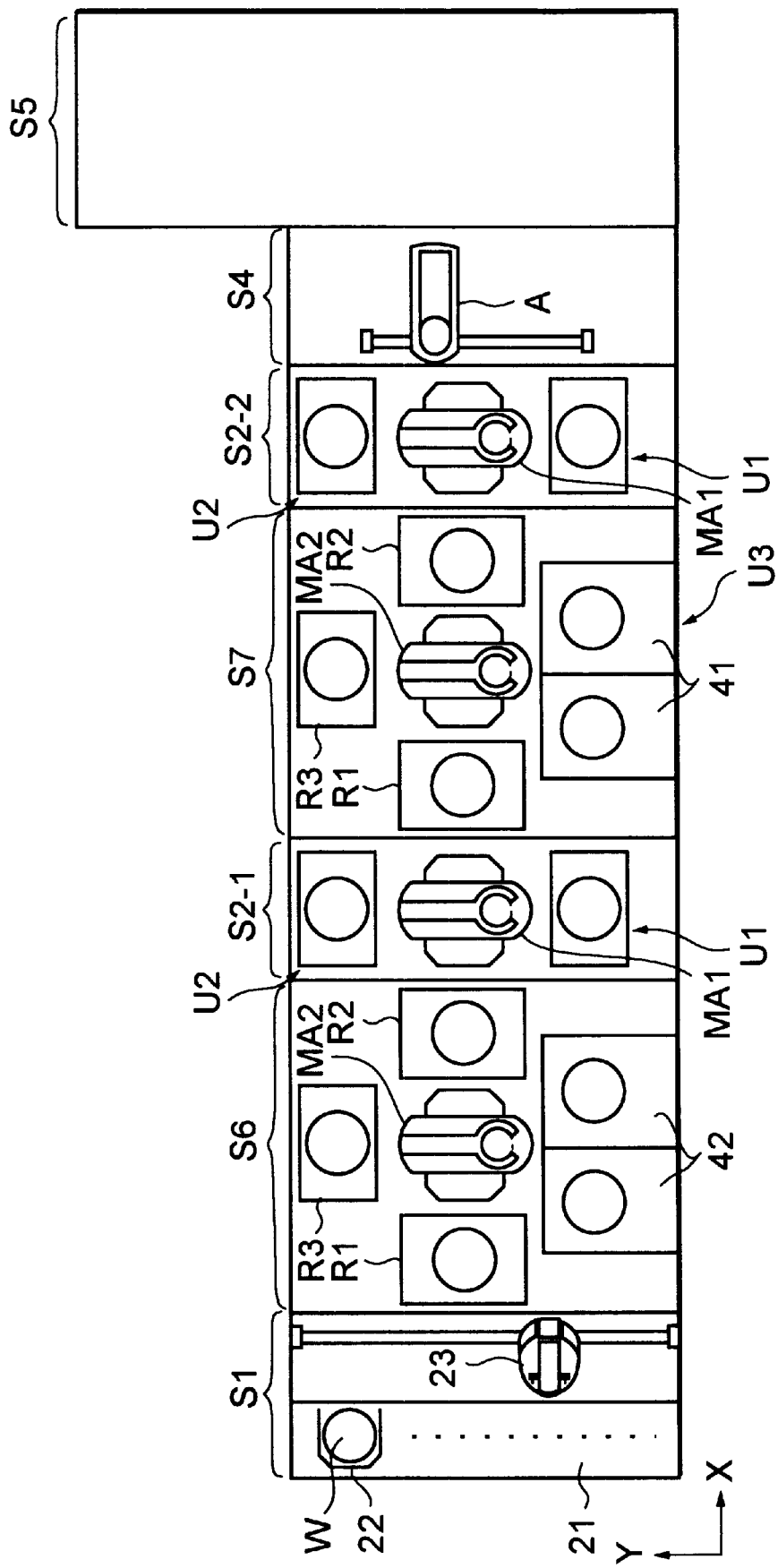
FIG. 13 is a schematic plan view showing a coating and developing apparatus according to still another embodiment of the present invention.

In addition, according to the present invention, as shown in FIG. 13, two inspecting stations may be disposed. In other words, in the X direction, the cassette station S1, the first processing station S6 that performs a resist coating process, the first inspecting station S2-1, the second processing station S7 that performs a developing process, the second inspecting station S2-2, the interface station S4, and the aligner S5 are disposed in succession.

In the case, after the film thickness of bare silicon of a wafer W is measured, the first processing station S6 performs a hydrophobic process and a resist solution coating process for the wafer W. The first inspecting station S2-1 (or the second inspecting station S2-2) performs a predetermined inspection for the wafer W that has been coated with resist.

Thereafter, the wafer W is transferred to the aligner S5 through the second processing station S7 and the interface station S4. The aligner S5 exposes the wafer W. The exposed wafer W is transferred to the second inspecting station S2-2 through the interface station S4. The second inspecting station S2-2 inspects the exposed state of the wafer W. Thereafter, the wafer W is transferred to the second processing station S7. The second processing station S7 develops the wafer W. Thereafter, the first inspecting station S2-1 performs a predetermined inspection for the developed wafer W. In such a structure, a predetermined inspection can be performed for a wafer W without an inconsistency of the transferring flow of the wafer W.

Thus, according to the present invention, when the cassette station S1, the processing station S3, and the inspecting station S2 are disposed and the inspecting station S2 inspects the processed states of the resist solution coating process and the developing process for the wafer W processed at processing station S3, those stations can be freely laid out.

In this case, the number of inspecting apparatuses of the inspecting station S2 may be one or more. The types of the inspecting apparatuses may be apparatuses that inspect particles, EBR widths, WEE widths, coated irregularities, developed irregularities, uncoated portion, undeveloped portion, line widths, exposed focus deviation, and so forth as well as a film thickness measuring apparatus and a defect measuring apparatus. In addition, as a holding portion, the space of the inspecting station may be used for a chemical unit C and/or an electric unit E depending on the type of a film formed on a wafer W.

In addition, the main transfer mechanism MA1 may not be disposed in the inspecting station S2. In this case, in the inspecting station S2, a wafer W may be transferred by the transfer mechanism 23 of the cassette station S1 and the main transfer mechanism MA2 of the processing station S3.

In addition, when the inspecting station S2 can be freely connected to and disconnected from the cassette station S1, the processing station S3, and so forth, it is not necessary to partition the inspecting station S2 with the wall portion 34. In addition, the atmospheric temperature and humidity in the inspecting station S2 may not be always adjusted to predetermined values.

In addition, instead of a hydrophobic process on the front surface of a wafer W, a reflection protecting film may be formed thereon. The substrate may be a glass substrate for a liquid crystal display instead of a wafer. When the reflection protecting film is formed, an inspecting unit that detects the reflection ratio is disposed in the inspecting station. Before a wafer W is exposed, the reflection ratio is detected. The information of the reflection ratio is supplied to the aligner. The aligner controls the exposing process corresponding to the information so that the wafer W is constantly exposed. For example, the aligner controls the exposure time and exposure intensity corresponding to the information.

Thus, according to the present invention, since the substrate processing apparatus is structured by connecting an inspecting station having an inspecting portion to a processing station, the operation from a substrate process to an inspection can be simplified and performed in a short time.

Next, another embodiment of the present invention will be described.

Figure 14:
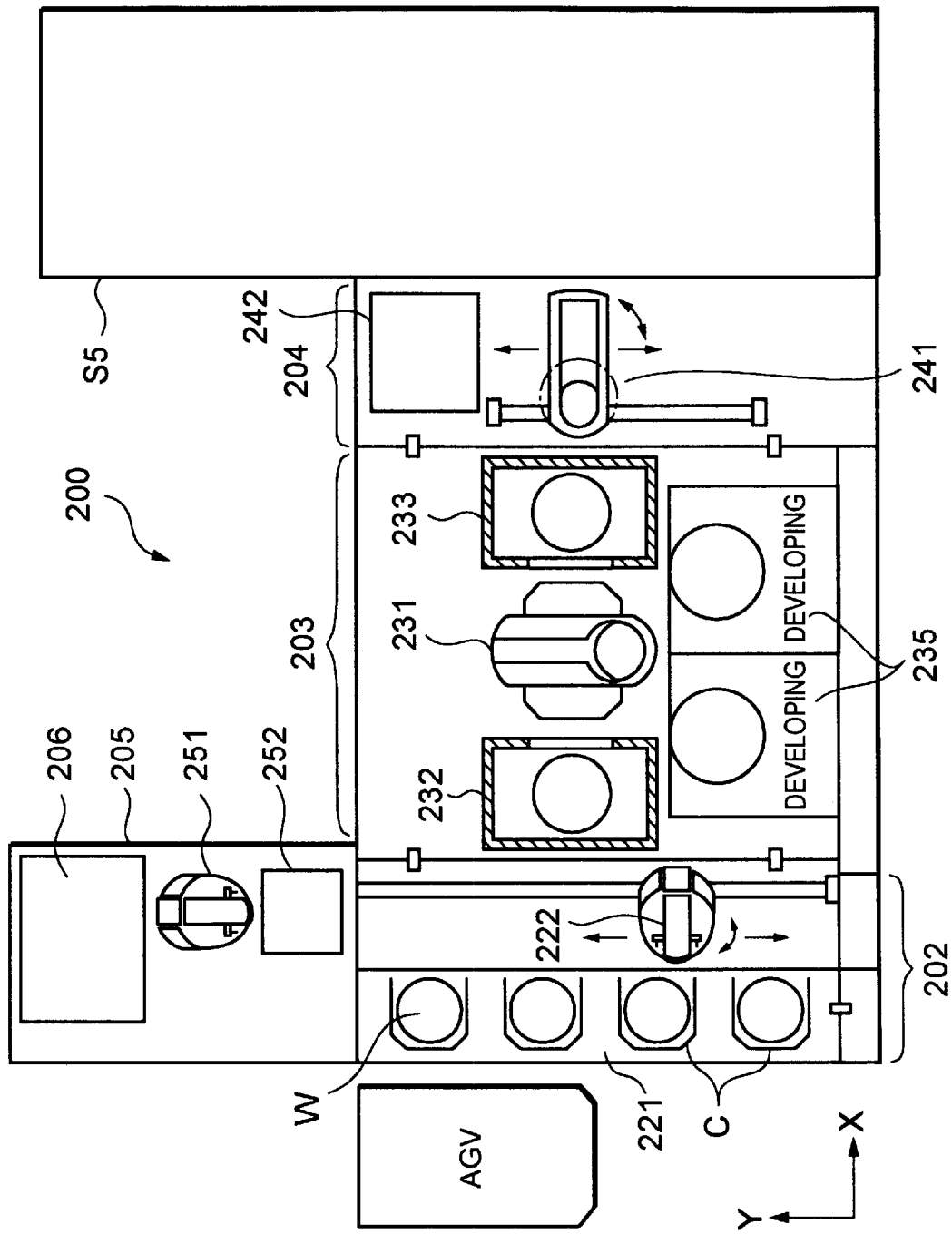
FIG. 14 is a schematic plan view showing the overall structure according to another embodiment of the present invention.
Figure 15:
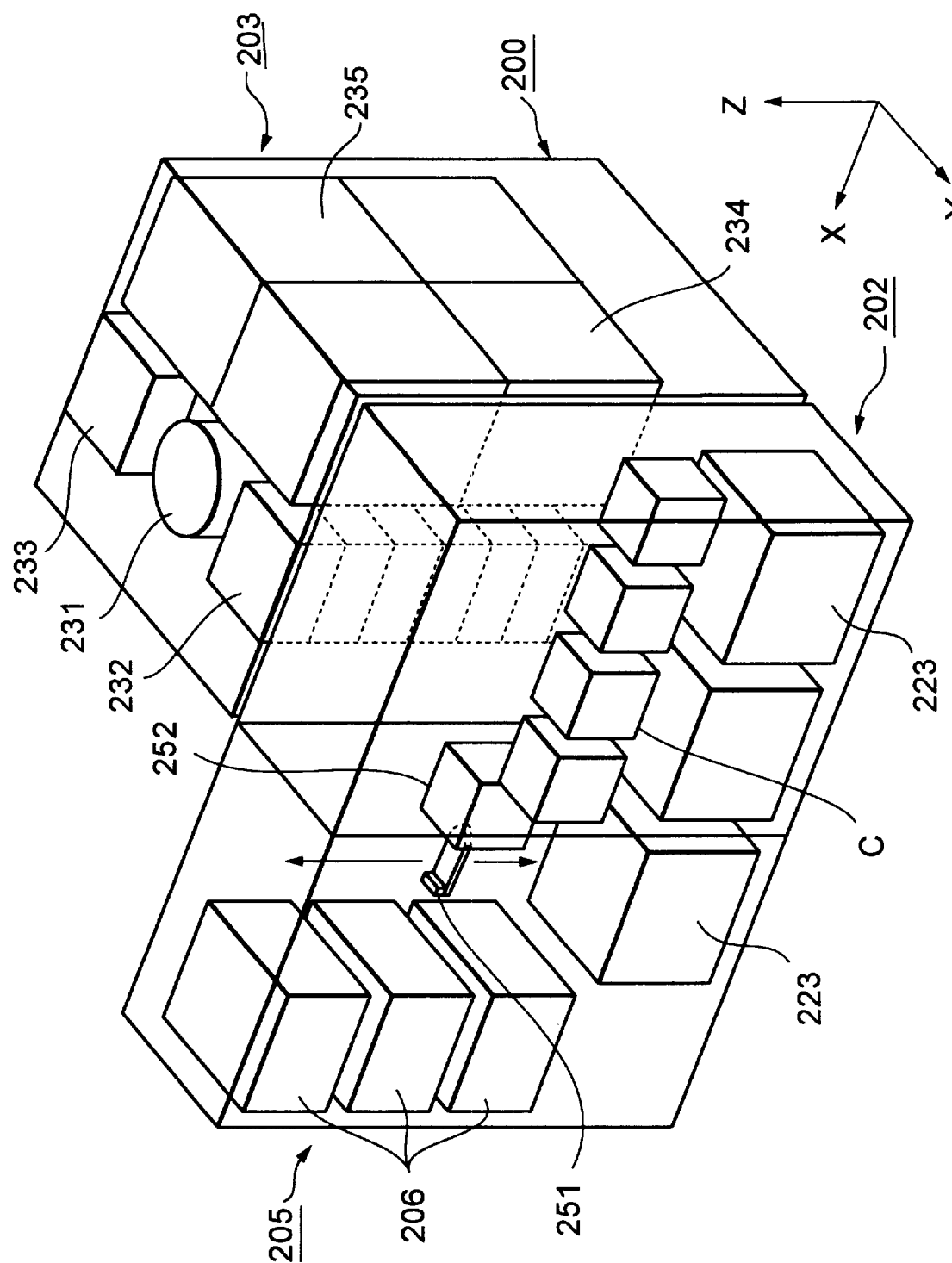
FIG. 15 is a schematic perspective view showing the embodiment shown in FIG. 14.

FIG. 14 is a schematic plan view showing the interior of a coating and developing apparatus 200 according to an embodiment of the present invention and the overall structure of a pattern forming system of which the aligner S5 is connected to the coating and developing apparatus 200. FIG. 15 is a schematic perspective view showing the coating and developing apparatus 200. The coating and developing apparatus 200 is composed of a carrier station 202, a processing station 203, an interface station 204, and an inspecting station 205.

The carrier station 202 has a carrier loading/unloading portion (carrier stage) 221 and a first transfer mechanism 222. The carrier stage 221 loads and unloads a wafer carrier as a transferring vessel (hereinafter referred to as carrier) C to the coating and developing apparatus 200. A carrier C contains a plurality of wafers W (for example, 25 substrates) in a shelf shape. The carrier stage 221 aligns for example four carriers C at predetermined positions in the X direction. The first transfer mechanism 222 is a first transferring portion that transfers a wafer W to and from a carrier C placed on the carrier stage 221. The first transfer mechanism 222 has an arm that can be moved forward and backward against a pedestal that can be moved in the X and Z directions and rotated around the vertical direction. In the example, the carrier stage 221 also functions as an external carrier holding portion that loads a carrier that contains a wafer that has been processed (namely, on which a resist pattern has been formed) by an external apparatus.

Figure 16:
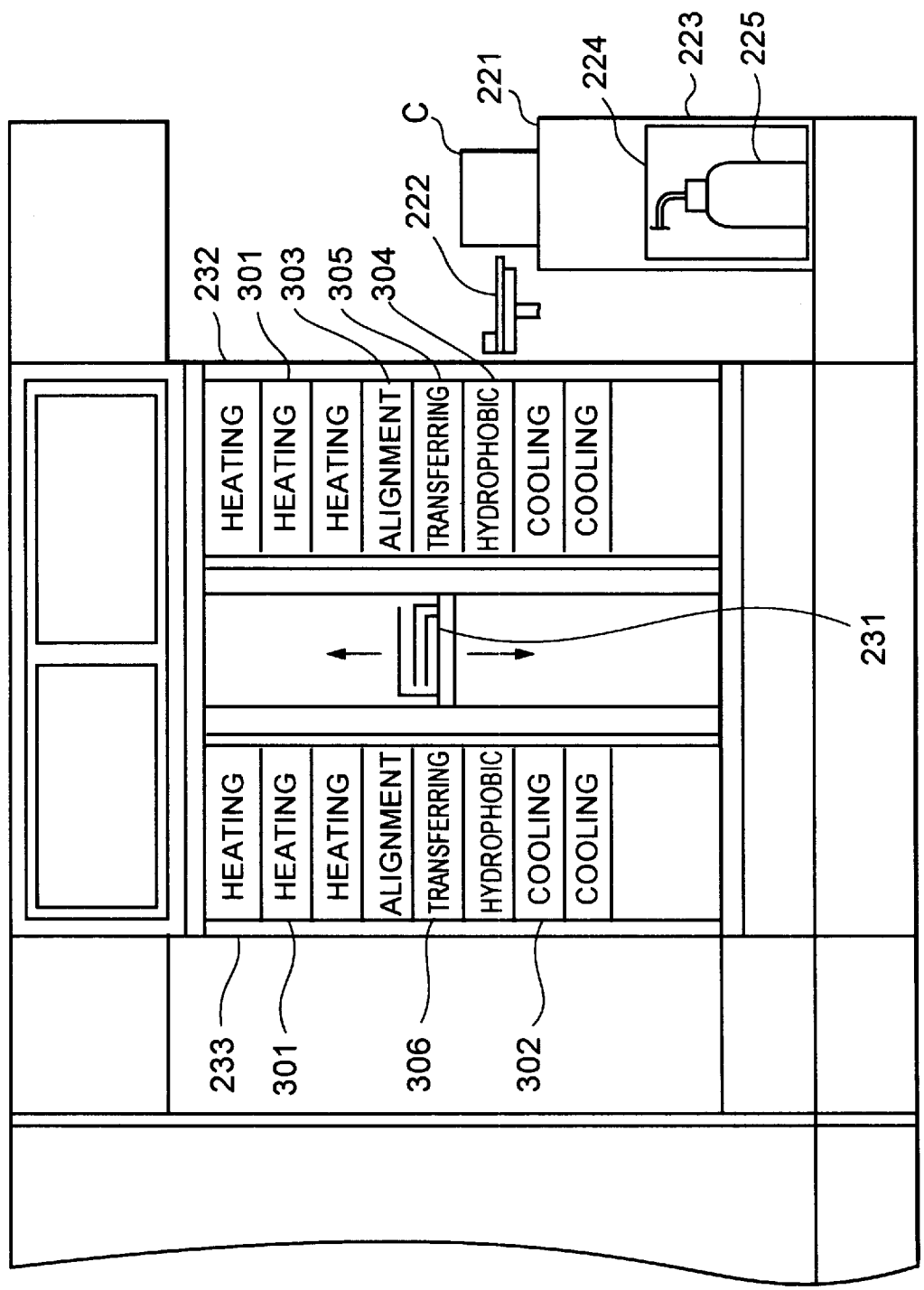
FIG. 16 is a schematic, vertical side view showing a part of the embodiment shown in FIG. 14.

The processing station 203 is disposed adjacent to the carrier station 202 in the Y direction. The processing station 203 has a wafer transferring portion 231 (hereinafter referred to as main transfer mechanism). The main transfer mechanism 231 is disposed at a center position of the processing station 203. When the main transfer mechanism 231 is viewed in the Y direction, shelves 232 and 233 are disposed on the front and rear sides, respectively. Each of the shelves 232 and 233 has a plurality of units disposed in the vertical direction. As shown in FIG. 16, each shelf has a heating unit 301, a cooling unit 302, an alignment unit 303, a hydrophobic unit 304, transferring units 305 and 306, and so forth. The heating unit 301 heats a wafer W. The cooling unit 302 cools a wafer W. The alignment unit 303 aligns a wafer W. The hydrophobic unit 304 performs a hydrophobic process for a wafer W. Each of the transferring units 305 and 306 has a stage on which a wafer W is transferred. The units of the shelves 232 and 233 shown in FIG. 16 are just examples.

When viewed from the carrier station 202 to the processing station 203, on the right of the main transfer mechanism 231, two coating unit 234 that are coating portions as lower units and two developing units 235 that are developing portions as upper units are disposed. The main transfer mechanism 231 can be elevated, rotated around the vertical axis, and moved forward and backward. The main transfer mechanism 231 transfers a wafer W between each unit of the shelves 232 and 233 and each of the coating units 234 and developing units 235.

Each coating unit 234 holds a wafer W with for example a spin chuck, rotates the wafer W, supplies a resist at a center portion of the wafer W, and spreads the resist on the wafer W using centrifugal force so as to coat the resist on the wafer W. The developing unit 235 coats developing solution on the front surface of the exposed wafer W so as to develop the wafer W.

The interface station 204 comprises a transfer mechanism 241, a periphery exposing unit 242, and a wafer holding shelf (not shown). The transfer mechanism 241 transfers a wafer W between the transferring unit 306 of the shelf 233 and the aligner S5. The periphery exposing unit 242 exposes the peripheral portion of a wafer W that has been exposed. The wafer holding shelf buffers a wafer W. The periphery exposing unit 242 removes resist from an exposed wafer W with developing solution to prevent resist on the periphery of the wafer W from peeling off (as particles). The periphery exposing unit 242 has an X-Y stage and an aligner. The X-Y stage can hold a wafer W and can be moved in the X and Y directions.

The inspecting station 205 is disposed adjacent to the carrier station 202 in the X direction. The inspecting station 205 has a plurality of inspecting portions 206 that inspect a processed wafer W. The inspecting portions 206 are disposed in the vertical direction. The inspecting portions 206 inspect coated state of resist on a wafer W, exposed state of an exposed wafer W, and an exposed state on the front surface f a developed wafer W. In reality, the inspecting portions 206 inspect for example line widths of resist pattern, matching of resist pattern and base film, developing defects, coated irregularities of resist, and exposed state.

In the example, there are three stages of inspecting portions 206. However, the number of stages of inspecting portions 206 is not limited to three as long as it is one or more. In the following description, each inspecting portion is referred to as pattern inspecting portion. Each pattern inspecting portion 206 has a structure as shown in FIG. 4.

The inspecting station 205 has an auxiliary transfer mechanism 251 and an intermediate holding portion 252.

The auxiliary transfer mechanism 251 is an auxiliary transferring portion that transfers a wafer W to and from each pattern inspecting portion 206. The auxiliary transfer mechanism 251 is composed of a pedestal and an arm. The pedestal can be moved in the Z direction and rotated around the vertical axis. The arm can be moved forward and backward. The intermediate holding portion 252 temporarily holds a wafer W when it is transferred between the auxiliary transfer mechanism 251 and the first transfer mechanism 222 of the carrier station 202. The inspecting station 205 is fully surrounded with a housing. Casters are disposed at a bottom portion of the inspecting station 205. Thus, the inspecting station 205 can be connected to and disconnected from the carrier station 202.

Figure 17:
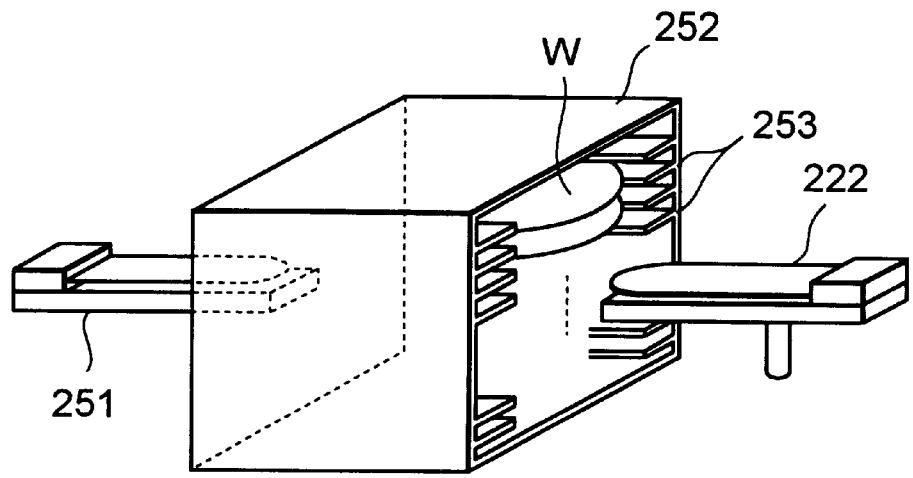
FIG. 17 is a perspective view showing an example of an intermediate holding portion according to the embodiment.

As shown in FIG. 17, the intermediate holding portion 252 has many shoulder portions 253 that hold many (for example, 25) wafers W. In addition, the intermediate holding portion 252 has two open sides from which the transfer mechanism 222 and the auxiliary transfer mechanism 251 access (transfer) a wafer W. Since the intermediate holding portion 252 can hold many wafers W, when the throughput of the processing station 203 is higher than the throughput of the inspecting station 205, the intermediate holding portion 252 functions as so-called a buffer. Thus, the total throughput of the apparatus can be prevented from being affected by the throughput of the inspecting station 205.

Figure 18:
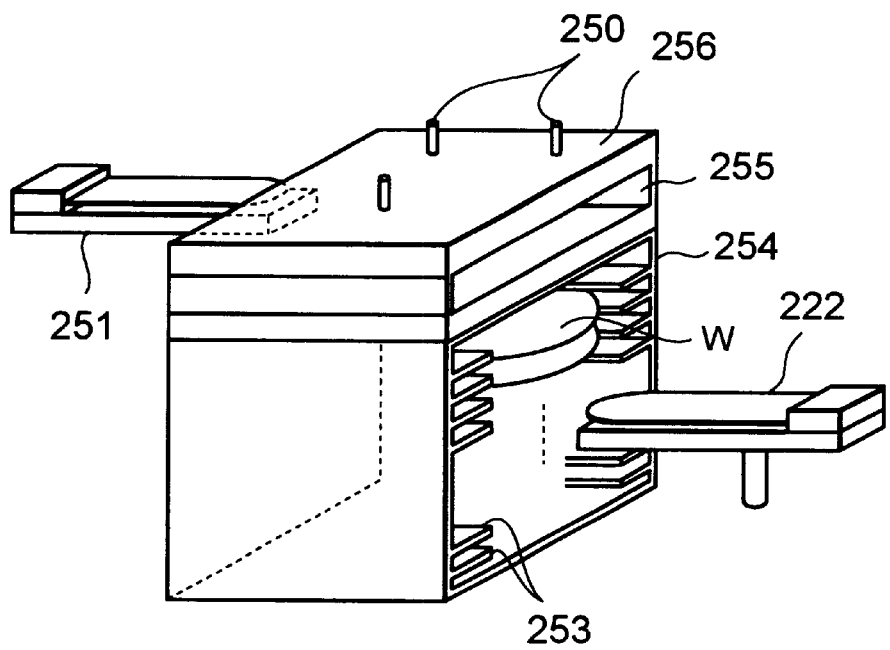
FIG. 18 is a perspective view showing an example of an intermediate holding portion according to the embodiment.

Although the transfer mechanism 222 and the auxiliary transfer mechanism 251 can access a wafer W at any stage of the intermediate holding portion 252, to do that, it is necessary that the transfer mechanism 222 and the auxiliary transfer mechanism 251 to be informed at what stages wafers W are held. Thus, mapping sensors composed of light reflection sensors should be disposed in the transfer mechanism 222 and the auxiliary transfer mechanism 251. Alternatively, as shown in FIG. 18, a two-staged holding table may be disposed in a multi-staged holding table 254. In this case, the lower-stage side is used as a loading stage 255 that dedicatedly transfers a pre-inspected wafer W from the transfer mechanism 222 to the auxiliary transfer mechanism 251. The upper-stage side is used as an unloading stage 256 that dedicatedly transfers an inspected wafer W from the auxiliary transfer mechanism 251 to the transfer mechanism 222. In reality, a wafer W is placed on three protrusions 250. Below the three protrusions 250, spaces for the arms 222 and 251 are formed. In such a structure, since the positions at the auxiliary transfer mechanism 251 takes a wafer W and leaves it are designated, the auxiliary transfer mechanism 251 does not need the mapping sensors.

On the lower side of the loading/unloading station 221 of the carrier station 202 and at a bottom portion of the inspecting station 205, as shown in FIGS. 15 and 16, for example, a total of three chemical units 223 are disposed. Each chemical unit 223 has a housing 224 (see FIG. 16) and a vessel 225. The housing 224 has two doors that can be opened and closed in the near side and far side in the Y direction. The vessel 225 is disposed in the housing 224. The vessel 225 contains resist solution used for the coating unit 234 or developing solution used for the developing unit 235. In addition, the housing 224 may contain a pump, a filter, and a valve disposed in the supply path of resist solution (developing solution). The coating and developing apparatus is designated in a size as small as possible. Therefore, it is difficult to prepare a space for the vessel that contains process solution. Consequently, the vessel is disposed outside the apparatus. Thus, it is advantageous to dispose the vessel at the bottom of the inspecting station 205 from a view point of the effective use of the space in the loading/unloading stage 221 or the inspecting station 205.

Figure 19:
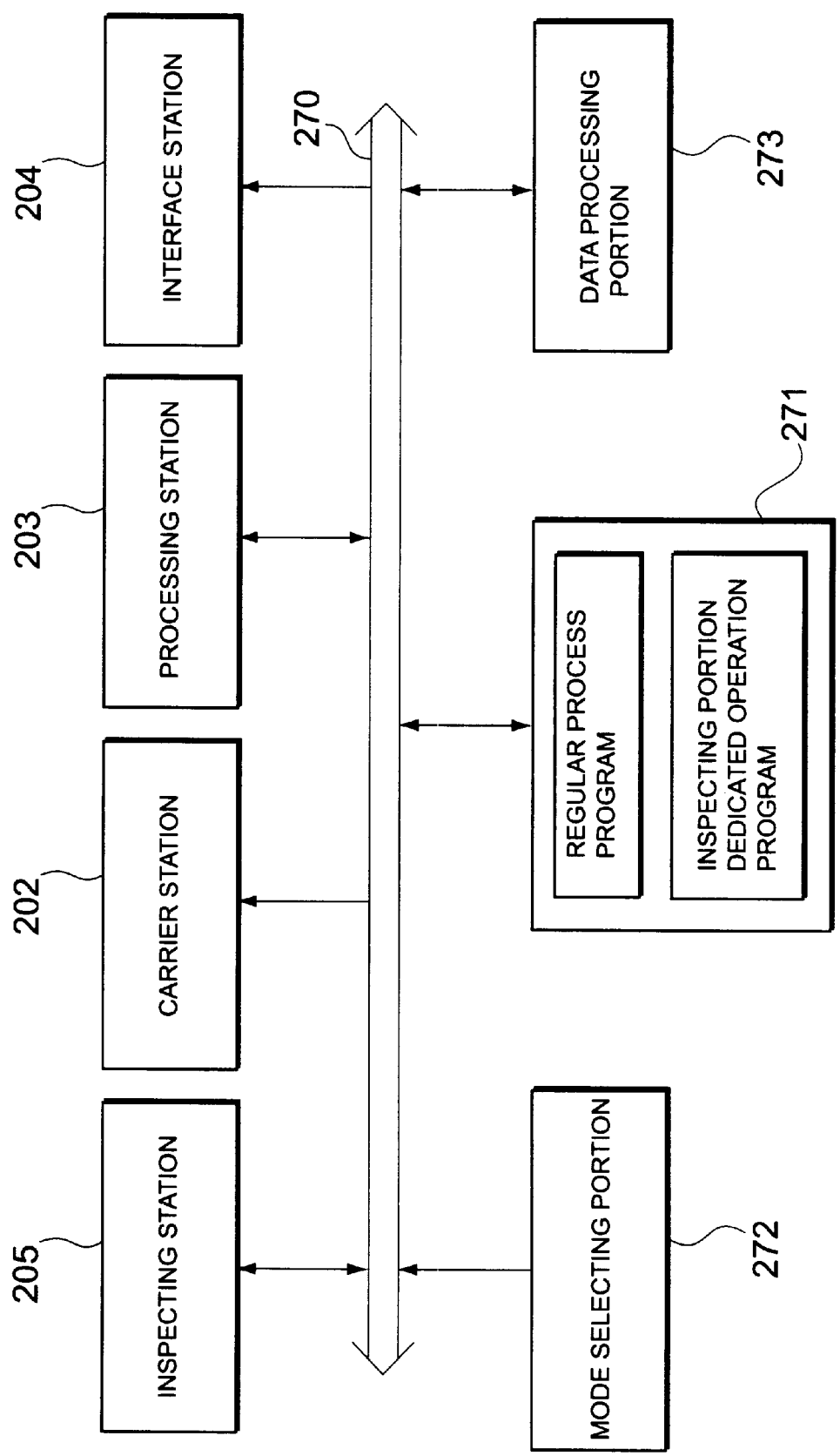
FIG. 19 is a block diagram showing a controlling system of the embodiment.

Next, with reference to FIG. 19, a controlling system of the coating and developing apparatus according to the embodiment will be described. In FIG. 19, reference numeral 271 represents a program storing portion. The program storing portion 271 stores a regular process program and an inspecting portion dedicated operation program. Reference numeral 272 represents a mode selecting portion. The mode selecting portion 272 selects the regular operation mode or inspecting portion dedicated operation mode. The mode selecting portion 272 is disposed in for example an operation panel portion on the outer surface of the coating and developing apparatus. When the regular operation mode is selected, a data processing portion 273 reads the regular process program and thereby the stations 202, 203, 204, and 205 operate. When the inspecting portion dedicated operation mode is selected, the data processing portion 273 reads the inspecting portion dedicated operation program and thereby the carrier station 202 and the inspecting station 205 operate. In FIG. 19, reference numeral 270 represents a bus.

Next, the operation of the embodiment will be described. First of all, it is assumed that the regular operation mode has been selected by the mode selecting portion 272. A carrier C that contains for example 25 wafers W on which a resist pattern is formed is transferred from the outside of the apparatus to the carrier loading/unloading portion 221. The transfer mechanism 222 takes a wafer W from the carrier C. The wafer W is transferred from the transfer mechanism 222 to the main arm 222 through the transferring unit 305 of the shelf 232. The wafer W is successively transferred to each processing unit of the shelf 232 (or 233). The individual units perform a hydrophobic process, a cooling process, and so forth for the wafer W. Thereafter, the wafer W is transferred to the coating unit 234. The coating unit 234 coats resist on the wafer W. Thereafter, a heating process is performed for the wafer W. Thereafter, the wafer W is transferred from the transferring unit 306 of the shelf 233 to the aligner S5 through the interface station 204.

The wafer W exposed in the aligner S5 is returned to the processing station 203 in the reverse path. The main transfer mechanism 231 transfers the wafer W to the developing unit 235. The developing unit 235 develops the wafer W. In more detail, before the developing process is performed for the wafer W, a heating process and a cooling process are performed for the wafer W. The developed wafer W is transferred to the transfer mechanism 222 in the reverse path. Thereafter, the wafer W is transferred to the intermediate holding portion 252. At that point, when one of the inspecting portions 206 is free, the wafer W held in the intermediate holding portion 252 is transferred to the pattern inspecting portion 206 by the auxiliary transfer mechanism 251. In contrast, when all the pattern inspecting portions 206 are not free, the auxiliary transfer mechanism 251 waits until one of them becomes free. After the wafer W that has been inspected is transferred to the intermediate holding portion 252, the wafer W held in the intermediate holding portion 252 is transferred to the pattern inspecting portion 206. The inspecting portion 206 inspects pattern line widths, matching of pattern and base film, developed irregularities, develop defects, and so forth for the wafer W. When the inspected result of the pattern is successful, the wafer W is returned to the original carrier C through the auxiliary transfer mechanism 251, the intermediate holding portion 252, and the transfer mechanism 222. When the inspected result of the pattern is not successful, the inspecting portion 206 marks the wafer W as an NG wafer. Thereafter, the NG wafer W is returned to the original carrier C or an NG water holding portion (not shown) in the inspecting station 205 or the carrier station 202. In the embodiment, the case that the front surface of a wafer W is inspected after a developing process was described. However, the inspections can be performed before a coating process, after a coating process, or after an exposing process.

Next, the case that the inspecting portion dedicated operation mode is selected by the mode selecting portion 272 and the apparatus is operated with the inspecting portion dedicated operation program will be described. The inspecting portion dedicated operation mode is selected when the resist process is not performed for a wafer W (namely, the processing station 203 is not used) or when a maintenance operation for the processing station 203, the interface station 204, or the aligner S5 is performed. In the mode, a carrier C that contains a wafer W that is inspected is transferred from the outside of the coating and developing apparatus to the loading/unloading stage 221. The position at which the carrier C is loaded may be limited to the position of the carrier C closest to the inspecting portions 206. Alternatively, the carrier C may be placed at one of four positions of the loading/unloading stage 221. When the carrier C is transferred to the loading/unloading stage 221, the transfer mechanism 222 takes a wafer W from the carrier C and transfers the wafer W to a pattern inspecting portion 206 in the above-described manner. In this case, using the carrier station 202, only the inspecting station 205 is operated.

According to the embodiment, since the inspecting station 205 is adjacently connected to the carrier station 202 and a developed wafer W is transferred to a pattern inspecting portion 206 in line, the pattern of the wafer W can be inspected in the coating and developing apparatus without need to convey the wafer W to the outside of the apparatus. Thus, the throughput of the apparatus is improved. In addition, the inspected result of the pattern can be displayed using the operating portion of the coating and developing apparatus. Thus, the recipes of the aligner S5, the developing unit 235, and so forth can be quickly reviewed.

Since the inspecting portion dedicated operation program is provided as well as the regular process program, while the coating process and the developing process are not performed (for example, when a maintenance operation is performed for the processing station 203), using the transfer mechanism 222 of the carrier station 202, only a pattern inspecting portion 206 can be operated. Thus, the pattern of a wafer that is brought from the outside of the apparatus can be inspected. At that point, since a carrier C that contains the wafer W is loaded and unloaded by the loading/unloading stage 221, the carrier can be transferred by an automatic transferring robot (or automatic guided vehicle AGV).

When the length in the X direction of the coating and developing apparatus is larger than the length in the X direction of the aligner S5 and the side on which the coating unit 234 is disposed is arranged, as shown in FIG. 14, on the opposite side, the aligner S5 protrudes. The area beside the coating and developing apparatus corresponding to the protruded area becomes an unused extra space. However, when the inspecting station 205 is disposed on the protruded side of the aligner S5, the unused extra space can be effectively used.

Sometimes, the film thickness of resist of a final wafer at intervals of a predetermined number of wafers may be inspected. Alternatively, the film thickness of resist of a monitor wafer may be periodically inspected. In addition, the film thickness of a film such as poly-silicon or silicon oxide on a wafer W may be inspected. For this purpose, a film thickness measuring portion is integrated with the periphery exposing unit 242. Alternatively, the film thickness measuring portion may be integrated with a pattern inspecting portion 206 or disposed in the inspecting station 205. When the film thickness measuring portion is integrated with the inspecting portion 206, a film thickness sensor that receives spectrum of reflected light from a wafer W may be disposed beside the CCD camera 120 shown in FIG. 4.

Figure 20:
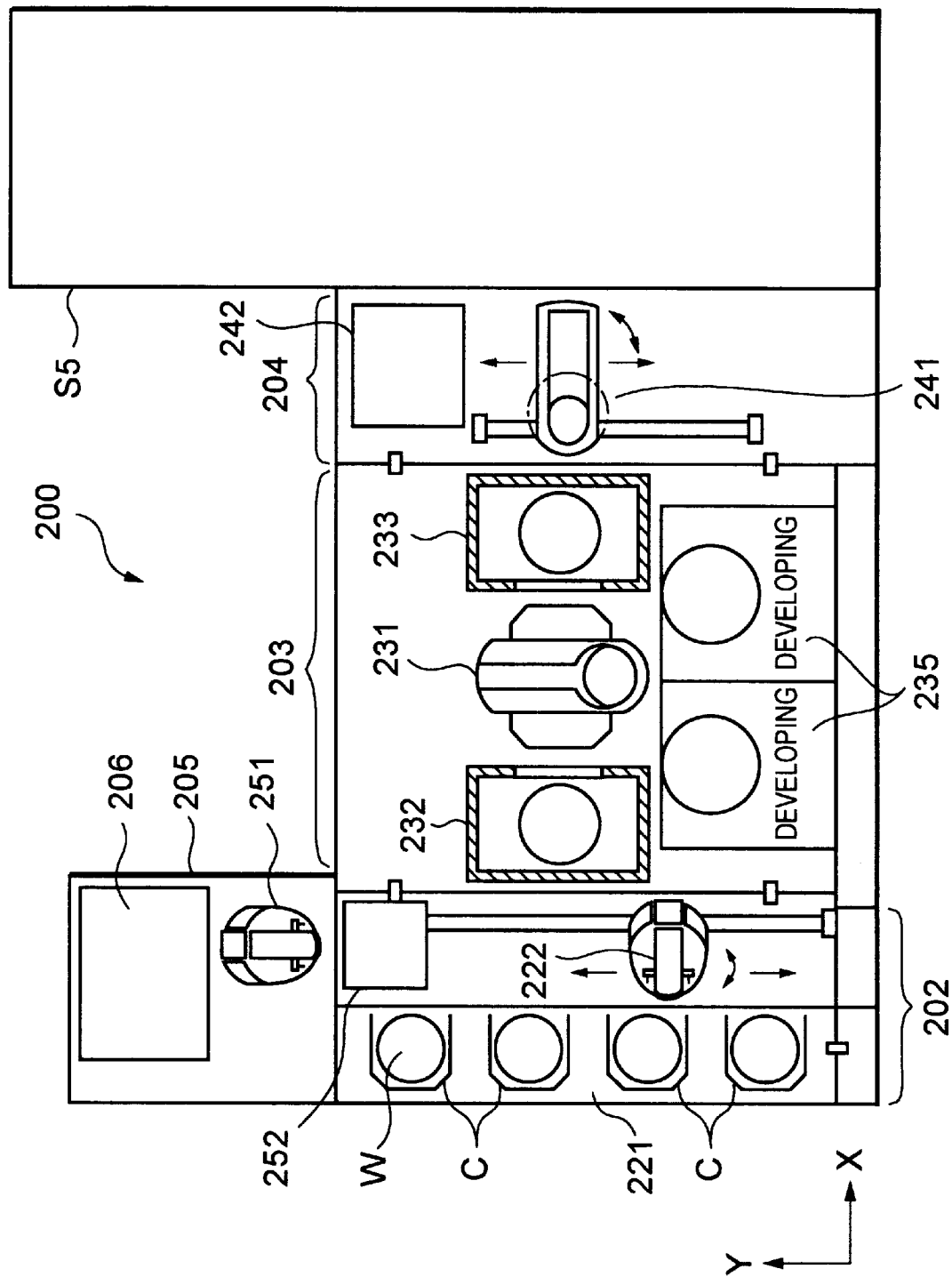
FIG. 20 is a schematic plan view showing the overall structure of another embodiment of the present invention.
Figure 21:
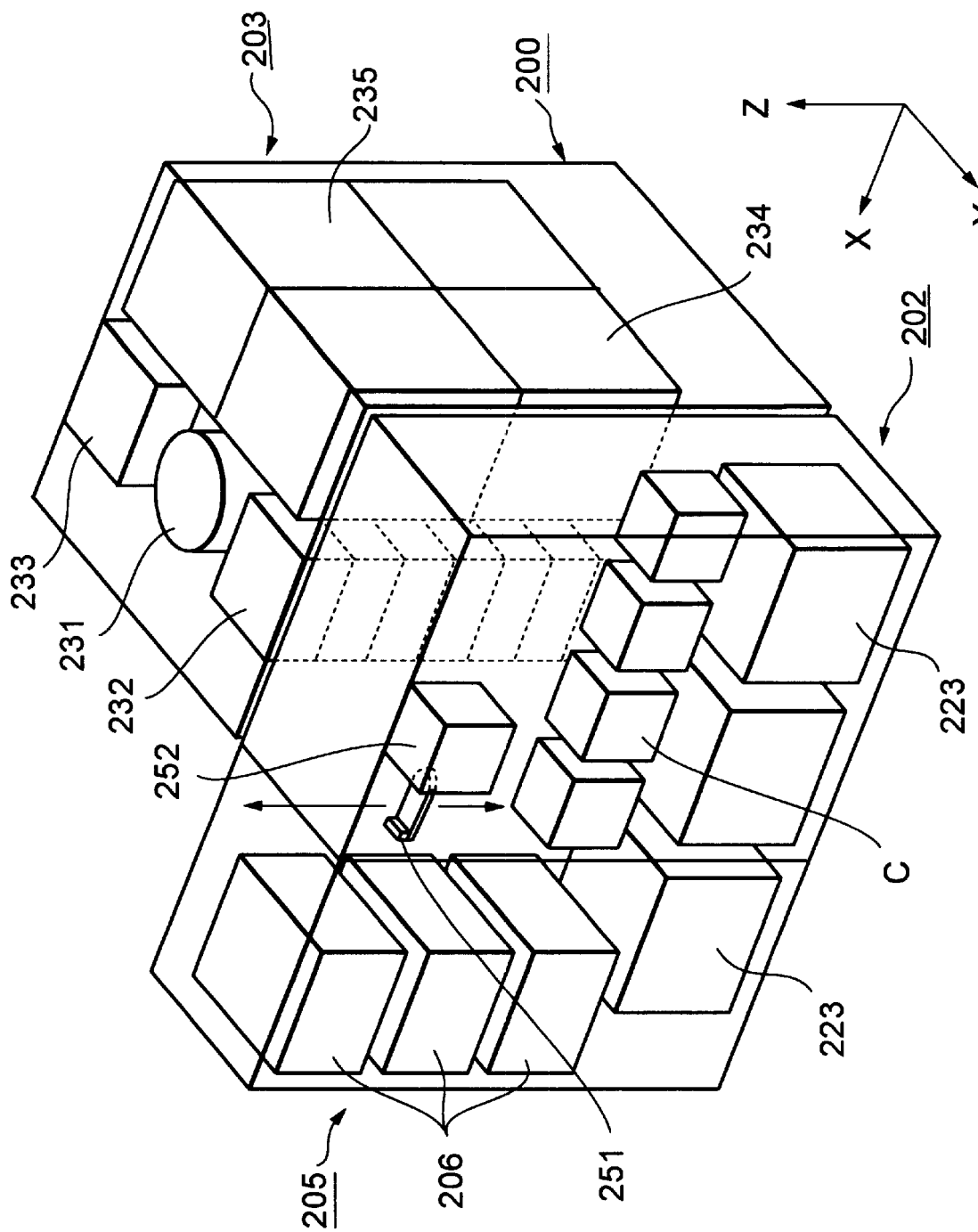
FIG. 21 is a schematic perspective view showing the embodiment shown in FIG. 20.
Figure 22:
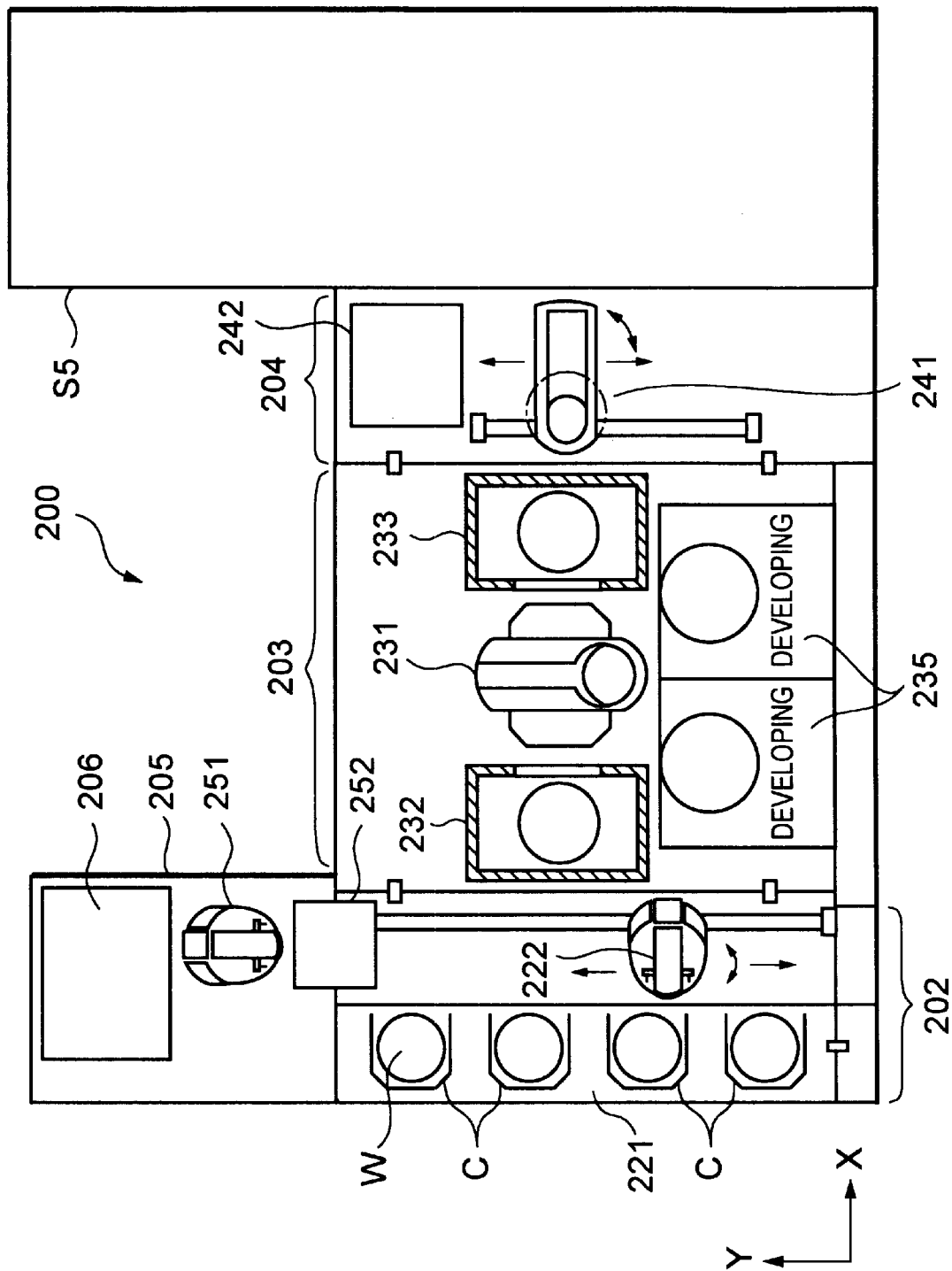
FIG. 22 is a schematic plan view showing the overall structure of another embodiment of the present invention.

Next, other embodiments of the present invention will be described. FIGS. 20 and 21 show an example of which the intermediate holding portion 252 disposed midway between the first transfer mechanism 222 and the auxiliary transfer mechanism 251 is disposed on the carrier station 202 side. In the example, the intermediate holding portion 252 is disposed at a position higher than the arrangement of carries C on the loading/unloading stage 221 by one stage. In this case, the transfer mechanism 222 takes a wafer W whose pattern has been inspected from the intermediate holding portion 252. Thereafter, the first transfer mechanism 222 lowers and transfers the wafer W to a carrier C. In this case, the length in the Y direction of the inspecting station 205 can be shortened. FIG. 22 shows an example of which the intermediate holding portion 252 is disposed at the same height as the arrangement of carriers C on the loading/unloading stage 221, the intermediate holding portion 252 being disposed between the carrier station 202 and the inspecting station 205.

Figure 23:
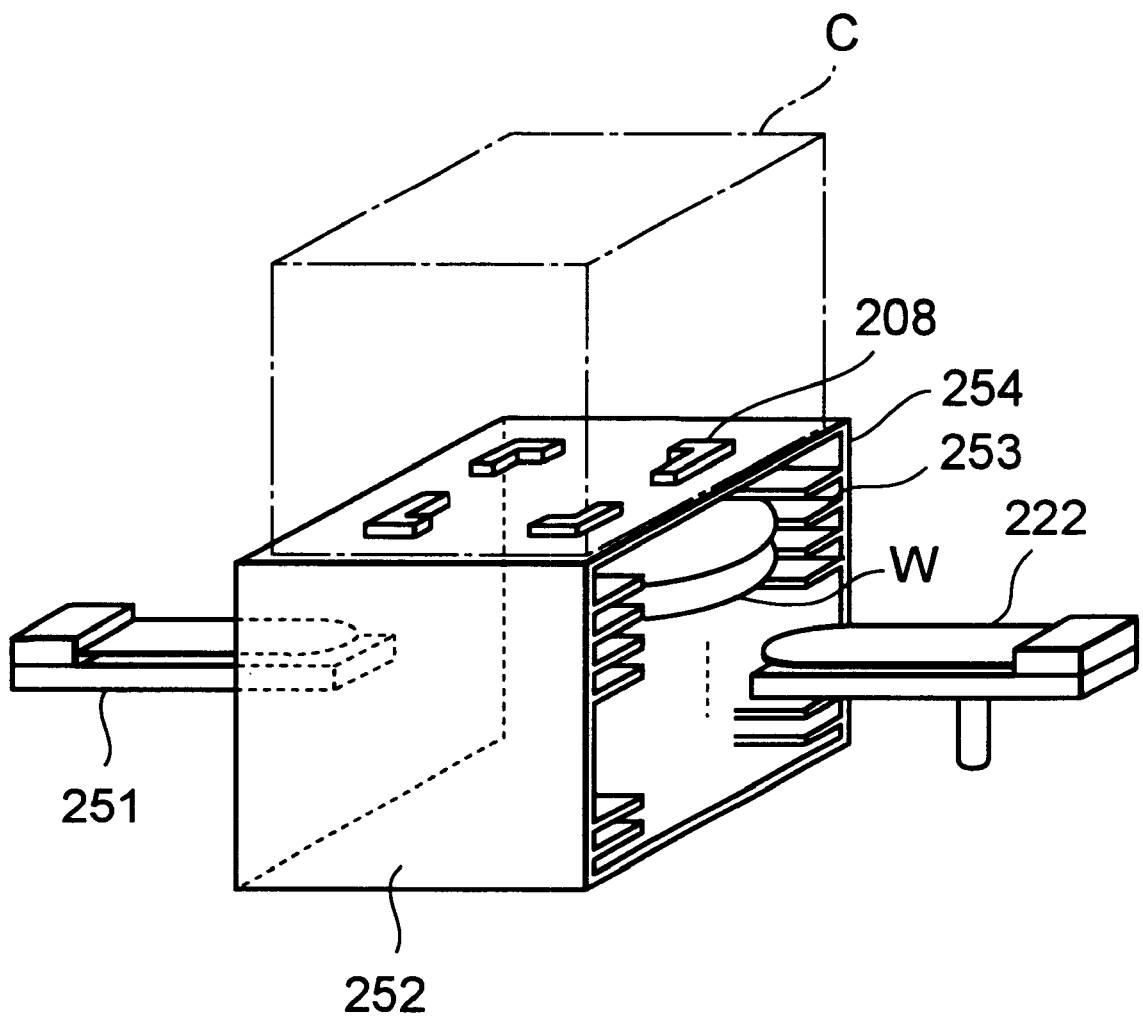
FIG. 23 is a perspective view showing an example of the structure of which a carrier that is brought from the outside is placed on the intermediate holding portion.

According to the embodiment, as shown in FIG. 23, an external carrier holding portion 208 composed of a guide portion that aligns a carrier C may be disposed on the intermediate holding portion 252. In the inspecting portion dedicated operation mode, a carrier C that contains a wafer W whose resist pattern has been formed outside of the apparatus may be placed on the external carrier holding portion 208.

Figure 24:
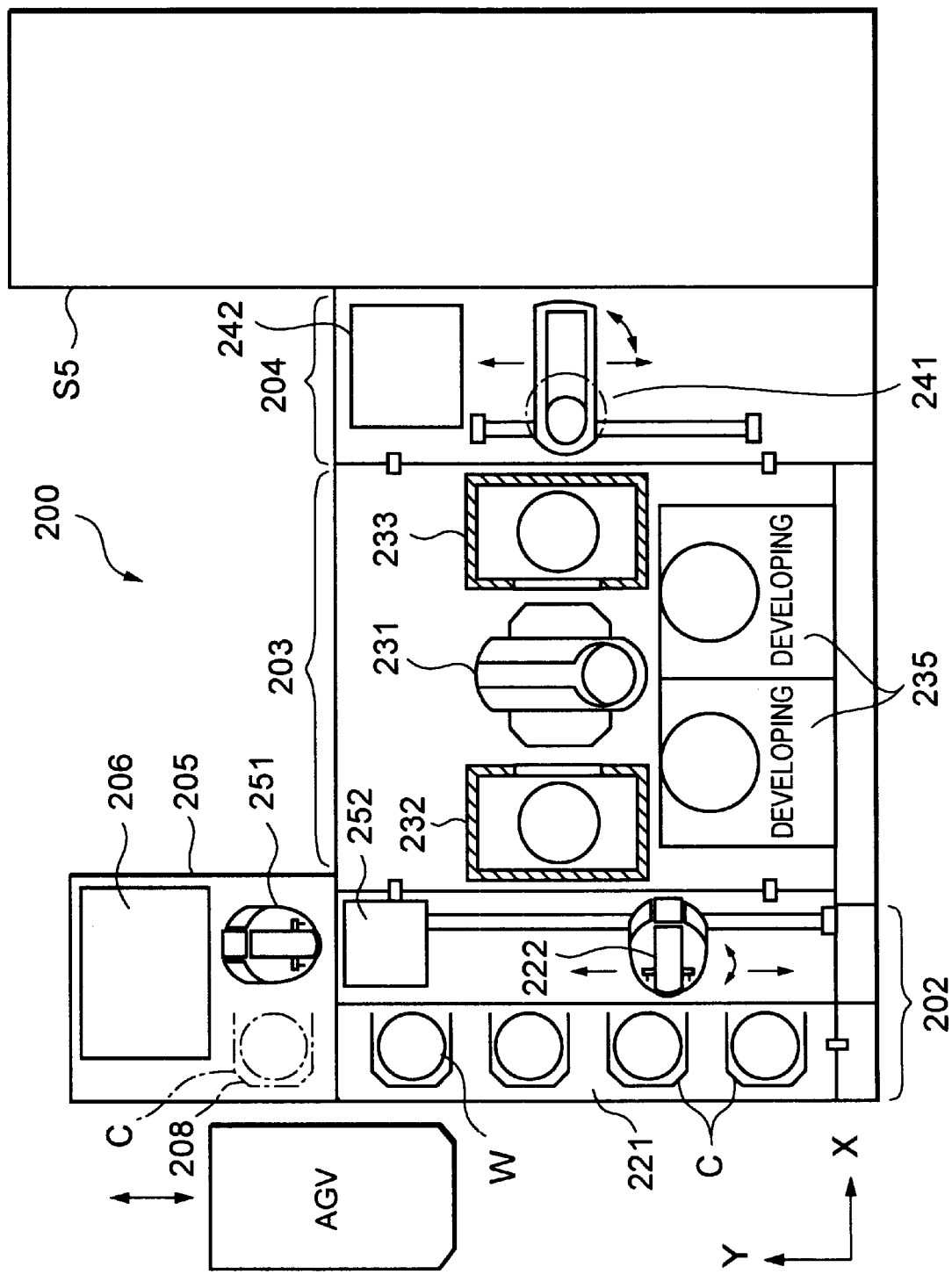
FIG. 24 is a schematic plan view showing the overall structure of another embodiment of the present invention.
Figure 25:
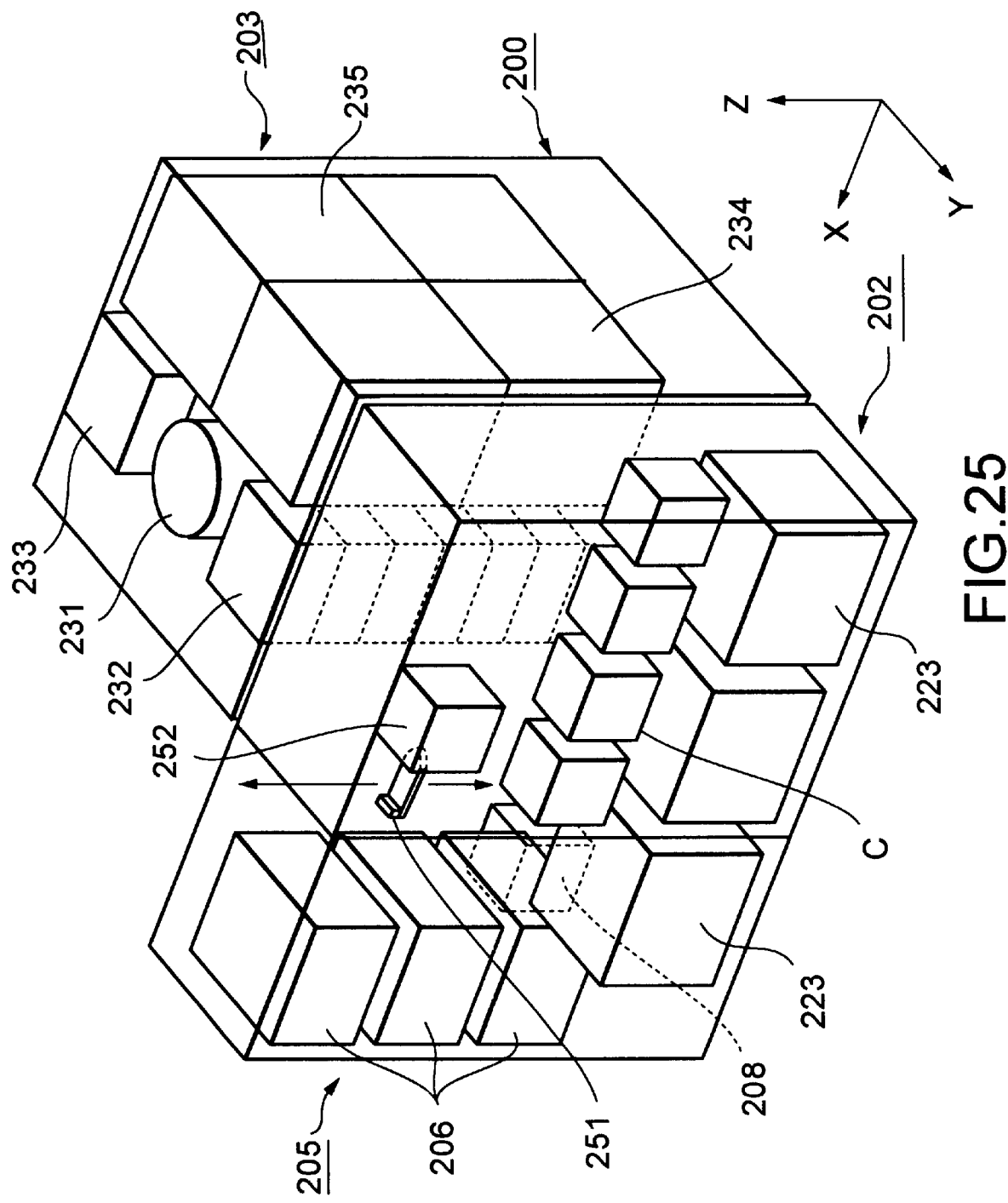
FIG. 25 is a schematic perspective view showing the embodiment shown in FIG. 24.

FIGS. 24 and 25 show an example of which the external carrier holding portion 208 having the carrier aligning portion is disposed in the inspecting station 206 in the structure shown in FIG. 23. The external carrier holding portion 208 is disposed in the same height as for example the carrier loading/unloading portion 221 and faces the transferring path of the automatic transferring robot AGV. The automatic transferring robot AGV loads and unloads a carrier C. In this case, a wafer W contained in a carrier C placed on the external carrier holding portion 208 is directly taken by the auxiliary transfer mechanism 251 and transferred to the pattern inspecting portion 206. Thus, a wafer W can be inspected in a apparatus rather than the coating and developing apparatus in the same clean room.

The schematic plan view of the auxiliary transfer mechanism 251 corresponds to the drawing of the transfer mechanism 222. This is because when the intermediate holding portion 252 is structured as a multi-staged holding table (see FIG. 17), mapping sensors are required. When the intermediate holding portion 252 has a dedicated loading stage and a dedicated unloading stage as shown in FIG. 18, the intermediate holding portion 252 is structured as a transfer mechanism that does not have mapping sensors.

Figure 26:
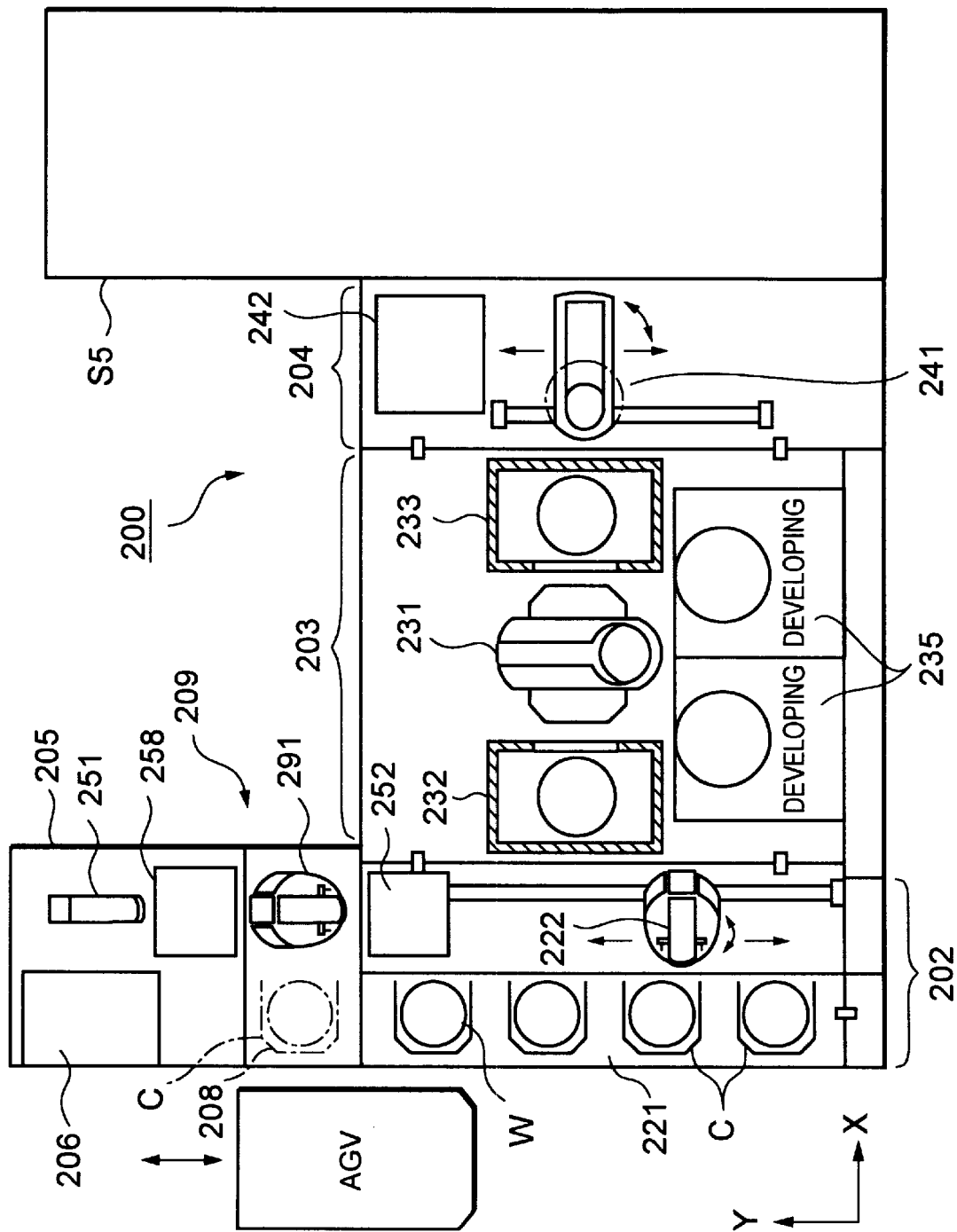
FIG. 26 is a schematic plan view showing the overall structure of another embodiment of the present invention.

According to the embodiment shown in FIG. 26, when only a pattern inspecting portion 206 is used, an external substrate loading/unloading station 209 that loads and unloads a wafer W from/to the outside of the apparatus can be connected and disconnected between the carrier station 202 and the inspecting station 205. The external substrate loading/unloading station 209 is disposed at the position facing the transferring path of the automatic transferring robot AGV. The external substrate loading/unloading station 209 has the external carrier holding portion 208 and a second transfer mechanism 291. The automatic transferring robot AGV loads and unloads a carrier C from/to the external carrier holding portion 208. The second transfer mechanism 291 is a second transferring portion that transfers a wafer W to and from the external carrier holding portion 208.

The inspecting station 205 has an intermediate holding portion 258 on which a wafer W is transferred between the auxiliary transfer mechanism 251 and the second transfer mechanism 291. Although the intermediate holding portion 258 may be structured as shown in FIGS. 17 and 18, in the example, since the intermediate holding portion 252 having the multi-staged holding table is disposed in the carrier station 202, the intermediate holding portion 258 is composed of for example a loading stage and an unloading stage.

According to the embodiment, in the regular operation mode, after each process is performed (for example, after a coating process, after an exposing process, or after a developing process), a wafer W is transferred in the path of the first transfer mechanism 222, the intermediate holding portion 252, the second transfer mechanism 291, the intermediate holding portion 258, the auxiliary transfer mechanism 251, and the pattern inspecting portion 206. In the inspecting portion dedicated operation mode, a wafer W contained in a carrier C placed on the external carrier holding portion 208 is transferred in the path of the second transfer mechanism 291, the intermediate holding portion 258, the auxiliary transfer mechanism 251, and the pattern inspecting portion 206.

In the method for transferring a wafer W that has been developed in the processing station 203 to the inspecting station 205, a transfer mechanism that directly transfers the wafer W from the processing station 203 to the inspecting station 205 may be disposed instead of using the transfer mechanism 222. The substrate is not limited to a wafer. Instead, the wafer may be a glass substrate for a liquid crystal display.

Figure 27:
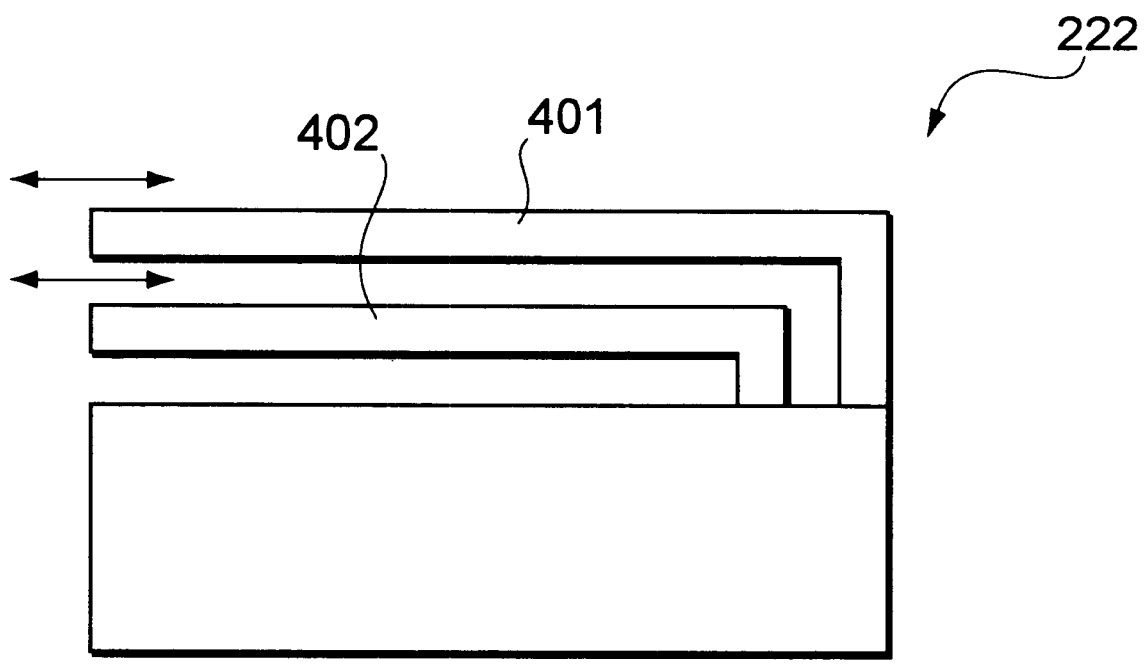
FIG. 27 is a side view showing the structure of a transfer mechanism according to the present invention.

The transfer mechanism 222 may have a first arm 401 and a second arm 402 as an upper arm and a lower arm, respectively, as shown in FIG. 27. The first arm 401 as the upper arm has a higher centering accuracy than the second arm 402 as the lower arm.

The centering accuracy represents the degree of an accuracy of which a wafer W is transferred from an arm to a desired position of a apparatus (holding portion). The higher accuracy parts that compose the arm have, the higher the centering accuracy is.

According to the embodiment, the first arm 401 having a higher centering accuracy loads a wafer W from the intermediate holding portion 258 to the pattern inspecting portion 206. In contrast, the second arm 402 having a lower centering accuracy unloads a wafer W from the pattern inspecting portion 206 to the intermediate holding portion 258.

Thus, as shown in FIG. 27, when the transfer mechanism 222 is structured as a two-staged arm, a wafer W can be effectively and quickly transferred between the intermediate holding portion 258 and the pattern inspecting portion 206. In addition, since the accuracy of the first arm 401 is higher than the accuracy of the second arm 402, a wafer W can be more accurately inspected. Moreover, transfer mechanism 222 can be inexpensively produced.

As was described above, according to the present invention, since the pattern inspection and so forth can be performed in the coating and developing apparatus, the throughput of the apparatus is improved. When a maintenance operation is performed for the processing station that performs coating and developing processes or when the coating and developing processes are stopped, only the inspecting portion can be used. Thus, the pattern inspection and so forth can be performed for a wafer W brought from the outside of the apparatus.

Figure 28:
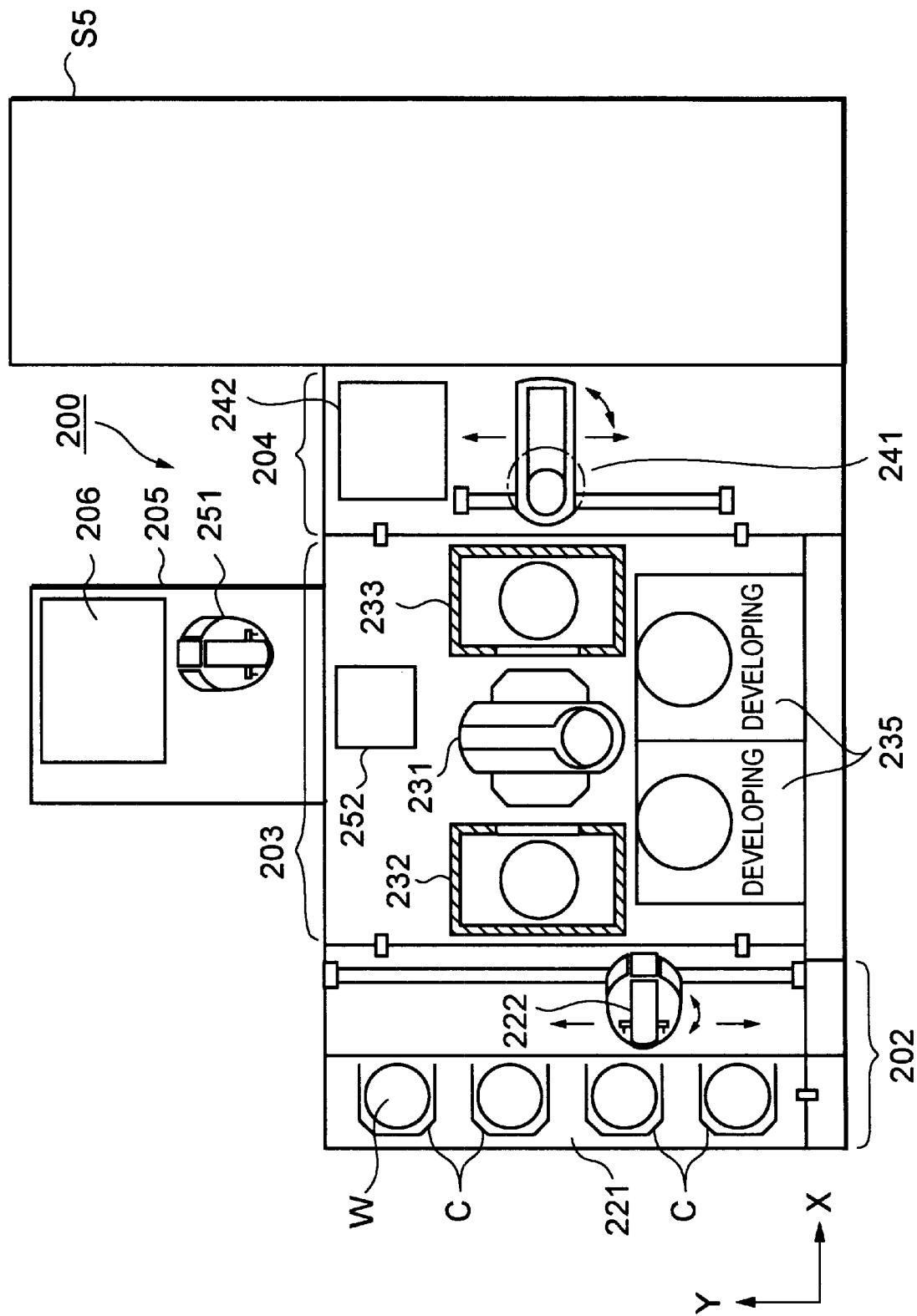
FIG. 28 is a schematic plan view showing a coating and developing apparatus according to another embodiment of the present invention.
Figure 29:
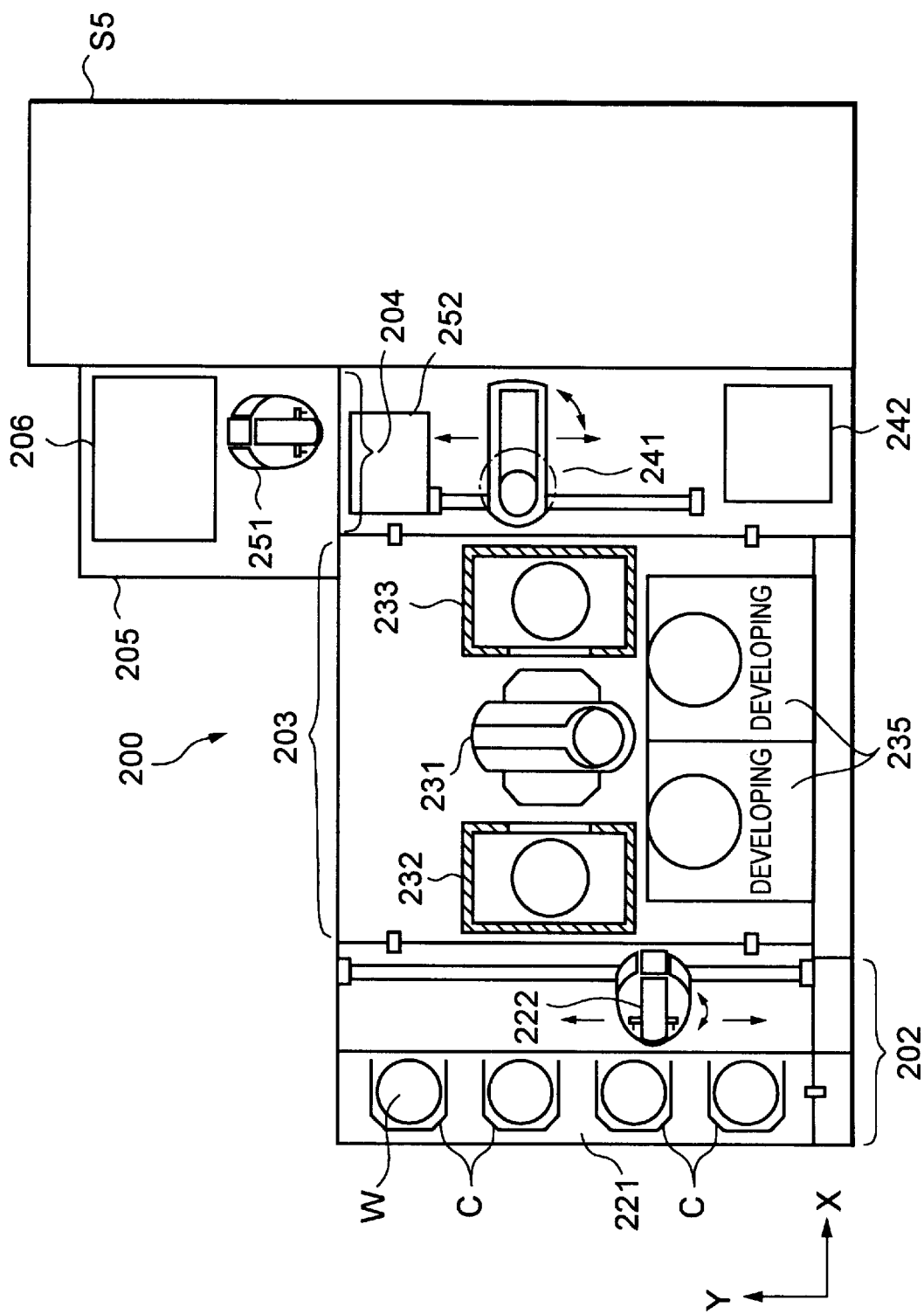
FIG. 29 is a schematic plan view showing a coating and developing apparatus according to still another embodiment of the present invention.

According to the above-described embodiment, the inspecting station 205 is connected to the carrier station 202. As shown in FIG. 28, the inspecting station 205 may be connected to the processing station 203. As shown in FIG. 29, the inspecting station 205 may be connected to the interface station 204. Alternatively in the structure of which the inspecting station 205 is connected to the carrier station 202, another inspecting station may be connected to the processing station 203. Furthermore, another inspecting station may be connected to the interface station 204.

Figure 30:
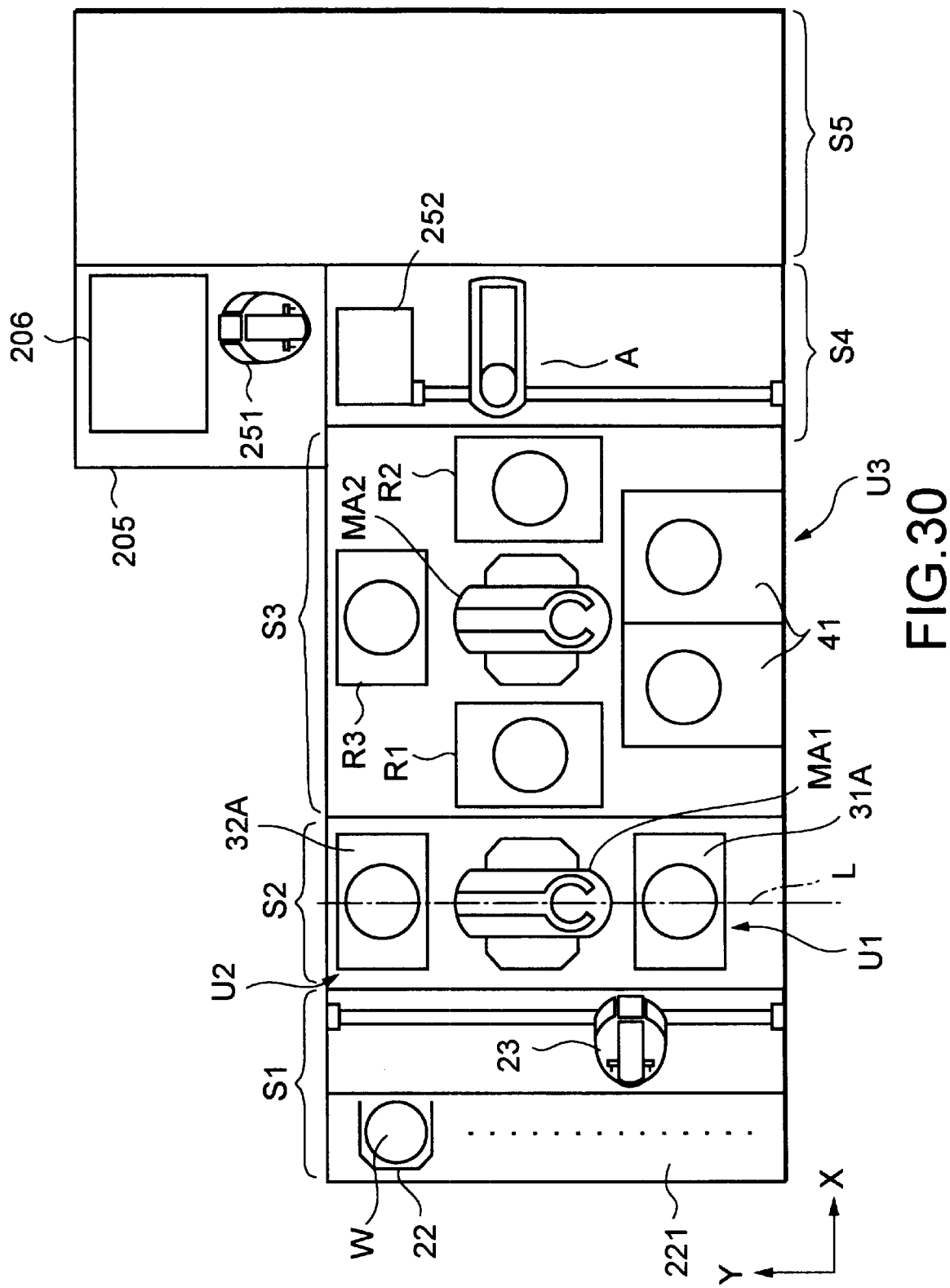
FIG. 30 is a schematic plan view showing a coating and developing apparatus according to yet another embodiment of the present invention.

As shown in FIG. 30, the inspecting station 205 may be connected to the interface station S4 in the structure shown in FIG. 1.

Figure 9:
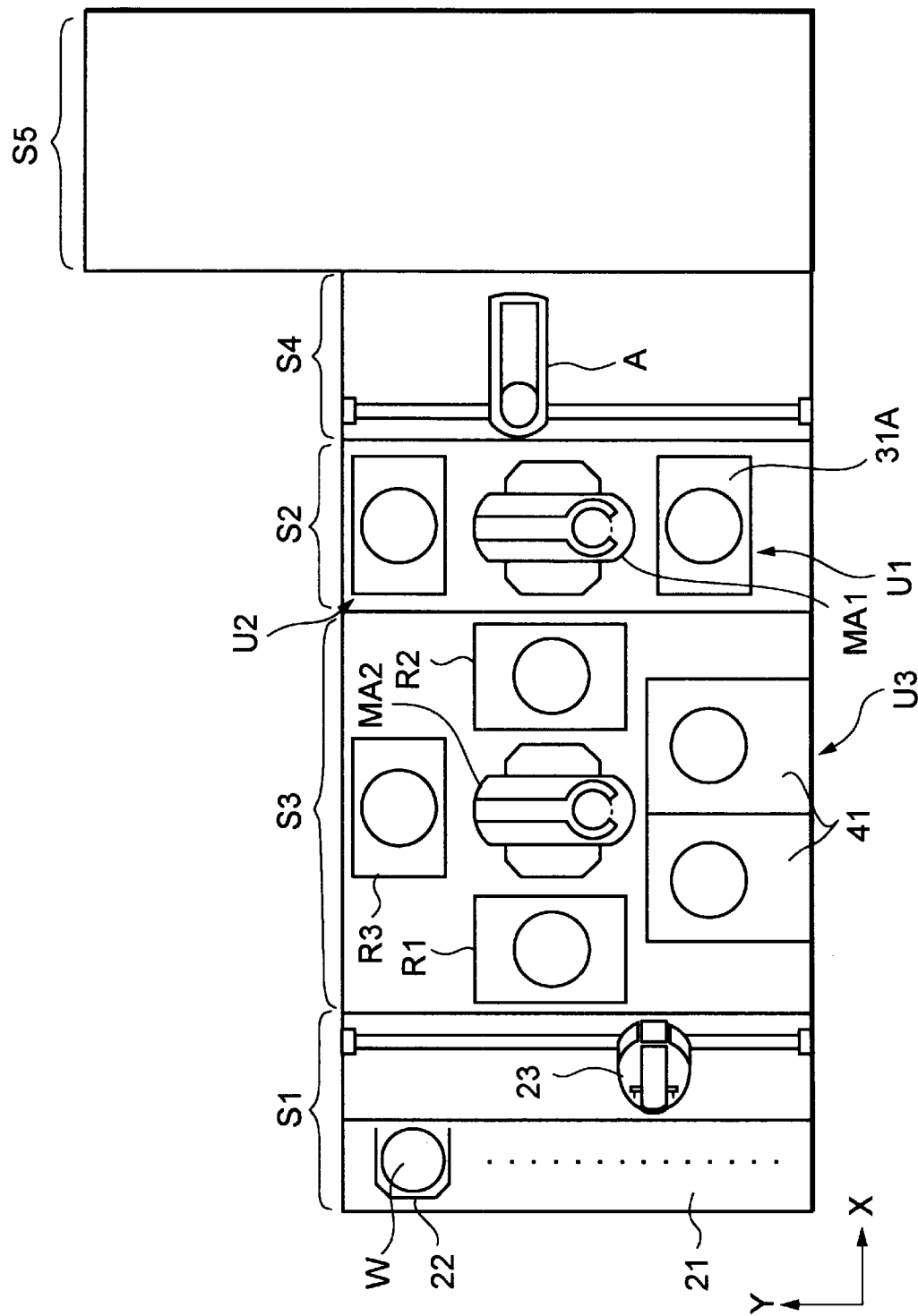
FIG. 9 is a schematic plan view showing a coating and developing apparatus according to another embodiment of the present invention.
Figure 31:
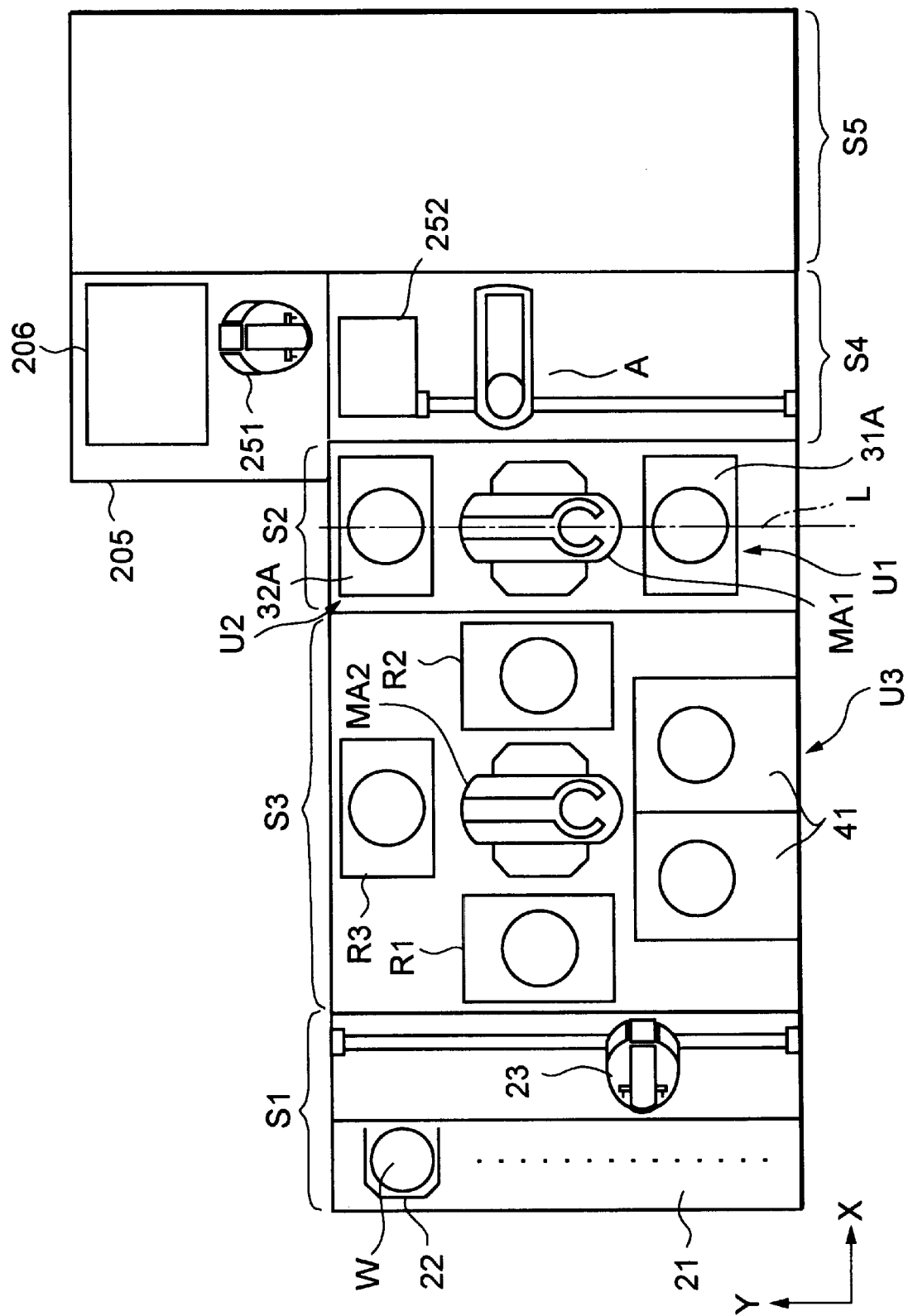
FIG. 31 is a schematic plan view showing a coating and developing apparatus according to still another embodiment of the present invention.

As shown in FIG. 31, the inspecting station 205 may be connected to the cassette station S1 in the structure shown in FIG. 9.

Figure 32:
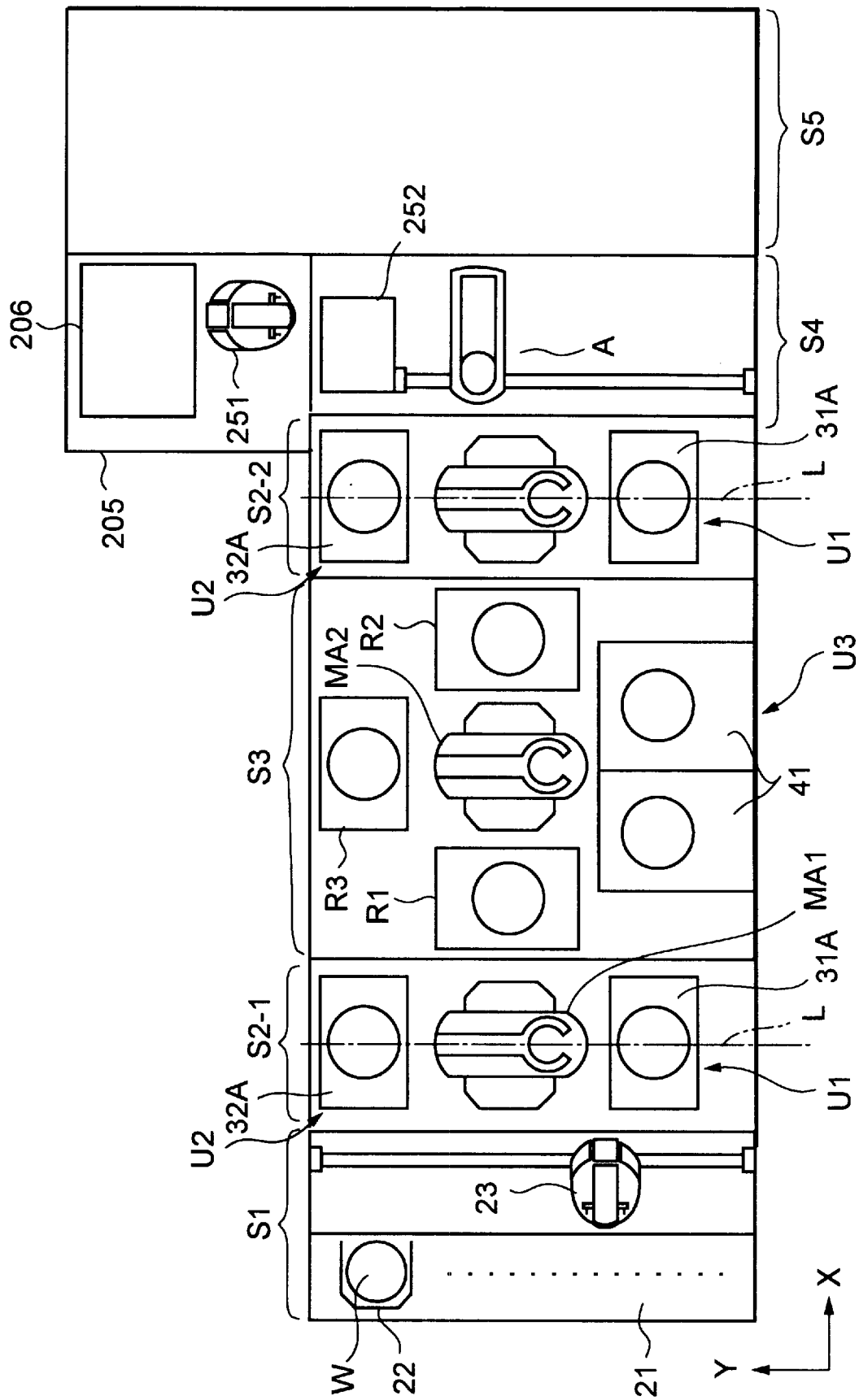
FIG. 32 is a schematic plan view showing a coating and developing apparatus according to yet another embodiment of the present invention.

As shown in FIG. 32, the inspecting station 205 may be connected to the interface station S4 in the structure shown in FIG. 11.

In addition, according to the present invention, besides such system structures, various combinations are available.

The above-described inspecting apparatus may be disposed in a special station. Alternatively, the inspecting apparatus may be disposed at a particular position of the coating and developing apparatus. Alternatively, the inspecting apparatus may be disposed instead of each unit. Alternatively, the inspecting apparatus may be used along with the above-described inspecting station.

Figure 33:
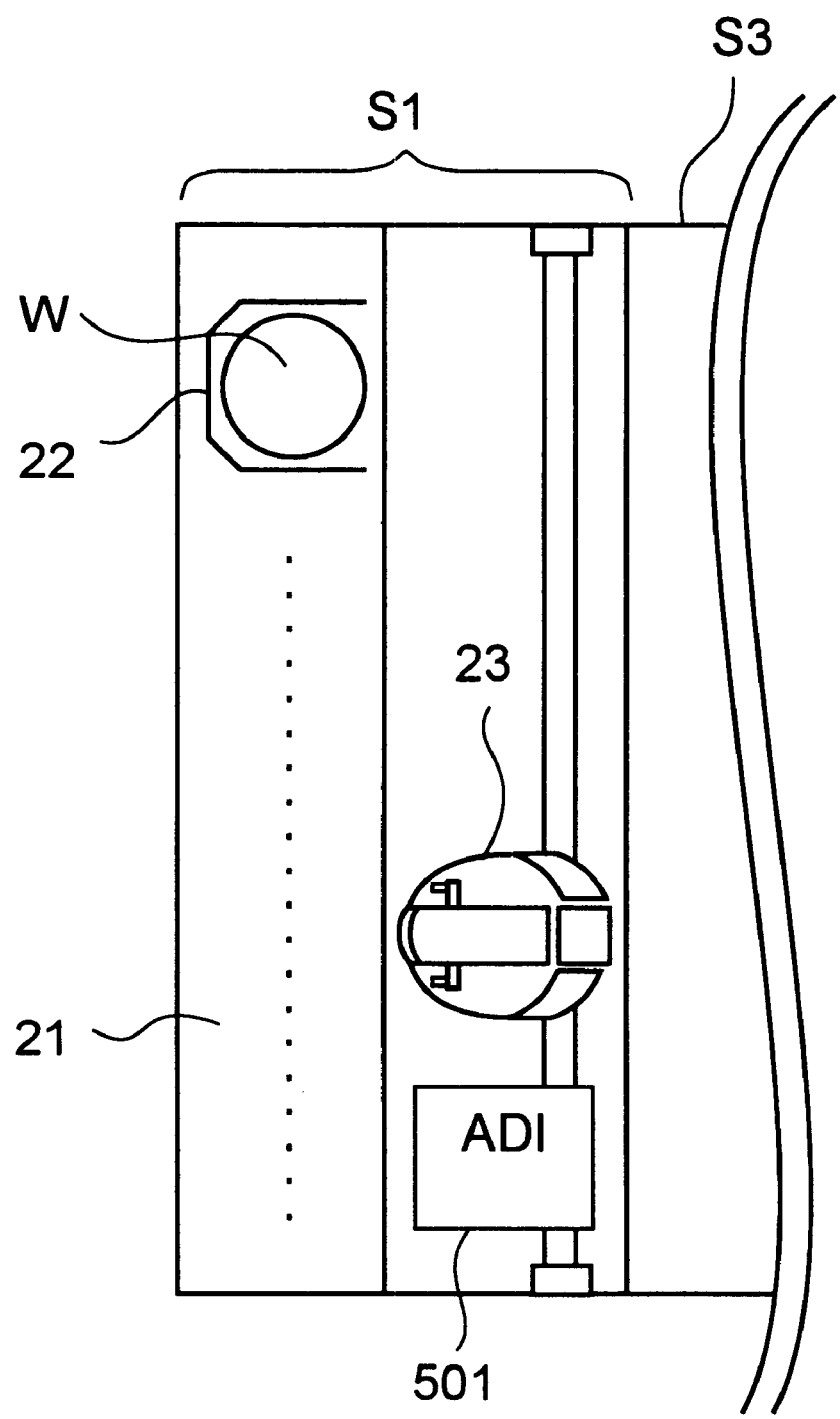
FIG. 33 is a plan view showing a cassette station according to another embodiment of the present invention.
Figure 34:
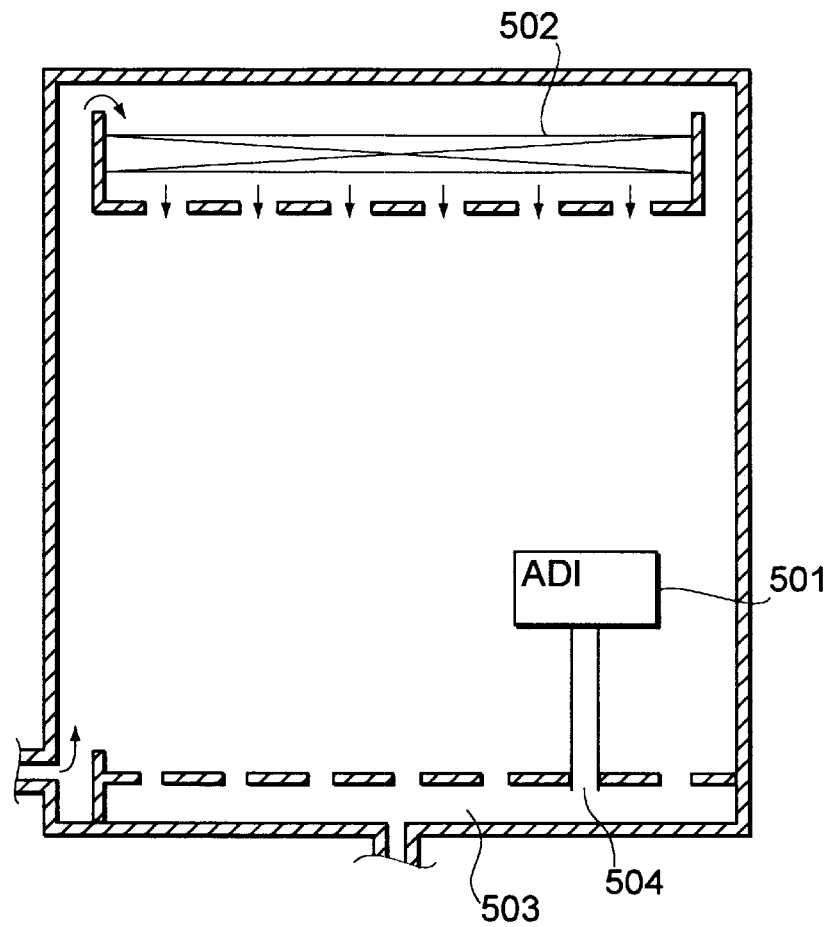
FIG. 34 is a front view showing a cassette station shown in FIG. 33.
Figure 35:
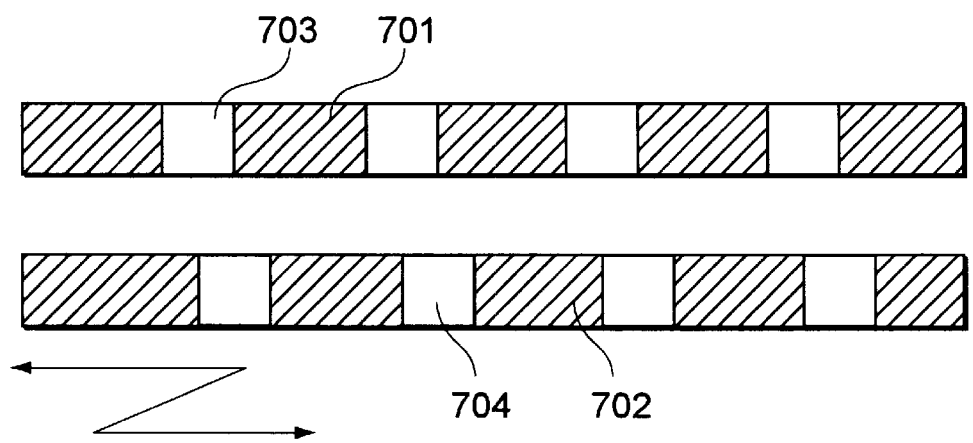
FIG. 35 is a schematic diagram for explaining a mechanism that controls a pressure according to the embodiment shown in FIG. 33 and FIG. 34.

FIGS. 33 and 34 show an example of which an inspecting apparatus 501 is disposed in the cassette station S1. A FFU 502 (Fun Filter Unit) is disposed at an upper portion of the cassette station S1. An exhausting mechanism 503 is disposed at a lower portion of the cassette station S1. In this case, an inspecting apparatus 501 is disposed in the cassette station S1 and connected to another exhausting mechanism 504. In this case, it is preferred to satisfy the relation of inner pressure of processing station S3>inner pressure of cassette station S1>inner pressure of inspecting apparatus 501>inner pressure of clean room. In other words, it is preferred that the processing station S3 has the highest positive pressure and the inspecting apparatus 501 and the clean room have negative pressures. Thus, in a process of the system, foreign matter can be effectively suppressed from entering a wafer W. Such pressure adjustments can be performed by FFUs and exhausting mechanisms of the individual stations. In that case, by interposing a punched metal between the FFU or the exhausting mechanism and each station, adjusting the number of holes of the punched metal and the size of each hole thereof, interposing a plurality of (for example, two) punched metals between the FFU or the exhausting mechanism and each station, or adjusting the positions of two punched metals 701 and 702 (namely, their overlapping state of holes 703 and 704), the pressures can be adjusted.

Next, another embodiment of the present invention will be described.

Figure 36:
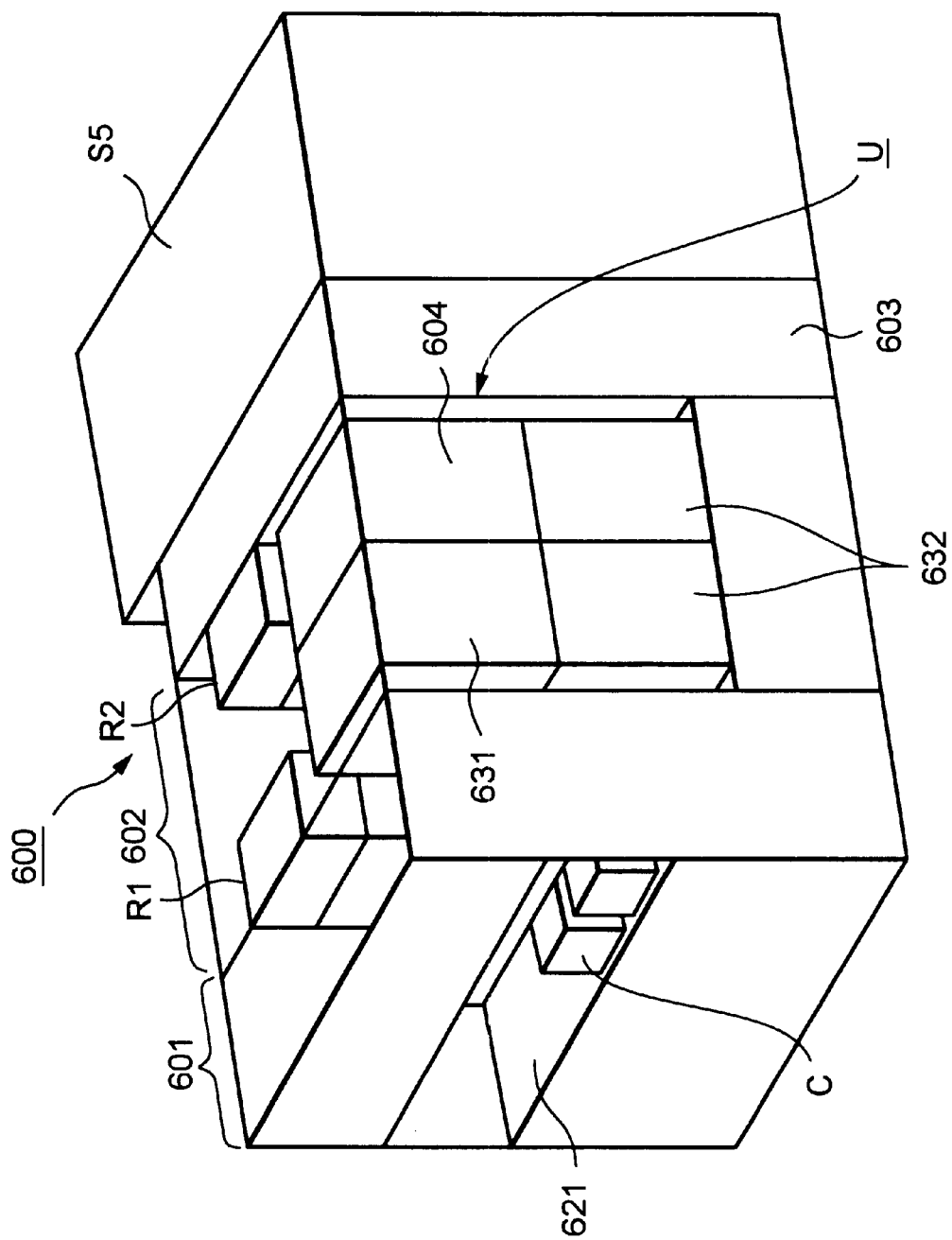
FIG. 36 is a schematic diagram showing a coating and developing apparatus according to another embodiment of the present invention.
Figure 37:
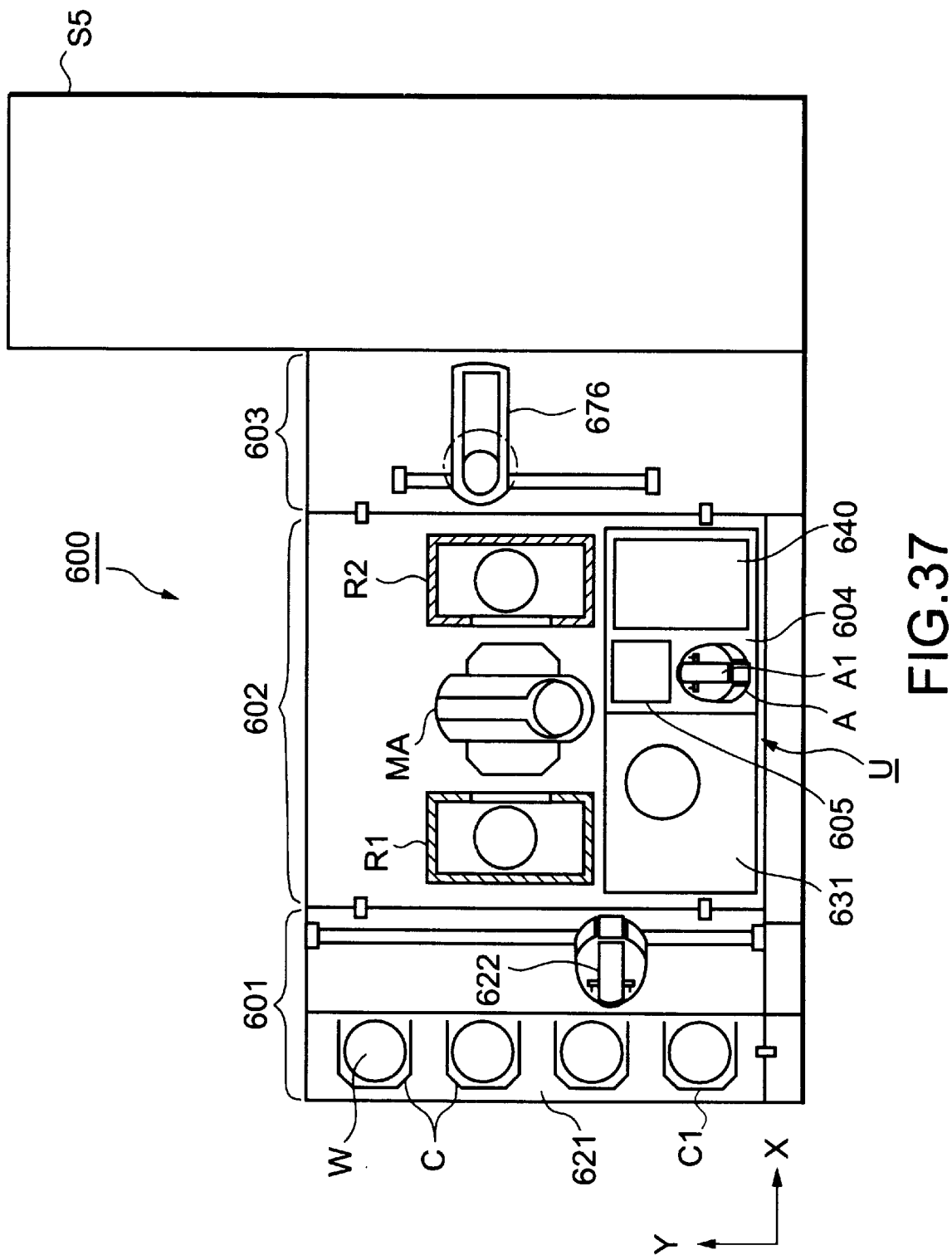
FIG. 37 is a schematic plan view showing the coating and developing apparatus shown in FIG. 36.

FIG. 36 is a schematic, perspective view showing the overall structure of a coating and developing system according to an embodiment of the present invention. In the coating and developing system, a coating and developing apparatus 600 is connected to the aligner S5. FIG. 37 is a plan view showing the interior of the system. In FIGS. 36 and 37, reference numeral 601 represents a cassette station. Reference numeral 602 represents a processing station. Reference numeral 603 represents an interface station.

The cassette station 601 loads and unloads wafer cassettes (hereinafter referred to as cassettes) C. Each cassette C contains a plurality of wafers W (for example 25 substrates) in a shelf shape. The cassette station 601 has a cassette stage 621, cassettes C, and a transfer mechanism 622. The cassette stage 621 is a holding portion that holds for example four cassettes C. The cassettes C are placed on the cassette stage 621. The transfer mechanism 622 is a transferring portion that transfers a wafer W to and from the processing station 602 (that will be described later). The transfer mechanism 622 can be elevated, moved in the X and Y directions, and rotated around the vertical axis.

The processing station 602 is disposed in the direction approximately perpendicular to the direction of the disposition of the cassettes C on the cassette station 601 (namely, in the X direction of FIG. 37) and connected to the cassette station 601. The processing station 602 has a developing unit 631, a coating unit 632, an inspecting unit 604, a main transfer mechanism MA, and a shelf unit R. The developing unit 631 and the coating unit 632 compose a substrate processing portion. The inspecting unit 604 has a plurality of inspecting portions that inspect the processed states of a wafer W. A wafer W is transferred between the cassette station 601 and the interface station 603. The processing station 602 performs a resist solution coating process, a developing process, a heating process, a cooling process, and an inspecting process for a wafer W. The processing station 602 perform the heating process or the cooling process after or before the developing process and the resist solution coating process. The processing station 602 inspects the processed states for the predetermined processes for a wafer W.

Next, an example of the layout of the processing station 602 will be described. For example, at the center of the processing station 602, the main transfer mechanism MA is disposed. When viewed from the cassette stage 621, shelf units R1 and R2 are disposed on the near side and the far side of the main transfer mechanism MA.

When viewed from the cassette stage 621, on the right side, a processing unit U is disposed in two stages. The processing unit U has one developing unit 631, two coating units 632, and one inspecting unit 604. In the example, one developing unit 631 and one inspecting unit 604 as upper staged units and two coating units 632 as lower staged units are disposed. The main transfer mechanism MA transfers a wafer W among the developing unit 631, the coating units 632, the inspecting unit 604, and the shelf units R1 and R2. As will be described later, the main transfer mechanism MA can be elevated, moved leftward and rightward, moved forward and backward, and rotated around the vertical axis. For simplicity, the main transfer mechanism MA is omitted in FIG. 36.

Figure 38:
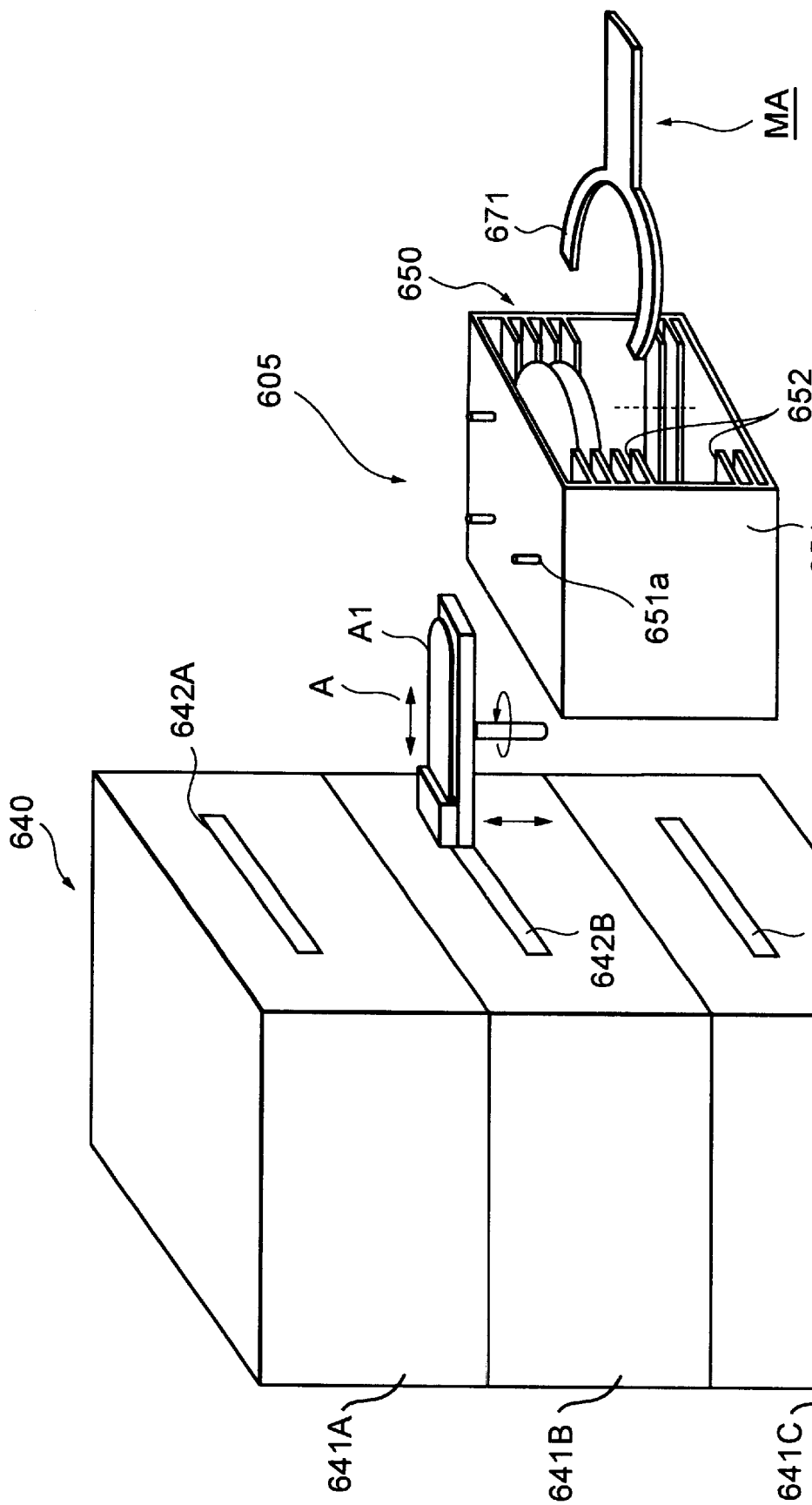
FIG. 38 is a perspective view showing an inspecting unit of the coating and developing apparatus shown in FIG. 36.
Figure 39:
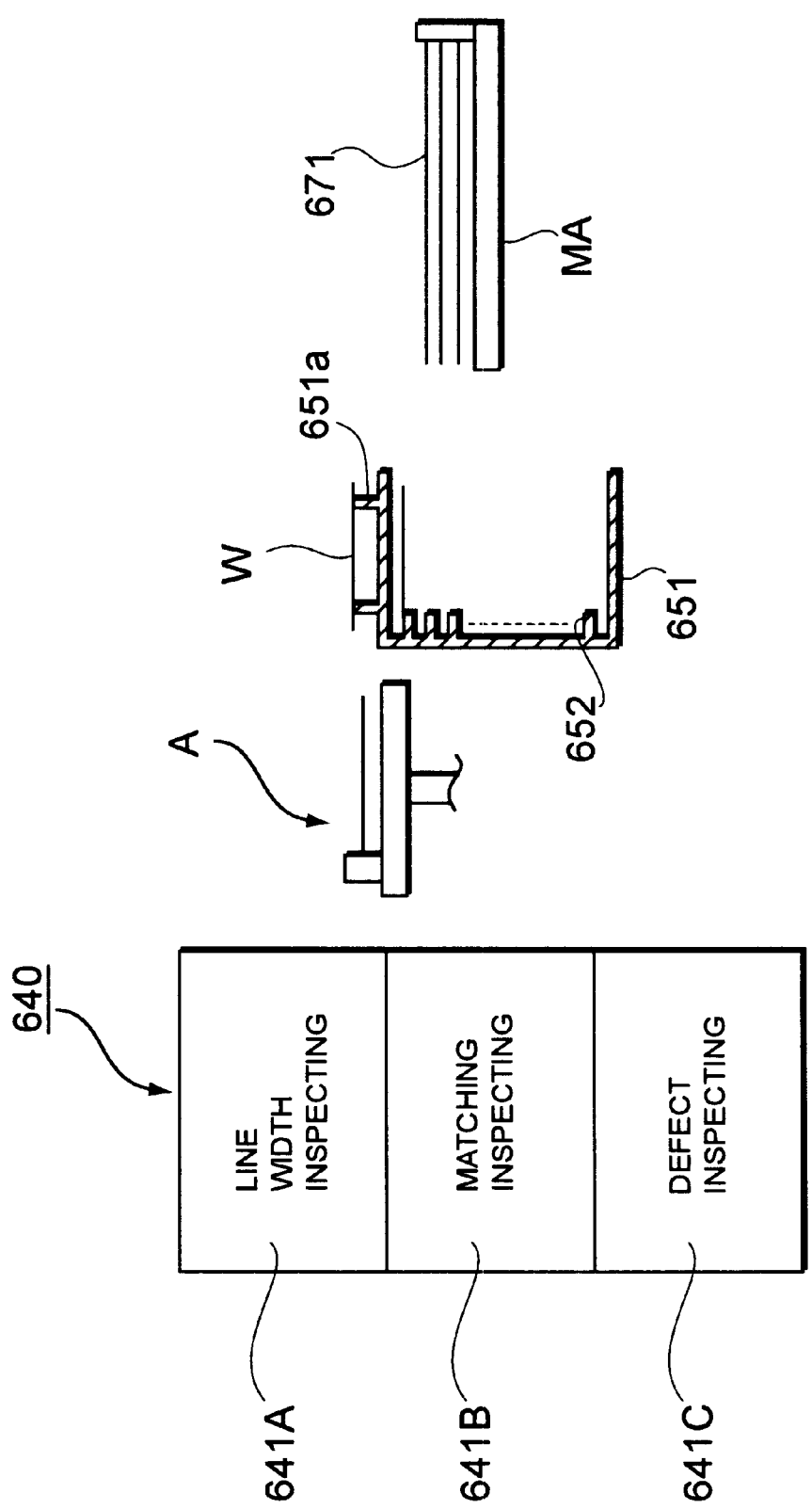
FIG. 39 is a sectional view showing the inspecting unit shown in FIG. 36.

FIG. 38 is a perspective view showing the inspecting unit 604. FIG. 39 is a sectional view showing the inspecting unit 604. Referring to FIGS. 38 and 39, the inspecting unit 604 has a transferring stage 605 and an auxiliary transfer mechanism A. The transferring stage 605 transfers a wafer W between the inspecting apparatus 640 and the main transfer mechanism MA. The auxiliary transfer mechanism A is a dedicated auxiliary transfer mechanism that transfers a wafer W between the transferring stage 605 and the inspecting apparatus 640.

The transferring stage 605 is an inspecting substrate holding portion that transfers a wafer W to and from the main transfer mechanism MA. The transferring stage 605 is disposed at the position that the main transfer mechanism MA can access a wafer W. In addition, the transferring stage 605 has a plurality of (for example, three) protrusions 651*a* on a vessel 651 that contains a wafer W. The protrusions 651*a* are formed at positions that do not interfere with an arm 671 (that will be described later) of the main transfer mechanism MA and an arm A1 of the auxiliary transfer mechanism A that transfer a wafer W to and from the transferring stage 605.

The arm 671 and the arm A1 that hold a wafer W lower and transfer the wafer W to the protrusions 651*a* between the transferring stage 605 and each of the main transfer mechanism MA and the transfer mechanism A. In addition, the arm 671 and the arm A1 rise from the lower side of the wafer W on the protrusions 651*a* and pick it up. Thus, the height of the protrusions 651*a* is larger than the thickness of each of the arm 671 and the arm A1 so that when the protrusions 651*a* hold the wafer W, the arm 671 and the arm A1 can move forward and backward by a predetermined value.

The lower side of the transferring stage 605 (namely, the vessel 651) is structured as a wafer holding portion 650 that holds a predetermined number of wafers W in a shelf shape. The wafer holding portion 650 is a substrate holding portion. The wafer holding portion 650 has an open side facing the main transfer mechanism MA so that it can transfer a wafer W to and from the vessel 651 having shoulder portions 652 that hold peripheral portions of wafers W and that are formed at predetermined intervals, therefore, wafer W is disposed in vertical direction.

Between the wafer holding portion 650 and the main transfer mechanism MA, the arm 671 that holds a wafer W lowers from the upper side of the shoulder portions 652 and transfers the wafer W to one of the shoulder portions 652. The arm 671 rises from the lower side of the wafers W of the shoulder portions 652 and picks it up. Thus, the size and the intervals of the shoulder portions 652 are designated so that the arm 671 does not interfere with the shoulder portions 652. In addition, the number of shoulders of the shoulder portions 652 depends on the inspecting process time and the transferring intervals of wafers W of the coating and developing apparatus 600.

The inspecting apparatus 640 has a plurality of (for example, three) inspecting portions 641 (641A, 641B, and 641C) at positions that the transfer mechanism A can access. For simplicity, FIG. 48 shows an image of which a wafer W is transferred between the transferring stage 605 and the inspecting apparatus 640.

The three inspecting portions 641 are a line width inspecting apparatus 641A that inspects for example developed line widths, a matching inspecting apparatus 641B that inspects the matching of the upper layer resist pattern and the base pattern, and a defect inspecting apparatus 641C that inspects scratches on the front surface of the resist film (scratch detection), presence/absence of foreign matter contained in resist solution (comet detection), and developed irregularities and developing defects. The auxiliary transfer mechanism A transfers a wafer W between each of the inspecting portions 641A, 641B, and 641C and the wafer holding portion 650 through wafer transferring openings 642A, 642B, and 642C, respectively.

Figure 4:
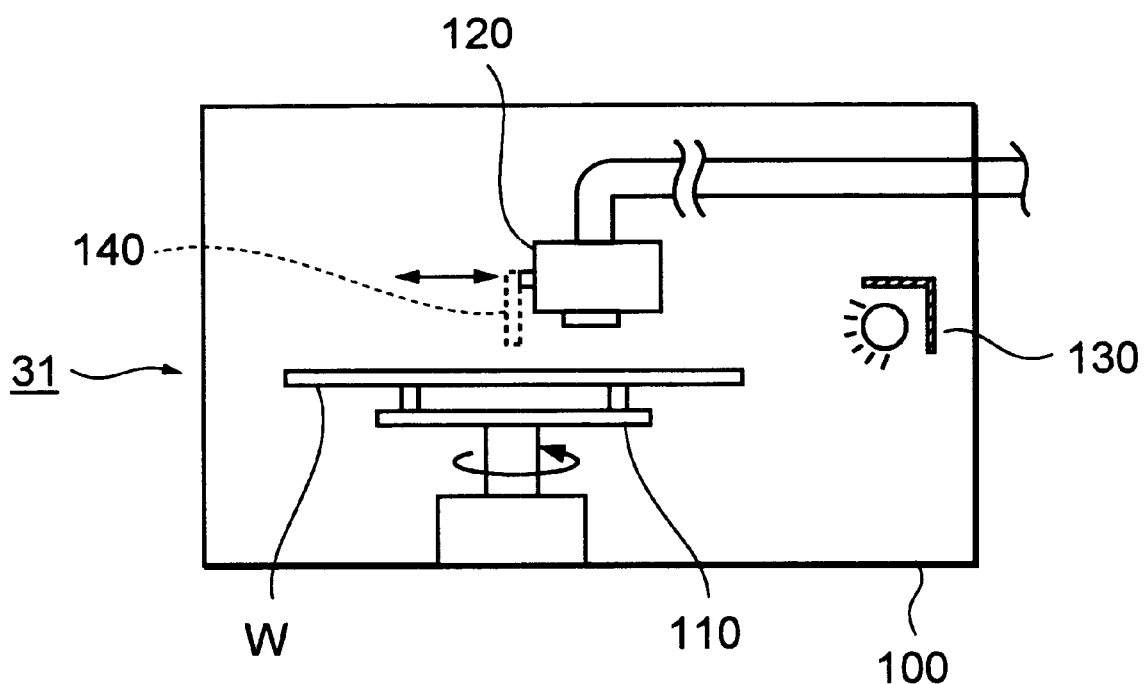
FIG. 4 is a sectional view showing an example of an inspecting portion.

The line width inspecting apparatus 641A, the matching inspecting apparatus 641B, and the defect inspecting apparatus 641C perform the predetermined inspections using for example a CCD camera as shown in FIG. 4.

The transfer mechanism A transfers a wafer W between the transferring stage and each inspecting portion 641. As with the transfer mechanism 622, the auxiliary transfer mechanism A1 can be elevated, moved in the X and Y directions, and rotated around the vertical axis.

It is not always necessary to dispose the inspecting apparatus 640 in the processing unit U. Instead, as long as the main transfer mechanism MA can access the transferring stage 605, the inspecting unit 640 may be disposed at any position of the processing station 602. In addition, as long as a wafer W can be transferred between the main transfer mechanism MA and the inspecting portions 641, the inspecting unit 640 can be disposed at any position and the number of inspecting portions 641 may be more or less than three. The types of inspecting portions 641 are not limited to the above examples. In other words, for example, a film thickness inspecting apparatus, a defocus inspecting apparatus that inspects the deviation of an exposed pattern position, a particle inspecting apparatus that detects the number of particles that adhere to a wafer, a splash back inspecting apparatus that inspects whether or not solvent of resist solution that splashes from the front surface of a wafer re-adheres to the wafer, a common defect detecting apparatus that detects a common defect that takes place at the same position in the same shape on wafers, a scum detecting apparatus that detects a resist scum that leaves on a developed wafer, a cramping inspecting apparatus, a non-resist inspecting apparatus, a non-develop inspecting apparatus, and so forth may be disposed. In addition to the transferring stage 605, the main transfer mechanism MA may transfer a wafer W to and from each inspecting portion 641.

Figure 40:
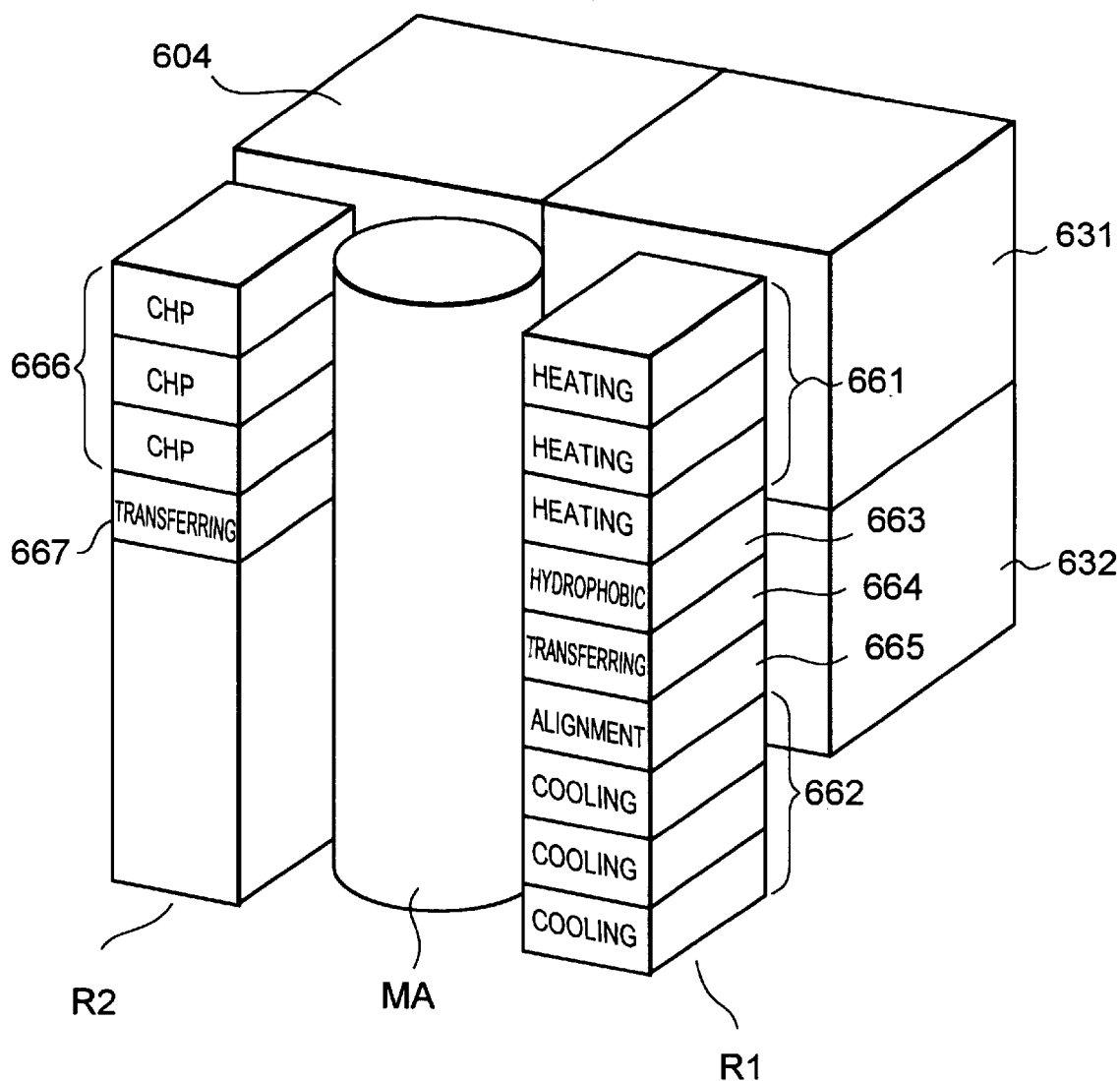
FIG. 40 is a perspective view showing an example of a shelf unit and a processing unit shown in FIG. 36.

As shown in FIG. 40, the shelf unit R1 has a heating portion 661 that heats a wafer W, a cooling portion 662 that cools a wafer W, a hydrophobic portion 663 that performs a hydrophobic process for the front surface of a wafer W, a transferring portion 664 having a transferring table on which a wafer W is transferred between the transfer mechanism 622 of the cassette station 601 and the main transfer mechanism MA of the processing station 602, and an alignment portion 665 that aligns a wafer W that are disposed in the vertical direction. The shelf unit R2 has a plurality of CHP apparatuses 666 (Chilling Hot Plate Processing stations) that heat and cool a wafer W, a transferring portion 667 that has a transferring table on which a wafer W is transferred between a transfer mechanism of an interface station 603 (that will be described later) and the main transfer mechanism MA of the processing station 602, and so forth that are disposed in the vertical direction. The apparatuses shown in FIG. 40 are just examples. In other words, a heating portion and a cooling portion may be disposed on different shelves. In addition, when viewed from the cassette station 601, on the left, shelf units similar to the shelf units R1 and R2 may be slidably disposed along a guide rail.

The developing unit 631 is structured as shown in for example FIG. 7. The main transfer mechanism MA is structured as shown in for example FIG. 8.

In the processing station 602, the main transfer mechanism MA accesses the developing unit 631, the coating unit 632, the transferring stage 605 of the inspecting unit 604, and each portion of the shelf units R. The individual portions are accessed and their processes are started and completed at timings corresponding to a program stored in a controlling portion (not shown).

The interface station 603 is adjacently connected to the processing station 602 in the X direction. On the far side of the interface station 603, the aligner S5 is connected. The aligner S5 exposes a wafer W on which a resist film has been formed. The interface station 603 has a transfer mechanism 676 that transfers a wafer W between the processing station 602 and the aligner S5. To transfer a wafer W between the transferring portion 667 of the shelf unit R2 of the processing station 602 and the aligner S5, the transfer mechanism 676 can be elevated, moved leftward and rightward, moved forward and backward, and rotated around the vertical axis.

In the method according to the present invention, an example of which a developing process and a predetermined inspection are performed for a first wafer W of a predetermined number of wafers W contained in a cassette C will be described in the case that the throughput of the inspecting unit 604 is 60 sheets/hour and the throughput of the coating and developing apparatus 600 is 150 sheets/hour.

In the example, the process time of the inspecting portion is equivalent to the throughput of the inspecting unit 604, whereas the unloading intervals of substrates from the substrate processing portion are equivalent to the throughput of the coating and developing apparatus 600. When the throughput of the inspecting unit 604 is 60 sheets/hour, it takes 60 seconds to perform the inspection for one wafer W. When the throughput of the coating and developing apparatus 600 is 150 sheets/hour, the transferring intervals of wafers W of the coating and developing apparatus 600 are 24 seconds.

In the example, the throughput of the inspecting unit 604 is calculated corresponding to a time period for which a wafer W on the transferring stage 605 is successively transferred to the line width inspecting apparatus 641A, the matching inspecting apparatus 641B, and the defect inspecting apparatus 641C, processed therein, and then returned to the transferring stage 605.

First of all, the flow of a wafer W in the coating and developing apparatus 600 will be described. A cassette C that contains for example 25 non-processed wafers W is transferred to the cassette stage 621 by an automatic transferring robot (or an operator). The transfer mechanism 622 successively takes wafers W from the cassette C and places them to the transferring portion 664 of the shelf unit R1 of the processing station 602 without an inconsistency of the order of wafers W contained in the cassette C.

Each wafer W is transferred to the main transfer mechanism MA of the processing station 602 and then transferred to the coating unit 632. The coating unit 632 coats resist solution on the wafer W. Thereafter, the wafer W is transferred from the main transfer mechanism MA to the aligner S5 through the transferring portion 667 of the shelf unit R2 and the transfer mechanism 676 of the interface station 603.

Before resist solution is coated to the wafer W, the individual portions of the shelf units R perform a hydrophobic process and a cooling process for the wafer W. After resist solution is coated to the wafer W, the individual portions of the shelf units R perform a heating process and a cooling process for the wafer W. Depending on the type of the resist, a particular unit (not shown) coats a reflection protection film to the wafer W instead of performing the hydrophobic process.

The exposed wafer W is transferred to the processing station 602 in the reverse path. The developing unit 631 performs a developing process for the wafer W. Before and after the developing process, the CHP apparatus 666, the heating portion 661, and the cooling portion 662 of the shelf units R perform a heating process and a cooling process for the wafer W.

The first wafer W of wafers that have been developed is successively transferred to each of the inspecting portions 641 of the inspecting apparatus 640 through the transferring stage 605 of the inspecting unit 604 and the auxiliary transfer mechanism A by the main transfer mechanism MA. The inspecting portions 641 perform the predetermined inspections for the wafer W. In the example, an inspecting wafer W is selected from a predetermined number of wafers. For example, one wafer W is selected as an inspecting wafer for each cassette C. For example, the first wafer W contained in each cassette C becomes an inspecting wafer.

Figure 41A:
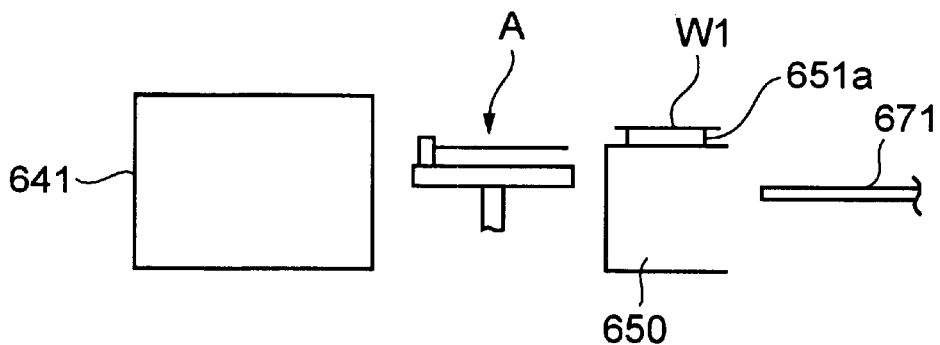
FIGS. 41A to 41D are schematic diagrams showing steps of a method used in the coating and developing apparatus according to the present invention.
Figure 41B:
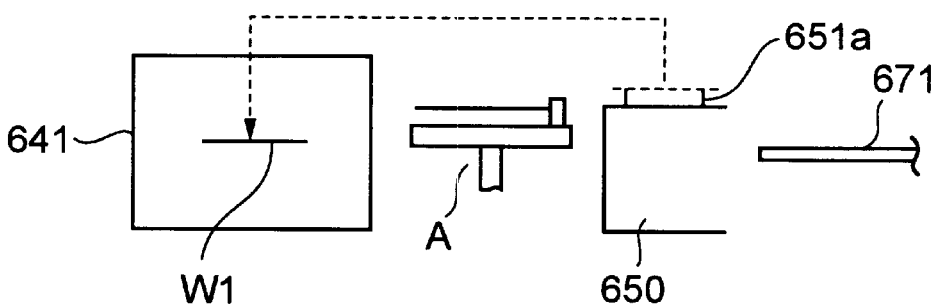

The present invention has a feature in the transferring method for a wafer W in the inspecting unit 604. Next, the method will be described. As shown in FIG. 41A, after a developing process and a heating process are performed for an inspecting wafer W as the first wafer contained in a cassette C, the inspecting wafer W is placed on the transferring stage 605 of the inspecting unit 604 by the main transfer mechanism MA. Thereafter, as shown in FIG. 41B, the wafer W is transferred to each of the inspecting portions 641 by the transfer mechanism A. The line width inspecting apparatus 641A inspects the developed line widths for the wafer W. The matching inspecting apparatus 641B inspects the matching of the upper layer resist pattern and the base pattern of the wafer W. The defect inspecting apparatus 641C inspects the developed irregularities and the developing defects for the wafer W.

Figure 41C:
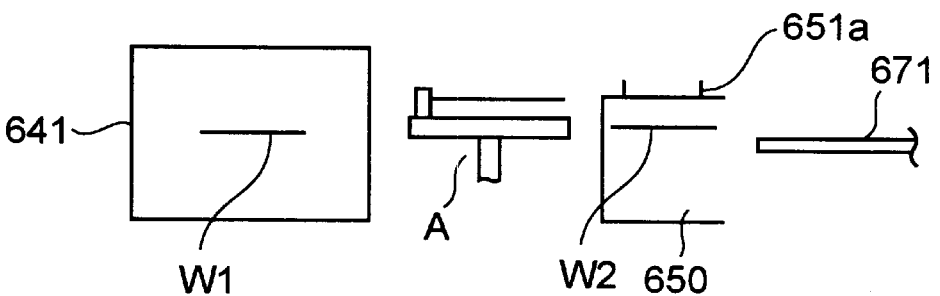
Figure 41D:
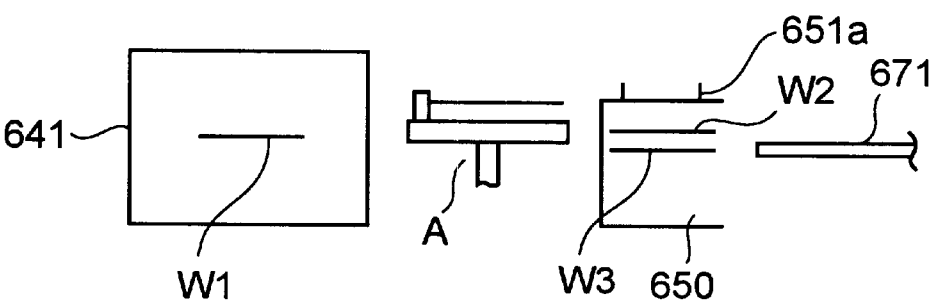

Since the time period for the inspection for the wafer W1 is 60 seconds and the transferring intervals of wafers W of the coating and developing apparatus 600 are 24 seconds, as shown in FIG. 41C, while the wafer W is being inspected, the second wafer W2 of the cassette C is transferred to the wafer holding portion 650 by the main transfer mechanism MA. Since the inspection for the wafer W1 has not been completed, as sown in FIG. 41D, while the wafer W1 is being inspected, the third wafer W3 is transferred to the wafer holding portion 650 by the main transfer mechanism MA.

The number of wafers W transferred to the wafer holding portion 650 by the main transfer mechanism MA depends on the inspection time period of the inspecting unit 604 and the throughput of the coating and developing apparatus 600. While the inspection is being performed for the inspecting wafer W1, after the predetermined pre-inspection process is completed for all wafers W, they are transferred to the wafer holding portion 650 in the order of those contained in the cassette C.

Figure 42A:
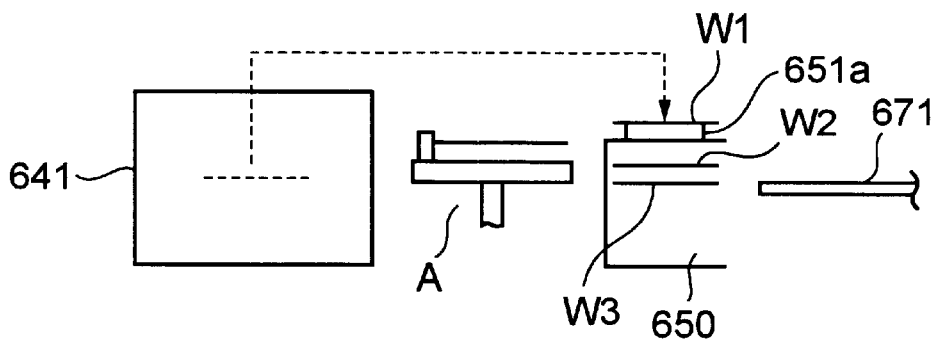
FIGS. 42A to 42D are schematic diagrams showing other steps of a method used in the coating and developing apparatus according to the present invention.
Figure 42B:
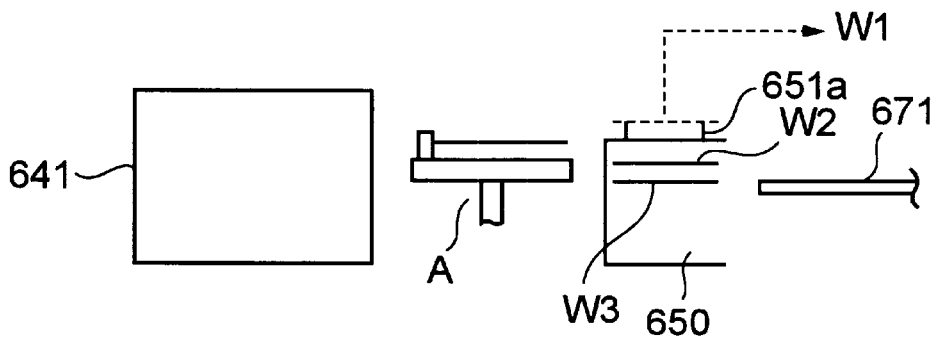

As shown in FIG. 42A, after a predetermined inspection has been completed for the wafer W1, it is transferred to the transferring stage 605 by the auxiliary transfer mechanism A. As shown in FIG. 42B, the main transfer mechanism MA transfers the wafer W1 to the cassette stage 621 through the transferring portion of the shelf units R. When the inspected result is successful, the wafer W1 is returned to the original cassette C. When the inspected result is not successful, the wafer W1 is placed in an unsuccessful wafer cassette C1. Alternatively, all wafers W may be returned to the original cassette C. Information of inspected result may be controlled corresponding to software.

Figure 42C:
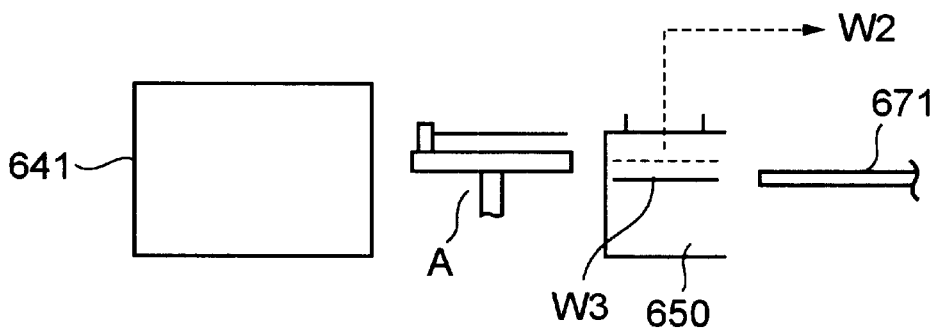
Figure 42D:
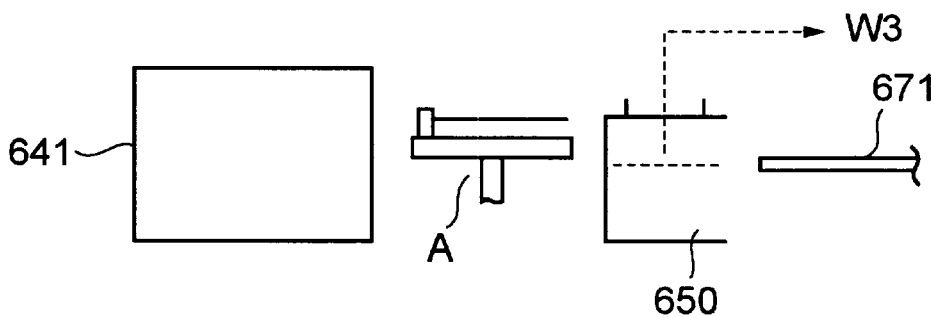

Since the fourth wafer W4 is transferred 72 seconds after the first wafer W1, after the main transfer mechanism MA transfers the first wafer W1, before the wafer W4 is transferred, as shown in FIGS. 42C and 42D, the second wafer W2 and the third wafer W3 are transferred to the same cassette C as the wafer W1 in the order of the wafers contained therein. After the developing process, the heating process, and the cooling process are performed for the fourth wafer W4 to the last wafer W, they are returned to the same cassette C as the wafer W1 in the order of the wafers contained therein.

The cassette C that contains wafers W that have been successful in the inspection is transferred to the next step. In contrast, the cassette C1 that contains wafers W that have not been successful in the inspection is transferred to a cleaning portion (not shown). The cleaning portion dissolves the resist from each wafer W and restores it to the state before it is transferred to the coating and developing apparatus 600.

According to the present invention, since the inspecting unit 604 is integrated with the coating and developing apparatus 600, it is not necessary to convey wafers W. In addition, it is not necessary to cause wafers W processed in an external coating and developing apparatus 600 to wait for an inspection, the throughput is improved.

In addition, one operator can supervise the coating and developing process and the inspection and know the inspected results on real time basis. Thus, when the operator is informed of a defect in an inspection, he or she can seek the cause and take a proper action therefore.

In addition, according to the present invention, since the inspecting unit 604 is integrated with the processing station 602, in addition to the case that the inspection is performed after the developing process, even in the case that a predetermined inspection is performed after the resist solution coating process or the exposing process is performed, the inspection can be performed without need to change the process flow. In other words, in the conventional coating and developing apparatus, the transferring flow for wafers W is fixed. A non-exposed wafer W is transferred from the cassette station 601 to the aligner S5 (namely, from the left to right in the X direction). An exposed wafer W is transferred from the cassette station 601 to the aligner S5 in the reverse direction (namely, from right to left in the X direction).

Thus, in the case that the inspecting unit 604 is integrated with the processing station 602, when the inspection is performed after the resist solution coating process is performed, a wafer W is transferred in the path of the resist solution coating process, the inspection, the interface station 603, and the aligner S5. In contrast, when the inspection is performed after the exposing process is performed, a wafer W is transferred in the path of the aligner S5, the interface station 603, the inspection of the processing station 602, and the developing process. When the inspection is performed after the developing process is performed, a wafer W is transferred in the path of the aligner S5, the interface station 603, the developing process of the processing station 602, and the inspection. Thus, the predetermined inspection can be performed after any process is performed without an inconsistency of the transferring flow of a wafer W.

After the resist solution coating process is performed, there are inspections for coated irregularities of resist solution, film thickness of coated resist solution, and so forth. These inspections are performed by the above-described defect inspecting apparatus 641C and other film thickness inspecting apparatus (not shown). As inspections performed after the exposing process is performed, there is an exposed state inspection such as a defocus inspection for a deviation of a pattern formed by the aligner. This inspection can be performed using a CCD camera as with the above-described inspections.

In addition, according to the present invention, when wafers W that have been processed in the coating and developing apparatus 600 are sample-inspected, even if the throughput of the inspecting unit 604 is lower than the throughput of the coating and developing apparatus 600, the wafers W can be returned to the cassette C in the order of those that are taken therefrom without need to prepare a complicated sample-inspection transferring program.

In other words, the inspecting unit 604 has the transferring stage 605 on which a wafer W that is inspected is transferred and the wafer holding portion 650 that holds wafers W that are not inspected. While the inspecting portions 641 is inspecting an inspecting wafer W1, wafers W (for example, a second wafer W2 and a third wafer W3) that are transferred from a preprocess portion for the inspecting portion are transferred to the wafer holding portion 650 by the main transfer mechanism MA corresponding to the transferring intervals of wafers W of the coating and developing apparatus 600. The second wafer W2 and the third wafer W3 are held in the wafer holding portion 650 until the inspection for the wafer W1 is completed. After the inspection for the first wafer W1 has been completed and unloaded from the inspecting unit 604, the wafers W held in the inspecting unit 604 are unloaded. Thus, the wafers W can be unloaded from the inspecting unit 604 without an inconsistency of the order of wafers W contained in the cassette C. Thus, the wafers W can be returned to the cassette C in the order of those contained therein.

As described above, a wafer W that is sample-inspected is selected every three or more wafers. Alternatively, one wafer W may be selected from each cassette C. Alternatively, a plurality of wafers W may be selected from each cassette C. Alternatively, one wafer W may be selected from a plurality of cassettes C.

The present invention can be applied to the case that after a developing process is performed the processed state is inspected. In addition, the present invention can be applied to the case that after a resist coating process is performed the processed state is inspected and the case that after an exposing process is performed the processed state is inspected.

According to the present invention, the transferring stage 605 and the wafer holding portion 650 may be separately disposed. Alternatively, the wafer holding portion 650 may have two open sides from which both the main transfer mechanism MA and the auxiliary transfer mechanism A can access. In addition, a part of the wafer holding portion 650 (for example, the top shelf or the bottom shelf) may be used as the transferring stage 605. The transferring stage 605 may have a loading stage and an unloading stage. The wafer holding portion 650 may have the same structure as the transferring stage 605 as long as the wafer holding portion 650 can hold a wafer W.

The inspecting unit 604 structured as shown in FIG. 37 may be disposed in the interface station 603. In this case, the transfer mechanism 676 transfers a wafer W to the transferring stage 605 and the wafer holding portion 650.

In addition, the present invention can be applied to the case that a processed wafer W is sample-inspected and that the throughput of the inspecting unit 604 is higher than the throughput of the coating and developing apparatus 600. In this case, it is not necessary to convey a wafer W to the wafer holding portion 650. When all wafers W that have been processed are inspected, wafers W that are inspected may be transferred to the wafer holding portion 650. In this case, the main transfer mechanism MA transfers wafers W between the transferring stage 605 and the wafer holding portion 650.

In this case, the inspecting portions may be apparatuses that inspect particles, EBR widths, WEE widths, coated irregularities, developed irregularities, non-coated portion, non-developed portion, line widths, exposed focus deviation, and so forth as well as a line width inspecting apparatus, a matching inspecting apparatus, and a defect inspecting apparatus.

The substrate processing portions of the processing unit U may be for example a reflection protection film coating unit and so forth as well as the coating unit 632 and the developing unit 631. The number of those apparatuses may be freely designated.

In addition, instead of performing the hydrophobic process on the front surface of a wafer W, a reflection protection film may be formed. The wafers W may be glass substrates for liquid crystal display as well as wafers.

According to the present invention, since the inspecting portion is disposed in the substrate processing apparatus, the operation time period necessary for the substrate process and the inspection can be shortened. Thus, the throughput of the apparatus can be improved. In addition, according to the present invention, when processed substrates are sample-inspected, the inspected wafers W can be returned to the original cassette in the order of those contained therein without need to use a complicated transferring program.

The disclosure of Japanese Patent Application No.2000-211532 filed Jul. 12, 2000, No.2000-217722 filed Jul. 18, 2000 and No.2000-238468 filed Aug. 7, 2000, including specification, drawings and claims are herein incorporated by reference in its entirety.

Although only some exemplary embodiments of this invention have been described in detail above, those skilled in the art will readily appreciated that many modifications are possible in the exemplary embodiments without materially departing from the novel teachings and advantages of this invention. Accordingly, all such modifications are intended to be included within the scope of this invention.

What is claimed is:
1. A substrate processing apparatus, comprising:
    a cassette station having:
        a holding portion for holding a substrate cassette that contains a plurality of substrates, and
        a transferring portion for transferring the substrate to and from the substrate cassette placed on the holding portion;
    a processing station having a substrate processing portion for coating a process solution on the substrate transferred from the cassette station;
    an inspecting station connected to the processing station, the inspecting station having an inspecting portion for inspecting a processed state of the substrate processing portion for the substrate; and
    a main transfer mechanism for transferring the substrate between the processing station and the inspecting station.
2. The substrate processing apparatus as set forth in claim 1,
    wherein the inspecting station and the processing station are adjacently disposed, and
    wherein the width in the direction approximately perpendicular to the direction of the disposition of the inspecting station is equal to or smaller than the width in the direction approximately perpendicular to the disposition of the processing station.
3. The substrate processing apparatus as set forth in claim 1,
    wherein the inspecting station is connected to the processing station in the direction approximately perpendicular to the direction of the disposition of the substrate cassette on the cassette station.
4. The substrate processing apparatus as set forth in claim 1,
    wherein the inspecting station is disposed in such a manner that the inspecting station is connectable to and disconnectable from at least one of said cassette station and said processing station.
5. The substrate processing apparatus as set forth in claim 1,
    wherein the inspecting station has a plurality of types of inspecting portions.
6. The substrate processing apparatus as set forth in claim 1,
    wherein the inspecting station has a storing portion for a material used in the substrate processing portion.
7. The substrate processing apparatus as set forth in claim 6,
    wherein the substrate processing portion supplies predetermined solution on the substrate, and
    wherein the material stored in the storing portion is the predetermined solution.
8. The substrate processing apparatus as set forth in claim 6,
    wherein the inspecting station has a main transfer mechanism for transferring the substrate to and from the processing station.
9. The substrate processing apparatus as set forth in claim 1,
    wherein the inspecting station has a substrate transferring portion.
10. The substrate processing apparatus as set forth in claim 1,
    wherein the inspecting station has a substrate transferring portion for transferring the substrate to and from the transferring portion of the cassette station.
11. The substrate processing apparatus as set forth in claim 1,
    wherein in the inspecting station, a plurality of inspecting portions are disposed symmetrically with respect to a line that divides the direction of the disposition of the inspecting station into two.
12. The substrate processing apparatus as set forth in claim 1,
    wherein the inspecting station has an adjusting portion for adjusting at least one of the temperature and humidity of the interior of the inspecting station.
13. The substrate processing apparatus as set forth in claim 1,
    wherein the cassette station, the processing station, and the inspecting station are disposed in the direction approximately perpendicular to the direction of the disposition of the substrate cassette on the cassette station, and
    wherein the inspecting station is disposed midway between the cassette station and the processing station.
14. The substrate processing apparatus as set forth in claim 1,
    wherein the cassette station, the processing station, and the inspecting station are disposed in the direction approximately perpendicular to the direction of the disposition of the substrate cassette on the cassette station, and
    wherein the processing station is disposed midway between the cassette station and the inspecting station.

15. The substrate processing apparatus as set forth in claim 1,
 wherein the processing station has a plurality of substrate processing portions,
 wherein at least one of said substrate processing portions coats a developing solution on the substrate that has been coated with a resist solution and exposed so as to perform a developing process,
 wherein the inspecting station has a plurality of inspecting apparatuses,
 wherein at least one of said inspecting apparatuses inspects the processed state of the developing process for the substrate,
 wherein the cassette station, the processing station, and the inspecting station are disposed in the direction approximately perpendicular to the direction of the disposition of the substrate cassette on the cassette station, and
 wherein the inspecting station is disposed midway between the cassette station and the processing station.

16. The substrate processing apparatus as set forth in claim 1,
 wherein the processing station has a plurality of substrate processing portions,
 wherein at least one of said substrate processing portions coats a resist solution on the substrate,
 wherein the inspecting station has a plurality of inspecting apparatuses,
 wherein at least one of said inspecting apparatuses inspects the coated state of a resist solution on the substrate,
 wherein the cassette station, the processing station, and the inspecting station are disposed in the direction approximately perpendicular to the direction of the disposition of the substrate cassette on the cassette station, and
 wherein the processing station is disposed midway between the cassette station and the inspecting station.

17. The substrate processing apparatus as set forth in claim 1,
 wherein the inspecting portion measures the film thickness of a coated film formed on the substrate.

18. The substrate processing apparatus as set forth in claim 1,
 wherein the inspecting portion inspects the surface state of a coated film formed on the substrate.

19. The substrate processing apparatus as set forth in claim 1,
 wherein the substrate processing apparatus is disposed in a clean room, and
 wherein the following relation is satisfied:

first pressure>second pressure>third pressure>fourth pressure where the first pressure is the inner pressure of the processing station, the second pressure is the inner pressure of the cassette station, the third pressure is the inner pressure of the inspecting station, and the fourth pressure is the inner pressure of the clean room.

20. A substrate processing apparatus, comprising:
 a cassette station having:
 a holding portion for holding a substrate cassette that contains a plurality of substrates, and
 a transferring portion for transferring a substrate to and from the substrate cassette placed on the holding portion;
 a first processing station having a first substrate processing portion for coating a first process solution on the substrate transferred from the cassette station;
 a second processing station having a second substrate processing portion for coating a second process solution on the substrate transferred from the cassette station;
 a first inspecting station disposed midway between the first processing station and the second processing station, the first inspecting station having a first inspecting portion for inspecting the substrate; and
 a main transfer mechanism for transferring the substrate among the first processing station, the second processing station, and the first inspecting station,
 wherein the cassette station, the first processing station, the second processing station, and the first inspecting station are disposed in the direction approximately perpendicular to the direction of the disposition of the substrate cassette on the cassette station.

21. The substrate processing apparatus as set forth in claim 20, further comprising:
 a second inspecting station disposed midway between the cassette station and the first processing station, the second inspecting station having a second inspecting portion for inspecting the substrate.

22. The substrate processing apparatus as set forth in claim 20, further comprising:
 an interface station for transferring the substrate to and from an aligner; and
 a third inspecting station disposed midway between the second processing station and the interface station, the third inspecting station having a third inspecting portion for inspecting the substrate.

23. A substrate processing apparatus, comprising:
 a cassette station having:
 a holding portion for holding a substrate cassette that contains a plurality of substrates, and
 a transferring portion for transferring the substrate to and from the substrate cassette placed on the holding portion;
 a processing station having a substrate processing portion for coating a process solution on the substrate transferred from the cassette station;
 an interface station for transferring the substrate to and from an aligner;
 a first inspecting station disposed midway between the cassette station and the processing station, the first inspecting station having a first inspecting portion for inspecting a substrate; and
 a second inspecting station disposed midway between the processing station and the interface station, the second inspecting station having a second inspecting portion for inspecting a substrate.

24. A substrate processing apparatus, comprising:
 a carrier station having:
 a carrier loading/unloading portion for loading and unloading a carrier that contains a plurality of substrates, and
 a transferring portion for transferring the substrate to and from the carrier on the carrier loading/unloading portion;
 a processing station disposed adjacent to the carrier station, the processing station having:
 a coating portion for coating a resist on the substrate, a developing portion for developing the substrate that has been exposed, and a main transferring portion for transferring the substrate to the coating portion and the developing portion and transferring the substrate to and from the transferring portion; and an inspecting station disposed adjacent to the carrier station, the inspecting station having an inspecting portion for inspecting the substrate.

25. The substrate processing apparatus as set forth in claim 24, further comprising:

an external carrier holding portion for holding the carrier that contains the substrate that has been processed outside the substrate processing apparatus; and a mode selecting portion for selecting a regular operation mode in which the inspecting portion inspects the substrate processed in the processing station or an inspecting portion dedicated operation mode in which the inspecting portion inspects the substrate processed outside the substrate processing apparatus.

26. The substrate processing apparatus as set forth in claim 25, wherein the external carrier holding portion is disposed in the carrier station.

27. The substrate processing apparatus as set forth in claim 25, wherein the external carrier holding portion is a part of the carrier loading/unloading portion of the carrier station.

28. The substrate processing apparatus as set forth in claim 25, wherein the inspecting station has an auxiliary transferring portion for transferring a substrate to and from the inspecting portion, wherein an intermediate holding portion is disposed in the carrier station, in the inspecting station, or midway between the carrier station and the inspecting station, the intermediate holding station temporarily holding the substrate, and wherein the transferring portion of the carrier station transfers the substrate developed in the processing station and the substrate contained in a carrier on the external carrier holding portion to and from the auxiliary transferring portion through the intermediate holding portion.

29. The substrate processing apparatus as set forth in claim 25, further comprising:

a multi-staged holding portion for temporarily holding at least one substrate that has been developed in the processing station before the substrate is transferred to the inspecting portion of the inspecting station.

30. The substrate processing apparatus as set forth in claim 25, wherein the multi-staged holding portion also functions as an intermediate holding portion for transferring the substrate between the transferring portion and the auxiliary transferring portion.

31. The substrate processing apparatus as set forth in claim 25, wherein a plurality of inspecting portions are disposed in the vertical direction.

32. A substrate processing apparatus, comprising:

a carrier station having:

a carrier loading/unloading portion for loading and unloading a carrier that contains a plurality of substrates, and a first transferring portion for transferring the substrate to and from the carrier on the carrier loading/unloading portion;

a processing station disposed adjacent to the carrier station, the processing station having:

a coating portion for coating a resist on a substrate, a developing portion for developing a substrate that has been exposed, and a main transferring portion for transferring the substrate to the coating portion and the developing portion and transferring the substrate to and from the transferring portion; and an inspecting station disposed adjacent to the carrier station, the inspecting station having an inspecting portion for inspecting the substrate that has been processed;

an external carrier holding portion for holding the carrier that contains the substrate that has been processed outside the substrate processing apparatus;

a second transferring portion for transferring the substrate between the carrier on the external carrier holding portion and the inspecting station; and a mode selecting portion for selecting a regular operation mode in which the inspecting portion inspects the substrate processed in the processing station or an inspecting portion dedicated operation mode in which the inspecting portion inspects the substrate processed outside the substrate processing apparatus.

33. The substrate processing apparatus as set forth in claim 32, wherein the inspecting station has an auxiliary transferring portion for transferring the substrate to and from the inspecting portion.

34. The substrate processing apparatus as set forth in claim 32, wherein the external carrier holding portion and the second transferring portion are disposed midway between the carrier station and the inspecting station, and wherein in the regular operation mode, the second transferring portion transfers the substrate between the first transferring portion and the auxiliary transferring portion of the inspecting station.

35. The substrate processing apparatus as set forth in claim 32, further comprising:

a multi-staged holding portion for temporarily holding at least one substrate that has been developed in the processing station before the substrate is transferred to the inspecting portion of the inspecting station.

36. A substrate processing apparatus, comprising:

a carrier station having:

a carrier loading/unloading portion for loading and unloading a carrier that contains a plurality of substrates, and a first transferring portion for transferring the substrate to and from the carrier on the carrier loading/unloading portion;

a processing station disposed adjacent to the carrier station, the processing station having:

a coating portion for coating a resist on a substrate, a developing portion for developing the substrate that has been exposed, and a main transferring portion for transferring the substrate to the coating portion and the developing portion and transferring the substrate to and from the transferring portion;

an inspecting station disposed adjacent to the carrier station, the inspecting station having:

an inspecting portion for inspecting the substrate that has been processed, an external carrier holding portion for holding the carrier that contains the substrate that has been processed outside the substrate processing apparatus, and an auxiliary transferring portion for transferring the substrate among the transferring portion, the inspecting portion, and the external carrier holding portion; and a mode selecting portion for selecting a regular operation mode in which the inspecting portion inspects the substrate processed in the processing station or an inspecting portion dedicated operation mode in which the inspecting portion inspects the substrate processed outside the substrate processing apparatus.

37. A substrate processing apparatus, comprising:

a carrier station having:

a carrier loading/unloading portion for loading and unloading a carrier that contains a plurality of substrates, and a transferring portion for transferring the substrate to and from the carrier placed on the carrier loading/unloading portion;

a processing station disposed adjacent to the carrier station, the processing station having:

a coating portion for coating a resist on the substrate, a developing portion for developing the substrate that has been exposed, and a main transferring portion for transferring the substrate to the coating portion and the developing portion and transferring the substrate to and from the transferring portion; and an inspecting station disposed adjacent to the processing station, the inspecting station having an inspecting portion for inspecting the substrate.

38. A substrate processing apparatus, comprising:

a carrier station having:

a carrier loading/unloading portion for loading and unloading a carrier that contains a plurality of substrates, and a transferring portion for transferring the substrate to and from the carrier placed on the carrier loading/unloading portion;

a processing station disposed adjacent to the carrier station, the processing station having:

a coating portion for coating a resist on the substrate, a developing portion for developing the substrate that has been exposed, and a main transferring portion for transferring the substrate to the coating portion and the developing portion and transferring the substrate to and from the transferring portion;

an interface station, disposed midway between an aligner and the processing station, for transferring the substrate to and from the aligner; and an inspecting station disposed adjacent to the interface station, the inspecting station having an inspecting portion for inspecting the substrate.

39. A substrate processing apparatus, comprising:

a cassette station having:

a holding portion for holding a substrate cassette that contains a plurality of substrates, and a transferring portion for transferring the substrate to and from the substrate cassette on the holding portion;

a processing station having a substrate processing portion for coating a process solution on the substrate transferred from the cassette station;

an interface station, disposed adjacent to an aligner, for transferring the substrate to and from the aligner;

a first inspecting station disposed midway between the processing station and the interface station, the first inspecting station having a first inspecting portion for inspecting the substrate; and a second inspecting station disposed adjacent to the cassette station, the second inspecting station having a second inspecting portion for inspecting the substrate.

40. A substrate processing apparatus, comprising:

a cassette station having:

a holding portion for holding a substrate cassette that contains a plurality of substrates, and a transferring portion for transferring the substrate to and from the substrate cassette on the holding portion;

a processing station having a substrate processing portion for coating a process solution on the substrate transferred from the cassette station;

an interface station, disposed midway between an aligner and the processing station, for transferring the substrate to and from the aligner;

a first inspecting station disposed midway between the cassette station and the processing station, the first inspecting station having a first inspecting portion for inspecting the substrate; and a second inspecting station disposed adjacent to the interface station, the second inspecting station having a second inspecting portion for inspecting the substrate.

41. A substrate processing apparatus, comprising:

a cassette station having:

a holding portion for holding a substrate cassette that contains a plurality of substrates, and a transferring portion for transferring the substrate to and from the substrate cassette on the holding portion;

a processing station disposed adjacent to the cassette station, the processing station having:

a substrate processing portion for coating a process solution on the substrate, and a main transfer mechanism for transferring substrates to the substrate processing portion in the order of those contained in the substrate cassette and transferring the substrates to and from the transferring portion in the order of those contained in the substrate cassette;

an inspecting portion for inspecting the processed state of the substrate processing portion for the substrate;

an inspecting substrate holding portion for holding an inspecting substrate that has been processed outside the substrate processing apparatus and that is inspected in the inspecting portion;

a substrate holding portion for holding substrates that have been processed in the substrate processing portion and that are later than the inspecting substrate in the substrate cassette in the order of those contained therein; and a main transfer mechanism for transferring the substrate that has been processed in the substrate processing portion to the inspecting substrate holding portion and the substrate holding portion.

42. The substrate processing apparatus as set forth in claim 41, further comprising:
an auxiliary transfer mechanism for transferring the substrate between the inspecting portion and the inspecting substrate holding portion.

43. The substrate processing apparatus as set forth in claim 41,
wherein the inspecting portion, the inspecting substrate holding portion, and the substrate holding portion are disposed in the processing station,
wherein the main transfer mechanism is composed of the main transfer mechanism, and
wherein the main transfer mechanism transfers the inspecting substrate processed in the substrate holding portion to and from the inspecting substrate holding portion.

44. The substrate processing apparatus as set forth in claim 41,
wherein the inspecting portion, the inspecting substrate holding portion, and the substrate holding portion are disposed adjacent to the cassette station,
wherein the main transfer mechanism is composed of the transferring portion, and
wherein the transferring portion transfers the inspecting substrate processed in the substrate holding portion to and from the inspecting substrate holding portion.

45. The substrate processing apparatus as set forth in claim 41,
wherein a plurality of inspecting portions for inspecting a plurality of inspections for the substrate are disposed in the vertical direction.

46. The substrate processing apparatus as set forth in claim 41,
wherein at least one of the substrate processing portions of the processing stations coats a developing solution on the substrate that has been coated with a resist solution and exposed so as to perform a developing process, and
wherein at least one of the inspecting portions inspects the processed state of the developing process for the substrate.

47. The substrate processing apparatus as set forth in claim 41,
wherein at least one of the substrate processing portions of the processing station coats a resist solution on the substrate, and
wherein one of the inspecting portions inspects the coated state of the resist solution for the substrate.

48. The substrate processing apparatus as set forth in claim 41,
wherein the inspecting portion measures the line widths of a resist pattern formed on the substrate.

49. The substrate processing apparatus as set forth in claim 41,
wherein the inspecting portion inspects the matching of the resist pattern and the base pattern formed on the substrate.

50. The substrate processing apparatus as set forth in claim 46,
wherein the inspecting portion inspects the surface state of the coated film formed on the substrate.

51. A substrate processing method, comprising the steps of:
transferring a plurality of substrates contained in a substrate cassette to a substrate processing portion in the order of the substrates contained in the substrate cassette and coating a process solution on the substrates;
unloading a substrate processed in the substrate processing portion from the substrate processing portion;
transferring an inspecting substrate selected from a predetermined number of substrates unloaded from the substrate processing portion to an inspecting portion and causing the inspecting portion to inspect the processed state of the substrate processing portion;
transferring substrates later than an inspecting substrate to a substrate holding portion and causing the substrate holding portion to hold the substrates in the order of the substrates contained in the substrate cassette until the inspecting portion completes the inspection of the inspecting substrate when the process time period of the inspecting portion is longer than the transferring intervals of substrates transferred from the substrate processing portion;
unloading the inspecting substrate that has been inspected in the inspecting portion from the inspecting portion; and
unloading the inspecting substrate from the inspecting portion and then unloading the substrates held in the substrate holding portion therefrom in the order of the substrates contained in the substrate cassette.

52. The substrate processing method as set forth in claim 51,
wherein the substrate processing portion coats a developing solution on the substrate that has been coated with a resist solution and exposed so as to perform a developing process, and
wherein the inspecting portion inspects the processed state of the developing process for the substrate.

53. The substrate processing method as set forth in claim 51,
wherein the substrate processing portion coats a resist solution on a substrate, and
wherein the inspecting portion inspects the coated state of the resist solution for the substrate.

* * * * *